United States Patent [19]

Yoshioka et al.

[11] Patent Number: 4,533,730
[45] Date of Patent: * Aug. 6, 1985

[54] 1-OXADETHIACEPHAM COMPOUNDS

[75] Inventors: Mitsuru Yoshioka; Uyeo Shoichiro, both of Toyonaka; Yoshio Hamashima, Kyoto; Ikuo Kikkawa, Takarazuka; Teruji Tsuji, Takatsuki; Wataru Nagata, Nishinomiya, all of Japan

[73] Assignee: Shionogi & Co., Ltd., Osaka, Japan

[ * ] Notice: The portion of the term of this patent subsequent to Apr. 17, 2001 has been disclaimed.

[21] Appl. No.: 543,940

[22] Filed: Oct. 19, 1983

Related U.S. Application Data

[60] Division of Ser. No. 374,862, May 4, 1982, Pat. No. 4,443,598, which is a continuation-in-part of Ser. No. 322,662, Nov. 18, 1981, Pat. No. 4,366,316, which is a continuation of Ser. No. 72,600, Sep. 5, 1979, abandoned, which is a continuation of Ser. No. 877,811, Feb. 14, 1978, abandoned.

[30] Foreign Application Priority Data

Feb. 15, 1977 [JP] Japan .................. 52-15813
Jun. 6, 1977 [JP] Japan .................. 52-67025
Oct. 1, 1980 [JP] Japan .................. 55-138092

[51] Int. Cl.³ ........................... C07D 498/04
[52] U.S. Cl. ........................... 544/92; 544/64; 544/69
[58] Field of Search ............ 544/90, 92, 64, 69

[56] References Cited

U.S. PATENT DOCUMENTS

| | | | |
|---|---|---|---|
| 4,013,653 | 3/1977 | Wolfe | 544/90 |
| 4,044,002 | 8/1977 | Hatfield | 544/16 |
| 4,079,179 | 3/1978 | Christensen et al. | 544/28 |
| 4,138,486 | 3/1979 | Narisada et al. | 544/90 X |
| 4,150,156 | 4/1979 | Beattie | 544/90 |
| 4,159,984 | 7/1979 | Yoshioka et al. | 544/90 |
| 4,183,855 | 1/1980 | Yoshioka et al. | 544/90 |
| 4,207,782 | 5/1980 | Narisada et al. | 544/90 X |
| 4,233,216 | 11/1980 | Uyeo et al. | 544/90 X |
| 4,443,598 | 4/1984 | Yoshioka et al. | 544/90 |

Primary Examiner—Richard L. Raymond
Attorney, Agent, or Firm—Wenderoth, Lind & Ponack

[57] ABSTRACT

Intermediates for preparing an antibacterial 1-dethia-1-oxacephalosporins which are represented by the following formula:

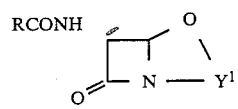

wherein

R is a monovalent group (minus the carbonyl) from an acyl derived from a carboxylic or carbonic acid;
$Y^1$ is a divalent group of the following formula:

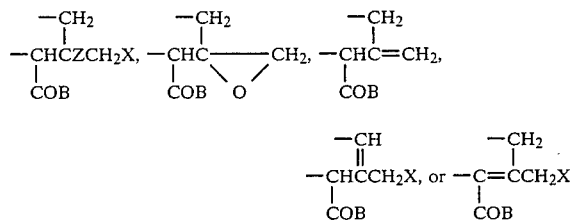

wherein
COB is carboxy or protected carboxy;
X is hydrogen or a nucleophilic group; and
Z is a leaving group
are prepared from a compound of the following formula;

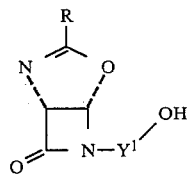

wherein R and $Y^1$ are as defined above by the action of an acid.

The new compounds of this invention shown by the following formula:

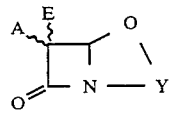

wherein
A is amino or substituted amino;
E is hydrogen or methoxy; and
Y is a divalent group of the following formula:

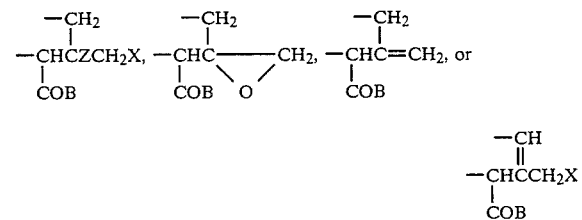

in which COB, X, and Z are as defined above are convertible into other compounds of the same formula by applying conventional methods in β-lactam chemistry.

6 Claims, No Drawings

1-OXADETHIACEPHAM COMPOUNDS

This application is a division of application Ser. No. 374,862, filed May 4, 1982 (now U.S. Pat. No. 4,443,598), which application is a continuation-in-part of application Ser. No. 322,662, filed Nov. 18, 1981 (now U.S. Pat. No. 4,366,316), which is a continuation of application Ser. No. 72,600, filed Sept. 5, 1979 (now abandoned), which is a continuation of application Ser. No. 877,811, filed Feb. 14, 1978 (now abandoned).

This invention relates to novel 1-dethia-1-oxacepham compounds. More specifically, it relates to Compounds I represented by the formula I given below, processes for preparing the same, and the use of Compounds I as new intermediates for preparing potent known antibacterials, 1-dethia-1-oxacephalosporins.

INTRODUCTION

(Prior art)

Antibacterial 1-dethia-1-oxacephalosporins of the following formula are described by Christensen in the Journal of American Chemical Society, 96, 7582 (1974): and by several firms in their patent publications.

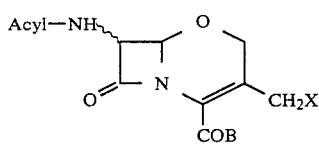

(X is hydrogen, acetoxy, or methyltetrazolylthio).

They have been prepared as following schemes by several synthetic routes. But, because the reaction proceeds through an intermediary carbonium ion at position 4 of the azetidinone, the introduction of the oxygen function there results in epimeric mixture. This mixture gives about a half of ineffective 6-epimer of desired 1-dethia-1-oxacephalosporin.

Scheme 1

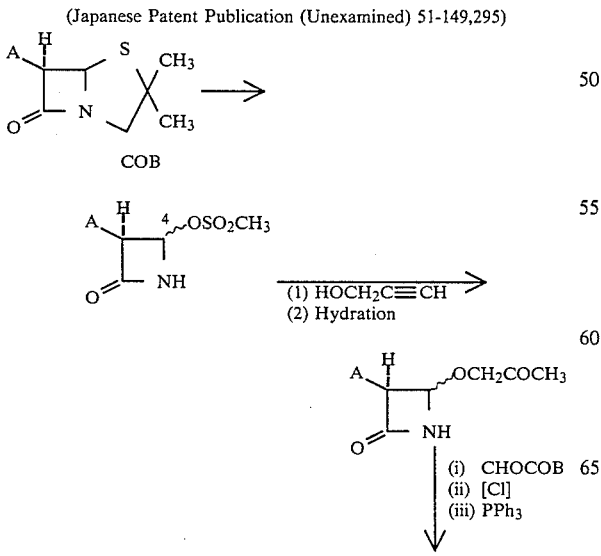

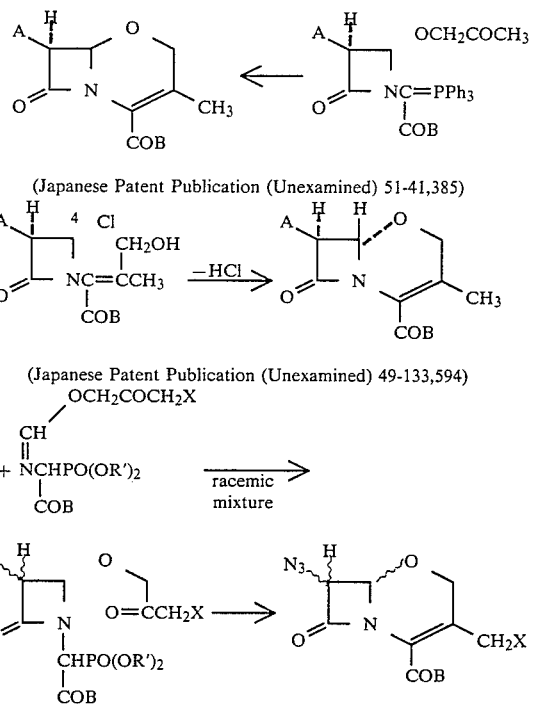

(wherein
A is amino or substituted amino;
COB is carboxy or protected carboxy;
X is hydrogen or nucleophilic group;
Ph is phenyl; and
R' is aryl or alkyl).

DETAILED DESCRIPTION OF THE INVENTION

The first gist of this invention is based on the discovery that the starting material II, vide infra, cyclizes by the attack of oxygen from the reverse side of the ring juncture and results in favorable stereospecific formation of the carbon to oxygen bond. The formed α-RCONH group can be replaced by β-RCONH by introduction of methoxy at position 7α or through a Schiff base formation, epimerization and hydrolysis, finally giving the desired 1-dethia-1-oxacephalosporin having favorable stereochemistry. Other aspects of this invention are the synthetic processes represented by either one of the following reaction schemes (1) through (5) and intermediate compounds I given in item (6) below:

(1) Cyclization (Numbers in parentheses show position numbers on the nucleus)

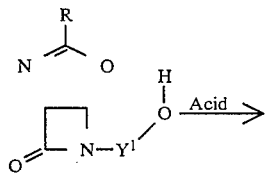

-continued

RCONH (7) (6) O(1)
         ┌─────┐
         │     │─Y¹  { (2)
         N─────    (3)
    O  (8)  (5)    (4)

(2) Methoxylation imino formation then methanol addition →

(3) Addition of XZ

XZ addition →

(4) Elimination of HZ

HZ elimination → and (5) Other modifications on the molecule.

In the above reaction schemes:
   A is amino or substituted amino;
   E is hydrogen or methoxy;
   Y is a divalent group of the following formula:

$$-\underset{\underset{COB}{|}}{CH}-CH_2CH_2X,\quad -\underset{\underset{COB}{|}}{CH}-\underset{|}{CH}\overset{CH_2}{\underset{O}{<}},$$
(4)                    (4)

$$-\underset{\underset{COB}{|}}{CH}-C=CH_2,\quad \text{or}\quad -\underset{\underset{COB}{|}}{CH}-\overset{CH}{\underset{\|}{C}}CH_2X$$
(4)                    (4)

R is a monovalent group (minus the carbonyl function of an acyl group derived from a carboxylic or carbonic acid;
Y¹ is a divalent group Y or $$-\underset{\underset{COB}{|}}{C}=\overset{-CH_2}{\underset{}{C}}H_2X$$
(4)

COB is carboxy or protected carboxy;
X is a hydrogen or a nucleophilic group; and
Z is a leaving group.

(6) The compounds of the following formula:

(I)

wherein A, E and Y are as defined above.

I. COMPOUNDS

The substances provided by this invention are Compounds I represented by the following formula I:

(I)

wherein
   A is amino or substituted amino;
   E is β-hydrogen or α-methoxy; and
   Y is a divalent group of the following formula:

$$-\underset{\underset{COB}{|}}{CH}-CH_2CH_2X,\quad -\underset{\underset{COB}{|}}{CH}-\underset{|}{CH}\overset{CH_2}{\underset{O}{<}},$$

$$-\underset{\underset{COB}{|}}{CH}-C=CH_2,\quad \text{or}\quad -\underset{\underset{COB}{|}}{CH}-\overset{CH}{\underset{\|}{C}}CH_2X$$

in which
   COB is carboxy or protected carboxy;
   X is hydrogen or a nucleophilic group; and
   Z is a leaving group.

The amino substituent of the substituted amino group for A can be selected from known side chains of natural or synthetic penicillins or cephalosporins, or their equivalents (e.g. alcyl, hydrocarbyl, hydrocarbylidene, organic silyl or sulfenyl groups, or similar amino substituent which are conventional in the field of cephalosporin or penicillin chemistry). There is a wide variation of possible groups A since they generally have little direct relationship to modification of the substituents at other parts of the nucleus.

Said acyl may contain up to 20 carbon atoms and include the following typical examples:

(1) $C_1$ to $C_{10}$ alkanoyl e.g. formyl, acetyl, propionyl, butyryl, isobutyryl, cyclopropylacetyl, trimethylacetyl, valeryl, t-butylacetyl, caproyl, octanoyl, cyclohexylacetyl, decanoyl, 2-ethylenanthoyl, or like alkanoyl;

(2) $C_1$ to $C_7$ haloalkanoyl e.g. chloroacetyl, chloropropionyl, chloroisovaleryl, dichloroacetyl, trichloroacetyl, trichloropropionyl, bromoacetyl, bromopropionyl, dibromocyclohexylcarbonyl, or the like haloalkanoyl;

(3) azidoacetyl, cyanoacetyl, trifluoromethylthioacetyl, cyanomethylthioacetyl, or (4-pyridon-1-yl)acetyl;

(4) acyl groups of the following formula:

wherein Ar is an aryl e.g. furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, dihydrophenyl, tetrahydrophenyl, tetrahydropyrimidyl, naphthyl, benzothiazolyl, indolyl, quinolyl, isoquinolyl, benzopyrimidyl, cinnolinyl, pyridopyrimidyl, indanyl, or the like aryl, and each is unsubstituted or substituted by a substituent e.g. methyl, ethyl, propyl, hydroxymethyl, chloromethyl, trifluoromethyl, cyano, carboxy, carboxymethyl, aminomethyl, phenyl, chlorophenyl, fluorophenyl, amino, formylamino, acetamido, propionamido, butyrylamino, valeramido, isovaleramido, imino, nitro, hydroxy, methoxy, ethoxy, propoxy, methylenedioxy, ethylenedioxy, formyloxy, acetoxy, propionyloxy, butyryloxy, valeryloxy, phenylacetoxy, benzoyloxy, methanesulfonyloxy, ethanesulfonyloxy, benzenesulfonyloxy, bromobenzenesulfonyloxy, methoxycarbonyloxy, ethoxycarbonyloxy t-butoxycarbonyloxy, benzyloxycarbonyloxy, carbamoyloxy, methylcarbamoyloxy, oxo, chloro, bromo, iodo, or the like substituent;

(5) acyl group of the following formula:

wherein Ar is as defined above and Q and Q' each is hydrogen or methyl;

(6) acyl group of the following formula:

wherein Ar, Q, and Q' are as defined above and G is oxygen, sulfur, or imino;

(7) acyl group of the following formula:

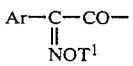

wherein Ar is as defined above and T$^1$ is hydrogen or C$_1$ to C$_6$ alkyl e.g. methyl, ethyl, propyl, isopropyl, butyl, isobutyl, secondary butyl, tertiary butyl, pentyl, isoamyl, t-pentyl, neopentyl, propylethyl, isopropylethyl, or cyclopentyl;

(8) acyl group of the following formula:

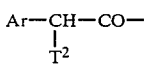

wherein Ar is as defined above and T$^2$ is one of (i), (ii), (iii) or (iv) below:

(i) hydroxy or C$_1$ to C$_{10}$ acyloxy e.g. formyloxy, acetoxy, propionyloxy, butyryloxy, valeryloxy, cyclopropylacetoxy, cyclopentylpropionyloxy, phenylacetoxy, thienylacetoxy, phenoxyacetoxy, glycolyloxy, glyoxalyloxy, glycyloxy, chloroacetoxy, bromoacetoxy, trifluoroacetoxy, benzoyloxy, methylbenzoyloxy, dimethylbenzoyloxy, nitrobenzoyloxy, methoxybenzoyloxy, cyanobenzoyloxy, methanesulfonylbenzyloxy, carbamoyloxy, methylcarbamoyloxy, ethylcarbamoyloxy, propylcarbamoyloxy, methoxycarbonyloxy, t-butoxycarbonyloxy, benzyloxycarbonyloxy, methoxybenzyloxycarbonyloxy, nitrobenzyloxycarbonyloxy, or like acyls;

(ii) carboxy or protected carboxy as is given later in the explanation of COB;

(iii) sulfo or C$_1$ to C$_5$ alkoxysulfonyl e.g. methoxysulfonyl, ethoxysulfonyl, propoxysulfonyl, butoxysulfonyl, cyclopropylmethoxysulfonyl, pentyloxysulfonyl, or cyclopropylethoxysulfonyl; or (iv) a group of the following formula:

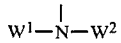

in which W$^1$ and W$^2$ each is hydrogen or a C$_1$ to C$_{10}$ aminosubstituent, for example, C$_2$ to C$_7$ alkoxycarbonyl e.g. methoxycarbonyl, ethoxycarbonyl, isopropoxycarbonyl, t-butoxycarbonyl, pentyloxycarbonyl, or methylhexylcarbonyl; C$_3$ to C$_{10}$ cycloalkyl-C$_2$ to C$_3$ alkoxycarbonyl e.g. cyclopropylmethoxycarbonyl, cyclopropylethoxycarbonyl, cyclopentylmethoxycarbonyl, cyclohexylethoxycarbonyl, or cycloheptylmethoxycarbonyl; C$_5$ to C$_8$ cycloalkoxycarbonyl e.g. cyclopentylcarbonyl, cyclohexylcarbonyl, cycloheptylcarbonyl, or cyclopropylcarbonyl; C$_1$ to C$_4$-alkylsulfonyl-C$_1$ to C$_4$-alkoxycarbonyl e.g. methanesulfonylethoxycarbonyl, ethanesulfonylethoxycarbonyl, methanesulfonylbutoxycarbonyl, or butanesulfonylbutoxycarbonyl; halo-C$_1$ to C$_3$-alkoxycarbonyl e.g. chloromethoxycarbonyl, chloroethoxycarbonyl, bromoethoxycarbonyl, iodoethoxycarbonyl, dichloroethoxycarbonyl, trichloroethoxycarbonyl, or trichloropropoxycarbonyl; aralkoxycarbonyl e.g. benzyloxycarbonyl, methylbenzyloxycarbonyl, dimethylbenzyloxycarbonyl, aminobenzyloxycarbonyl, acetamidobenzyloxycarbonyl, nitrobenzyloxycarbonyl, methoxybenzyloxycarbonyl, chlorobenzyloxycarbionyl, bromobenzyloxycarbonyl, diphenylmethoxycarbonyl, diphenylethoxycarbonyl, thiazolylmethoxycarbonyl, pyridylmethoxycarbonyl, or other Ar—CH$_2$O—CO— group (in which Ar is as defined above); C$_1$ to C$_{10}$ alkanoyl e.g. formyl, acetyl, propionyl, butyryl, isobutyryl, valeryl, isovaleryl, t-valeryl, hexanoyl, heptanoyl, cyclohexanocarbonyl, octanyl, cyclopentanepropionyl, or decanoyl; aromatic acyl of the formula Ar—CO— in which Ar is as given above; or other acyl group including pyronecarbonyl, thiopyronecarbonyl, pyridonecarbonyl, carbamoyl, guanidylcarbonyl, ureidocarbonyl, methylimidazolidonecarbonyl, methanesulfonylimidazolidonecarbonyl, methyldioxopiperazin-1-ylcarbonyl, ethyldioxopiperazin-1-ylcarbonyl, and butyldioxopiperazin-1-ylcarbonyl;

combined together show an enamino or equivalent Schiff base group derived from the amine, having amino for T$^2$ above, and an enolizable carbonyl compound, for example, C$_5$ to C$_{10}$ acetoacetates e.g. methyl, ethyl, propyl, butyl, isobutyl, or pentyl esters of acetoacetic acid, C$_5$ to C$_{10}$ acetoacetamides e.g. amide, methylamide, anilide, or methylanilide of acetoacetic acid, acetylacetone, acetoacetonitrile, α-acetylbutyrolactone, or 1,3-cyclopentanedione; or

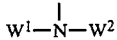

combined together show a diacylamino derived from a $C_4$ to $C_{10}$ dibasic acid e.g. succinimido, maleimido, or phthalimido;

(9) 5-aminoadipoyl; 5-aminoadipoyl protected at the amino group with e.g. $C_1$ to $C_{10}$ alkanoyl, aroyl, aralkanoyl, haloalkanoyl, or alkoxycarbonyl as defined hereinabove; or 5-aminoadipoyl protected at the carboxy group with e.g. alkyl, aryl, aralkyl, or alkylsilyl as defined hereinbefore; or

(10) acyl group of the following formula:

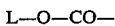

wherein L is an easily removable and optionally substituted $C_1$ to $C_{10}$ hydrocarbyl group e.g. t-butyl, 1,1-dimethylpropyl, cyclopropylmethyl, cyclopropylethyl, 1-methylcyclohexyl, isobornyl, 2-methoxy-t-butyl, 2,2,2-trichloroethyl, benzyl, naphthylmethyl, p-methoxybenzyl, p-nitrobenzyl, or pyridylmethyl.

Alternatively, the amino substituent in the group A can be a diacyl group derived from a $C_4$ to $C_{10}$ polybasic carboxylic acid e.g. succinyl, maleoyl, phthaloyl, or pyridine-2,3-dicarbonyl.

Other possible amino substituents in the group A can be a $C_1$ to $C_{20}$ optionally substituted hydrocarbyl e.g. methyl, ethyl, t-butyl, trityl, methylidene, benzylidene, hydroxybenzylidene, α-halobenzylidene, α-methoxybenzylidene, α-ethoxybenzylidene, 1-methoxy-2-phenylethylidene, 3,5-di-t-butyl-4-hydroxybenzylidene, or o-hydroxybenzylidene; $C_3$ to $C_{10}$ organic silyl e.g. trimethylsilyl, dimethylmethoxysilyl, chlorodimethylsilyl, methyldimethoxysilyl, or methyl ethylenedioxysilyl; or $C_1$ to $C_{10}$ sulfenyl e.g. methylthio, phenylthio, or o-nitrophenylthio.

Groups convertible into amino or amido e.g. enamino, amido, azido, isocyanato or isocyano are also included in the scope of group A.

Included in the said definition, the group A can be a cyclic group e.g. 4-phenyl-2,2-dimethyl-5-oxoimidazolidin-1-yl, 4-p-hydroxyphenyl-2,2-dimethyl-3-nitroso-5-oxoimidazolidin-1-yl, 4-p-hydroxyphenyl-2-phenyl-5-oxoimidazolidin-1-yl, or 4-thienyl-5-oxoimidazolidin-1-yl.

The said group A, where possible, can be interrupted by a hetero atom in the skeleton or can be unsaturated, or can be substituted by, for example, halogen e.g. fluorine, chlorine, or bromine; a nitrogen function e.g. amino, hydrazinyl, azido, alkylamino, arylamino, acylamino, alkylideneamino, acylimino, imino, or nitro; oxygen function e.g. hydroxy, alkoxy, aralkoxy, aryloxy, acyloxy, or oxo; sulfur function e.g. mercapto, alkylthio, aralkylthio, arylthio, acylthio, thioxo, sulfo, sulfonyl, sulfinyl, alkoxysulfonyl, or aryloxysulfinyl; carbon function e.g. alkyl, alkenyl, aralkyl, aryl, carboxy, carbalkoxy, carbamoyl, alkanoyl, aroyl, aminoalkyl, aralkanoyl, or cyano; or phosphorus function e.g. phospho or phosphoroyl.

The group B is hydroxy when the group COB is a carboxy group.

Alternatively, the group B can be a carboxy-protecting group. Thus the group B can be an oxygen function, for example, $C_1$ to $C_{10}$ alkoxy e.g. methoxy, ethoxy, propoxy, isopropoxy, butoxy, t-butoxy, monohydroxy-t-butoxy, methoxy-t-butoxy, cyclopropylmethoxy, pentyloxy, isopentyloxy, cyclopropylethoxy, cyclopentyloxy, hexyloxy, cyclohexyloxy, octyloxy, or decyloxy; $C_1$ to $C_6$ haloalkoxy e.g. chloromethoxy, chloroethoxy, bromoethoxy, iodoethoxy, dichloropropoxy, trichloroethoxy, trichlorobutoxy, or dibromocyclohexyloxy; $C_3$ to $C_{10}$ acylalkoxy e.g. acetonyloxy, acetylethoxy, propionylmethoxy, phenacyloxy, chlorophenacyloxy, bromophenacyloxy, nitrophenacyloxy, or methylphenacyloxy; $C_3$ to $C_{10}$ alkoxyalkoxy e.g. methoxymethoxy, ethoxymethoxy, chloroethoxymethoxy, propoxyethoxy, butoxyethoxy, cyclohexyloxyethoxy, methoxyethoxymethoxy, butoxyethoxymethoxy, or octyloxyethoxy; $C_2$ to $C_{10}$ aminoalkoxy e.g. aminomethoxy, aminoethoxy, dimethylaminoethoxy, or ethylaminomethoxy; aryloxy e.g. phenoxy, chlorophenoxy, nitrophenoxy, naphthyloxy, pyridyloxy, indolyloxy, indanyloxy, or pentachlorophenoxy; aralkoxy e.g. benzyloxy, methylbenzyloxy, xylylmethoxy, chlorobenzyloxy, bromobenzyloxy, methoxybenzyloxy, ethoxybenzyloxy, nitrobenzyloxy, dibromobenzyloxy, phenethyloxy, phthalidyloxy, p-hydroxy-di-t-butylbenzyloxy, diphenylmethoxy, or trityloxy; $C_1$ to $C_{10}$ alkylsilyloxy e.g. trimethylsilyloxy, dimethylmethoxysilyloxy, chlorodimethylsilyloxy, or ethylenedioxymethylsilyloxy; or $C_1$ to $C_{10}$ alkylstannyloxy e.g. trimethylstannyloxy; to form an ester group; $C_1$ to $C_{10}$ organic or inorganic acyloxy e.g. acetoxy, propionyloxy, sulfonyloxy, sulfooxy, or chloratooxy; to form an anhydride group; or metaloxy of a group I, II, or III metal in the periodical table e.g. lithiooxy, sodio-oxy, potassio-oxy, or magnesio-oxy, or $C_1$ to $C_{15}$ hydrocarbylammoniooxy e.g. triethylammoniooxy, dicyclohexylammonio-oxy to form a salt group; a sulfur function, for example, $C_1$ to $C_{10}$ hydrocarbylthio or mercapto to form a thiol ester or thiocarboxylic acid group; a nitrogen function, for example, $C_1$ to $C_5$ alkylamino e.g. methylamino, ethylamino, propylamino, butyramino, or pentylamino; or di-$C_1$ to $C_5$-alkylamino e.g. dimethylamino, diethylamino, piperidyl, morpholin-1-yl, or methylmorpholin-1-yl to form an amide group; or hydrazinyl or azido group to form hydrazide or azide group.

Usually, the carboxy-protecting groups are removed during the synthesis to give the final objective compounds and wide variety of structure is feasible without affecting the final product and departing from this invention.

The nucleophilic group X can be every possible group being introduced at the methylene attached to the position 3 of cephem ring in place of the acetoxy group of cephalosporanic acid.

Typical examples of X include halo e.g. chloro or bromo; oxygen functions, for example, hydroxy, $C_1$ to $C_4$ alkanoyloxy e.g. formyloxy, acetoxy, propionyloxy, or butyryloxy; substituted $C_1$ to $C_4$ alkanoyloxy e.g. malonyloxy, succinoyloxy, cyanoacetoxy, glycyloxy, alanyloxy, glycolyloxy, glyoxylyloxy, phenoxyacetoxy, sulfopropionyloxy, chloroacetoxy, dichloroacetoxy, or trifluoroacetoxy; aroyloxy e.g. benzoyloxy or naphthoyloxy; carbonic acyloxy e.g. chloroformyloxy, methoxyformyloxy, trichloroethoxyformyloxy, cyclopropylmethoxyformyloxy, or methanesulfonylmethoxyformyloxy; $C_1$ to $C_6$ alkoxy e.g. methoxy, ethoxy, butoxy, sec-butoxy, cyclopropylmethoxy, or cyclohexyloxy; aralkoxy of the formula $Ar-CH_2O-$ (in which Ar is as defined above) e.g. benzyloxy, furfuryloxy, or naphthylmethoxy; aryloxy of the formula Ar—O— (in which Ar is as given above) e.g. phenoxy, naphthyloxy, or indanyloxy; sulfur functions, for example, mercapto, $C_1$ to $C_5$ alkanoylthio e.g. acetylthio, propionylthio, or butyrylthio; aroylthio e.g. benzoylthio or naphthoylthio; thiocarbamoylthio, methylthiocarbamoylthio; $C_1$ to $C_6$ alkylthio e.g. methylthio, ethylthio, propylthio, butylthio, cyclopropylmethylthio, or cyclopropylethylthio; aralkylthio e.g. benzylthio, picolylthio, or phenethylthio; or arylthio of the formula Ar—S— (in which Ar is as defined above) e.g. phenylthio, triazolylthio, thiadiazolylthio, oxadiazolylthio, or tetrazolylthio, each being unsubstituted or substituted by e.g. methyl, ethyl, hydroxymethyl, hydroxyethyl, carboxyethyl, carboxymethyl, sulfoethyl, dimethylaminoethyl, dimethylaminopentyl, or morpholinoethyl; or nitrogen functions e.g. amino, azido, hydrazinyl, acetylamino, methylamino, pyridinium, picolinium, 4-carboxypyridinium, carbamoylpyridinium, hydroxymethylpyridinium, carboxymethylpyridinium, or chloropyridinium.

Said leaving group Z can be an anionic part of a nucleophilic reagent. Typical examples of them include halo e.g. chloro, bromo, or iodo; hydroxy; or $C_1$ to $C_8$ carboxylic acyloxy e.g. acetoxy or trifluoroacetoxy; sulfonic acyloxy e.g. methanesulfonyloxy, ethanesulfonyloxy, toluenesulfonyloxy, or bromobenzenesulfonyloxy, arylthio e.g. phenylthio, arylsulfenyl e.g. phenylsulfenyl, arylselenyl, arylsulfinyl, or alkylsulfinyl.

The leaving group is removed during the synthesis to give the final objective compounds, and wide variety of structure is feasible without affecting on the final product to be produced and without departing from this invention.

When R, COB or Y is likely to be affected from undersirable change during the reaction, it may be protected in advance and deprotected afterwards at an optional stage.

The compounds of this invention are shown by the following formula:

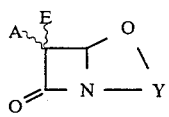

wherein
A is amino or substituted amino;
E is hydrogen or methoxy; and
Y is a divalent group of the following formula:

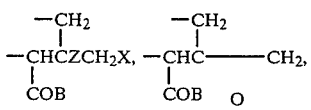

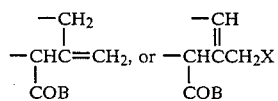

in which COB is carboxy or protected carboxy;
X is hydrogen or nucleophilic group; and
Z is a leaving group.
They include compounds of the following formula:

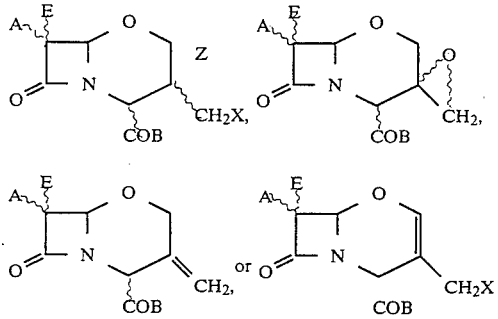

wherein A, E, COB, X, and Z are as defined above.
More specific compounds of them are those in which A is amino substituted by:
(1) $C_1$ to $C_{10}$ alkanoyl,
(2) $C_1$ to $C_7$ haloalkanoyl,
(3) azidoacetyl, cyanoacetyl, trifluoromethylthioacetyl, cyanomethylthioacetyl, or (4-pyridon-1-yl)acetyl;
(4) acyl group of the following formula:

wherein Ar is an aryl selected from furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, dihydrophenyl, tetrahydrophenyl, tetrahydropyrimidyl, naphthyl, benzothiazolyl, indolyl, quinolyl, isoquinolyl, benzopyrimidyl, cinnolinyl, pyridopyrimidyl, or indanyl ring group;
(5) acyl group of the following formula:

wherein Ar is as defined above and Q and Q′ each is hydrogen or methyl;
(6) acyl group of the following formula:

wherein Ar, Q, and Q′ each is as defined above and G is oxygen, sulfur, or imino;
(7) acyl group of the following formula:

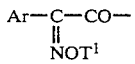

wherein Ar is as defined above and $T^1$ is hydrogen or $C_1$ to $C_6$ alkyl;
(8) acyl group of the following formula:

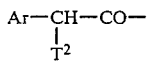

wherein Ar is as defined above and $T^2$ is one of (i) hydroxy or $C_1$ to $C_{10}$ acyloxy, (ii) carboxy or protected carboxy, (iii) sulfo or $C_1$ to $C_5$ alkoxysulfonyl, or a group of the formula:

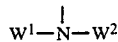

in which $W^1$ and $W^2$ each is hydrogen or a $C_1$ to $C_{15}$ amino-substituent;

(9) 5-aminoadipoyl. 5-aminoadipoyl protected at the amino or 5-aminoadipoyl protected at the carboxy;

(10) acyl group of the following formula:

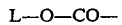

wherein L is an easily removable and unsubstituted or substituted $C_1$ to $C_{10}$ hydrocarbyl group; or

(11) $C_1$ to $C_{20}$ optionally substituted hydrocarbyl, $C_3$ to $C_{10}$ organic silyl, or $C_1$ to $C_{10}$ sulfenyl, the group B in said COB is $C_1$ to $C_{10}$ alkoxy, $C_1$ to $C_6$ haloalkoxy, $C_3$ to $C_{10}$ acylalkoxy, $C_3$ to $C_{10}$ alkoxyalkoxy, $C_2$ to $C_{10}$ aminoalkoxy, aryloxy, aralkoxy, $C_1$ to $C_{10}$ alkylsilyloxy, $C_1$ to $C_{10}$ alkylstannyloxy, $C_1$ to $C_{10}$ acyloxy, inorganic acyloxy, metal-oxy of a group I, II, or III metal in the periodical table, $C_1$ to $C_{15}$ hydrocarbylammonio-oxy, $C_1$ to $C_{10}$ hydrocarbylthio, mercapto, $C_1$ to $C_5$ alkylamino, di-$C_1$ to $C_5$ alkylamino, hydrazinyl, or azido, the group E is $\beta$-hydrogen or $\alpha$-methoxy; the group X is halo, hydroxy, $C_1$ to $C_4$ alkanoyloxy, substituted $C_1$ to $C_4$ alkanoyloxy, aroyloxy, carbonic acyloxy, $C_1$ to $C_6$ alkoxy, aralkoxy of the formula Ar—CH$_2$O— or aryloxy of the formula Ar—O— (in which Ar is as defined above), mercapto, $C_1$ to $C_5$ alkanoylthio, aroylthio, $C_1$ to $C_6$ alkylthio, aralkylthio of the formula Ar—CH$_2$S— or arylthio of the formula Ar—S— (in which Ar is as defined above), amino, azido, hydrazinyl, acetylamino, methylamino, pyridinium, picolinium, 4-carboxypyridinium, carbamoylpyridinium, hydroxymethylpyridinium, carboxymethylpyridinium, or chloropyridinium, and the group Z is halo, hydroxy or $C_1$ to $C_8$ alkanoyloxy, sulfonyloxy, arylthio, arylsulfenyl, arylselenyl, arylsulfinyl, or alkylsulfinyl.

Further specific compounds (I) have benzoylamino, methylbenzoylamino, chlorobenzoylamino, nitrobenzoylamino, cyanobenzoylamino, phenoxyacetamido, phenylacetamido, diphenylmethoxycarbonylphenylacetamido, or amino for the A group; hydroxy, benzyloxy, tolylmethoxy, chlorobenzyloxy, diphenylmethoxy, naphthylmethoxy, t-butoxy, or trimethylsilyloxy for B in COB; chloro, bromo, hydroxy, acetoxy, methanesulfonyloxy, methylthio, 1-m ethyltetrazol-5-ylthio, or hydrogen for the X group; and chloro, bromo, hydroxy, or acetoxy for the Z group.

Some of the specific compounds I are given below:
(1) compounds of the following formula:

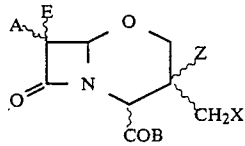

wherein
A=benzoylamino, COB=carboxy, E=$\beta$-hydrogen, and X=Z=chloro;
A=benzamido, COB=carboxy, E=$\beta$-hydrogen, and X=Z=bromine;
A=benzamido, COB=benzyloxycarbonyl, E=$\beta$-hydrogen, and X=Z=chlorine;
A=benzamido, COB=benzyloxycarbonyl, E=$\beta$-hydrogen, and X=Z=bromine;
A=benzamido, COB=diphenylmethoxycarbonyl, E=$\beta$-hydrogen, and X=hydrogen, and Z=hydroxy;
A=benzamido, COB=diphenylmethoxycarbonyl, E=$\beta$-hydrogen, X=hydrogen, and Z=$\alpha$-acetoxy;
A=benzamido, COB=diphenylmethoxycarbonyl, E=$\beta$-hydrogen, X=hydrogen, and Z=bromine;
A=benzamido, COB=diphenylmethoxycarbonyl, E=$\beta$-hydrogen, and X=Z=hydroxy;
A=benzamido, COB=diphenylmethoxycarbonyl, E=$\beta$-hydrogen, X=acetoxy, and Z=hydroxy;
A=benzamido, COB=diphenylmethoxycarbonyl, E=$\beta$-hydrogen, X=hydroxy, and Z=methanesulfonyloxy,
A=benzamido, COB=diphenylmethoxycarbonyl, E=$\beta$-hydrogen, X=chlorine, and Z=hydroxy;
A=benzamido, COB=diphenylmethoxycarbonyl, E=$\beta$-hydrogen, and X=Z=chlorine;
A=benzamido, COB=diphenylmethoxycarbonyl, E=$\beta$-hydrogen, X=methylthio, and Z=chlorine;
A=benzamido, COB=diphenylmethoxycarbonyl, E=$\beta$-hydrogen, X=1-methyltetrazolylthio, and Z=hydroxy;
A=benzamido, COB=diphenylmethoxycarbonyl, E=$\beta$-hydrogen, X=1-methyltetrazolylthio, and Z=chlorine;
A=benzamido, COB=diphenylmethoxycarbonyl, E=$\beta$-hydrogen, X=bromine, and Z=hydroxy;
A=benzamido, COB=diphenylmethoxycarbonyl, E=$\beta$-hydrogen, and X=Z=bromine;
A=p-methylbenzamido, COB=diphenylmethoxycarbonyl, E=$\beta$-hydrogen and X=Z=chlorine;
A=p-chlorobenzamido, COB=diphenylmethoxycarbonyl, E=$\beta$-hydrogen, and X=Z=chlorine;
A=p-cyanobenzamido, COB=diphenylmethoxycarbonyl, E=$\beta$-hydrogen, and X=Z=chlorine,
A=p-nitrobenzamido, COB=diphenylmethoxycarbonyl, E=$\beta$-hydrogen, and X=Z=chlorine;
A=phenoxyacetamido, COB=diphenylmethoxycarbonyl, E=$\beta$-hydrogen, and X=Z=chlorine;
A=phenylacetamido, COB=t-butoxycarbonyl, E=$\beta$-hydrogen, and X=Z=chlorine;
A=phenylacetamido, COB=benzyloxycarbonyl, E=$\beta$-hydrogen, and X=Z=chlorine;
A=benzamido, COB=carboxy, E=$\alpha$-methoxy, X=hydrogen, and Z=hydroxy;
A=benzamido, COB=carboxy, E=$\alpha$-methoxy, X=hydrogen, and Z=acetoxy;
A=benzamido, COB=carboxy, E=$\alpha$-methoxy, X=hydrogen, and Z=trifluoroacetoxy;
A=benzamido, COB=benzyloxycarbonyl, E=$\alpha$-methoxy, and X=Z=chlorine;
A=benzamido, COB=benzyloxycarbonyl, E=$\alpha$-methoxy, and X=Z=bromine;
A=benzamido, COB=diphenylmethoxycarbonyl, E=$\alpha$-methoxy, X=hydrogen, and Z=hydroxy;
A=benzamido, COB=diphenylmethoxycarbonyl, E=$\alpha$-methoxy, X=hydrogen, and Z=acetoxy;
A=benzamido, COB=diphenylmethoxycarbonyl, E=$\alpha$-methoxy, X=hydrogen, and Z=trifluoroacetoxy;
A=benzamido, COB=diphenylmethoxycarbonyl, E=$\alpha$-methoxy, and X=Z=chlorine;
A=benzamido, COB=diphenylmethoxycarbonyl, E=$\alpha$-methoxy, and X=Z=bromine;

A=p-chlorobenzamido, COB=diphenylmethoxycarbonyl, E=α-methoxy, X=1-methyltetrazolylthio, and X=chlorine;
A=p-cyanobenzamido, COB=diphenylmethoxycarbonyl, E=α-methoxy, X=1-methyltetrazolylthio, and Z=chlorine;
A=p-nitrobenzamido, COB=diphenylmethoxycarbonyl, E=α-methoxy, X=1-methyltetrazolylthio, and X=chlorine;
A=p-methylbenzamido, COB=diphenylmethoxycarbonyl, E=α-methoxy, X=1-methyltetrazolylthio, and Z=chlorine;
A=p-chlorobenzamido, COB=diphenylmethoxycarbonyl, E=α-methoxy, and X=Z=chlorine,
A=p-cyanobenzamido, COB=diphenylmethoxycarbonyl, E=α-methoxy, and X=Z=chlorine,
A=p-nitrobenzamido, COB=diphenylmethoxycarbonyl, E=α-methoxy, and X=Z=chlorine;
A=p-methoxybenzamido, COB=diphenylmethoxycarbonyl, E=α-methoxy, and X=Z=chlorine;
A=benzamido, COB=p-methylbenzyloxycarbonyl, E=α-methoxy, X=1-methyltetrazolylthio, and Z=chlorine;
A=benzamido, COB=p-chlorobenzyloxycarbonyl, E=α-methoxy, X=1-methyltetrazolylthio, and Z=chlorine;
A=benzamido, COB=naphthylmethoxycarbonyl, E=α-methoxy, X=1-methyltetrazolylthio, and Z=chlorine; or
A=α-diphenylmethoxycarbonyl-phenylacetamido, COB=diphenylmethoxycarbonyl, E=α-methoxy, and X=Z=chlorine.

Within this group of compounds there may be mentioned compounds of the formula:

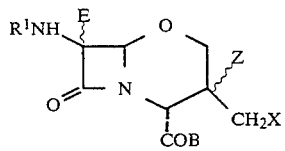

wherein
R¹ is carboxylic acyl;
B is a hydrogen or conventional carboxy protecting group;
E is β-hydrogen or α-methoxy;
X is hydrogen or a nucleophilic group; and
Z is a group of the formula RS(O)$_n$— or RSe(O)$_n$— in which R is $C_1$ to $C_3$ alkyl or monocyclic aryl and n is 0, 1 or 2.

(2) compound of the following formula:

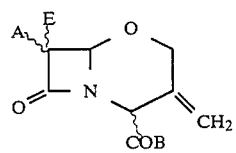

wherein
A=benzamido, COB=carboxy, E=β-hydrogen,;
A=benzamido, COB=diphenylmethoxycarbonyl, and E=β-hydrogen;
A=p-methylbenzamido, COB=diphenylmethoxycarbonyl, and E=β-hydrogen;
A=p-chlorobenzamido, COB=diphenylmethoxycarbonyl, and E=β-hydrogen;
A=p-cyanobenzamido, COB=diphenylmethoxycarbonyl, and E=β-hydrogen;
A=p-nitrobenzamido, COB=diphenylmethoxycarbonyl, and E=β-hydrogen;
A=benzamido, COB=benzyloxycarbonyl, and E=β-hydrogen;
A=phenoxyacetamido, COB=diphenylmethoxycarbonyl, and E=β-hydrogen;
A=phenylacetamido, COB=t-butoxycarbonyl, and E=β-hydrogen;
A=phenylacetamido, COB=benzyloxycarbonyl, and E=β-hydrogen;
A=phenylacetamido, COB=diphenylmethoxycarbonyl, and E=β-hydrogen;
A=amino, COB=diphenylmethoxycarbonyl, and E=β-hydrogen;
A=benzamido, COB=diphenylmethoxycarbonyl, and E=α-methoxy;
A=phenylacetamido, COB=benzyloxycarbonyl, and E=α-methoxy;
A=amino, COB=diphenylmethoxycarbonyl, and E=α-methoxy; or
A=amino, COB=benzyloxycarbonyl, and E=α-methoxy.

(3) compounds of the following formula:

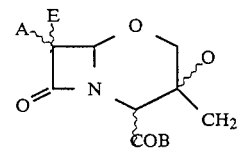

wherein
A=benzamido, COB=diphenylmethoxycarbonyl, and E=β-hydrogen.

(4) compounds of the following formula:

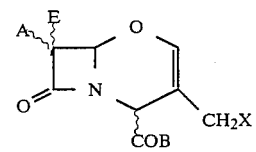

wherein
A=benzamido, COB=diphenylmethoxycarbonyl, E=β-hydrogen, and X=hydrogen.

Also contemplated within the scope of the present invention are compounds of the formula:

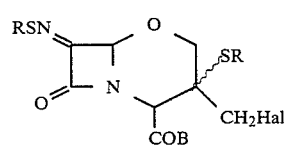

wherein
R is $C_1$ to $C_3$ alkyl or monocyclic aryl, e.g., phenyl,
B is hydrogen or a conventional carboxy protecting group, and
Hal is a halogen, e.g., chlorine.

These compounds can be prepared by acylating the corresponding 7-amino-3-exomethylene compound with a sulfenic halide RSHal followed by oxidation. After reduction of the 7-thioimino compound to the 7-thioamino compound (RSNH—) compound, such compound can be easily hydrolyzed with a base or acid in high yield to give the 7-amino compound. This provides a convenient protection procedure for the amino group.

II. USES OF THE COMPOUNDS

Compounds I can be used as starting materials for making known antibacterials e.g. 1-dethia-1-oxacephalosporins (Japanese Patent Publication (Unexamined) Nos. 49-133,594 and 51-149,295) in high yield by introducing or migrating a double bond to position 3, replacing A with an antibacterially preferable side chain, and/or deprotecting the protected carboxy in COB, if required after introduction of antibacterially suitable X at the methylene bound to position 3 of 1-dethia-1-oxacephem nucleus. Of course, said double bond, A, COB, and X may be replaced by antibacterially suitable ones prior to forming desired cephem ring system. Choice of said groups A, COB, and X in the starting materials and the intermediates depends mainly on easiness of reactions, stability under reaction conditions, and on the factors of waste, costs, or other practical and technical factors.

Compounds (1) can be, for example, subjected to (a) HZ-elimination to give a 1-dethia-1-oxacephalosporin (4) which can also be prepared by (b) double bond migration of Compound (2) with a base (e.g. triethylamine) at 0° C. to 70° C. for 5 hours to 3 days or by (c) cyclization of Compound (3) with a Lewis acid (e.g. boron trifluoride) at 0° C. to 50° C. for 0.1 to 1 hour. All of the processes (a), (b), and (c) can be effected under conditions analogous to the corresponding treatments given later in relation to the compounds of this invention. Some of illustrative examples are given below in the working examples.

R means a group of acyl (minus the carbonyl function) when A is an α-amino function represented by RCONH)

Compounds I (A=7β-amido; COB=COOH) or pharmaceutically acceptable salts thereof are moderately active antibacterials. They can be injected with a conventional carrier to a patient suffering from bacterial infection caused by sensitive gram positive bacteria (e.g. *Streptococcus pyogenes*) or gram negative bacteria (e.g. *Escherichia coli*) at a dose of 0.1 to 10 g per day.

III. PROCESSES

The said Compounds I are prepared in several synthetic routes as given below with reaction scheme:

(1) Cyclization

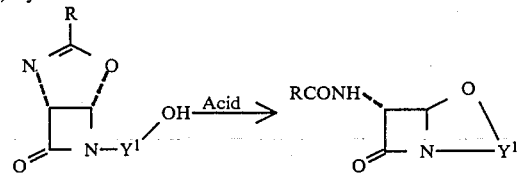

(2) Methoxylation

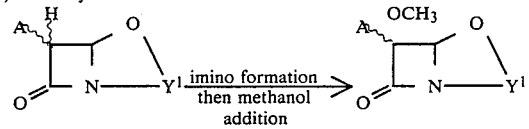

(3) Addition of XZ

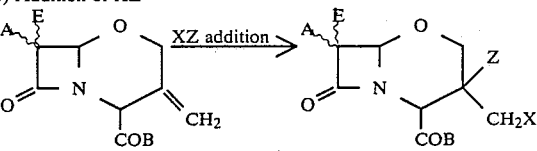

(4) Elimination of HZ

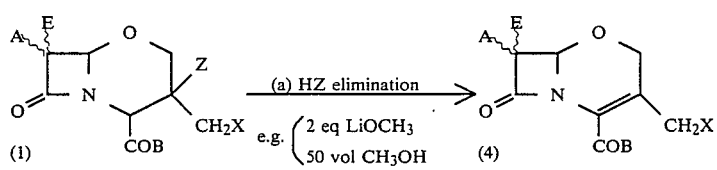

(b) double bond migration e.g. $\begin{pmatrix} 1\text{-}5 \text{ eq } N(C_2H_5)_3 \\ 50 \text{ vol. } CH_2Cl_2 \end{pmatrix}$

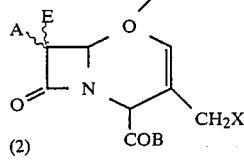

(c) cyclization (E = β-H)

e.g. $\begin{pmatrix} 0.05 \text{ eq } BF_3 \\ 30 \text{ vol. } CH_2Cl_2 \end{pmatrix}$

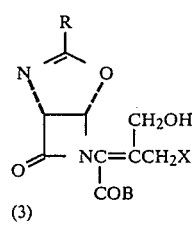

(wherein
A, COB, X and Z are as given above and

-continued

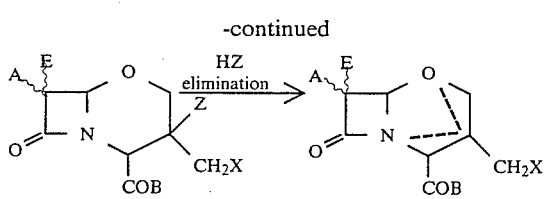

and (5) Other modification on the molecule.

In these reaction schemes, R, $Y^1$, A, E, COB, X and Z are as defined hereinbefore.

Detailed explanation of these processes are given below.

(1) Cyclization

Compounds Ia (wherein A is an α-RCONH and E is β-hydrogen) are preparable from the corresponding Oxazolinoazetidine II under the action of an acid according to the following reaction scheme:

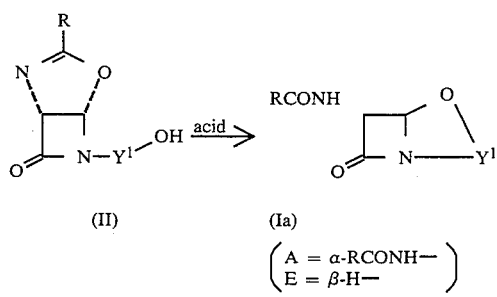

In the above formulas R is a monovalent group (minus the carbonyl function) from an acyl derived from a carboxylic or carbonic acid;

$Y^1$ is a divalent group of the following formula:

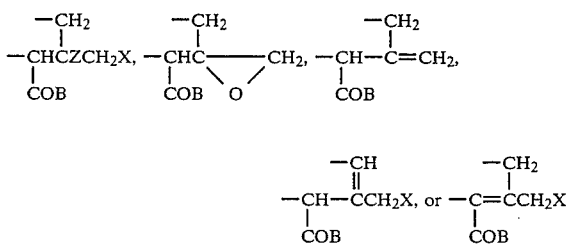

in which

COB is carboxy or protected carboxy;

X is hydrogen or a nucleophilic group; and

Z is a leaving group.

The group R corresponds to the monovalent group of acyl (minus the carbonyl function) derived from carboxylic or carbonic acyls as defined in the Section I Compounds.

Compounds Ia may be prepared from the corresponding Oxazolinoazetidines II by treating with an acid. Typical examples of the acid include mineral acids (e.g. HCl, HBr, $HNO_3$, $H_2SO_4$, or $H_3PO_4$), sulfonic acids (e.g. $CH_3SO_3H$, $C_2H_5SO_3H$, $C_6H_5SO_3H$, $CH_3C_6H_4SO_3H$, $BrC_6H_4SO_3H$, $CF_3SO_3H$, or naphthalenesulfonic acid) strong carboxylic acids (e.g. $Cl_3CCOOH$, $CF_3COOH$), Lewis acids (e.g. $BF_3$, $ZnCl_2$, $SnCl_2$, $SnCl_4$, $SnBr_2$, $SbCl_3$, $SbCl_5$, or $TiCl_3$), and similar acids.

The reaction is complete usually within 5 minutes to 10 hours, often 15 minutes to 3 hours at $-30°$ C. to $+50°$ C., especially at 15° C. to 30° C., to give Compounds Ia in high yield. If required, the reaction can be carried out with stirring or under an inert gas (e.g. nitrogen, argon, carbon dioxide) atmosphere.

The reaction is generally carried out in an inert solvent. Typical inert solvents include hydrocarbons (e.g. hexane, cyclohexane, benzene, toluene), halohydrocarbons (e.g. methylene chloride, chloroform, dichloroethane, carbon tetrachloride, chlorobenzene), ethers (e.g. diethyl ether, diisobutyl ether, dioxane, tetrahydrofuran), esters (e.g. ethyl acetate, butyl acetate, methyl benzoate), ketones (e.g. acetone, methyl ethyl ketone, cyclohexanone), sulfoxides (e.g. dimethyl sulfoxide), nitriles (e.g. acetonitrile, benzonitrile), and like solvents and mixtures thereof. Solvents having hydroxy function may react with the starting materials II to give by-products, but they also are available under controlled reaction conditions. Typical examples of such hydroxy-solvents are water, alcohols (e.g. methanol, ethanol, t-butanol, benzyl alcohols), acids (e.g., formic acid, acetic acid, propionic acid), and mixtures thereof.

The terminal hydroxy linked to $Y^1$ on Oxazolinoazetidine II may be protected in advance by a hydroxy-protecting group (e.g. formyl, tetrahydropyranyl, or the like) readily removable under the reaction conditions.

Occasionally, double bond migration, introduction of a nucleophile, elimination or like side reaction takes place during the reaction, but the side reactions can be also used intentionally for better procedures to be included in this invention.

In a typical example, an Oxazolinoazetidine II (one part) is dissolved in a mixture of 5 to 10 parts of halohydrocarbon (e.g. chloroform, dichloromethane), and 0 to 10 parts of ether solvent (e.g. ether, dioxane), mixed with 1 to 0.001 molar equivalent of an acid (e.g. boron trifluoride etherate, toluenesulfonic acid, copper sulfate, zinc chloride, stannic chloride), and the solution is kept at 10° to 60° C. for 0.5 to 10 hours to give the corresponding Compound Ia in about 50 to 95% yield.

Said Oxazolinoazetidines II are prepared from 6-epipenicillin 1-oxides e.g. according to the following reaction sequences:

Example I, No. 13 (1)

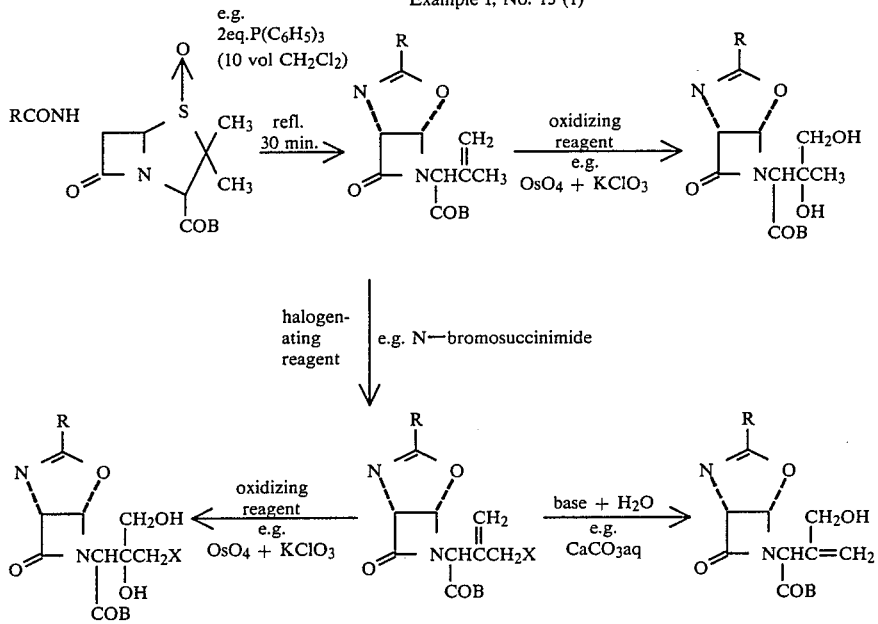

(wherein R, COB, and X are as defined above)

(2) Methoxylation

Transformation of said group E from hydrogen to methoxy in compounds Ia can be done stepwise as follows: at first, the part —NH— in the side chain A is oxidized to form an imino —N= on the corner at position 7, then equimolar methanol is added to the imino to reform another —NH— linkage and a methoxy in place of the original hydrogen.

When the A group is amino or amido, starting Compound Ia is treated with an N-halogenating reagent, subjected to hydrogen halide elimination with a base to give corresponding imino compound, and then treated with methanol to give the objective Compound Ia (where E is α-methoxy). By such an N-halogenation, other part of the molecule may be partially halogenated, but the over-halogenated product may be reduced to remove excessively introduced halogen atom. The procedures may be one of the followings:

(1) reaction of amine or amide with an N-halogenating reagent (e.g. molecular halogen, t-butyl hypochlorite), followed by the action of alkali metal methoxide (e.g. lithium methylate, sodium methylate, potassium methylate) or alkaline earth metal methoxide [e.g. Mg (OCH$_3$)$_2$, Ca(OCH$_3$)$_2$, Ba(OCH$_3$)$_2$ or like base] in methanol;

(2) reaction with t-butyl hypohalite and methanol in the presence of a base and phenyllithium, if required, with an additional solvent (e.g. tetrahydrofuran);

(3) the reaction with t-butyl hypohalite in the presence of sodium borate in methanol, and when an over-halogenated product if partially formed, the product is subjected to reduction with zinc, phosphite, or the like; and (4) successive treatments with bromine-DBU, phosphorus pentachloride-pyridine, base, methanolic base, and trialkylsilyl chloride or tetraalkylammonium chloride.

Alternatively, Compounds Ia(E=H, A=NH$_2$) can be treated with a suitable aldehyde (e.g. benzaldehyde, p-hydroxybenzaldehyde, 3,5-di-t-butyl-4-hydroxybenzaldehyde) to form a Schiff base, oxidized to give an imino compound, treated with methanol, and then hydrolyzed to give other Compounds Ia (E=OCH$_3$, A=NH$_2$).

In a typical example, 1 part of the amide Ia is dissolved in 10 to 50 parts of an inert solvent (e.g. dichloromethane, dioxan, ether, dipropyl ether, tetrahydrofuran), stirred with 1 to 5 mole equivalents of N-halogenating reagent (e.g. molecular halogen in carbon tetrachloride or t-butyl hypochlorite) for 2 to 10 minutes at $-70°$ C. to $-10°$ C., mixed with 1 to 4 equivalents of a metal methoxide (e.g. lithium methoxide, magnesium methoxide) in methanol, and stirred at $-50°$ C. to $0°$ C. for 5 to 70 minutes. The reaction mixture is neutralized with acetic acid or mineral acid, and the product is extracted with an organic solvent. Such a treatment gives usually up to 95% yield of objective Compound Ia(E=OCH$_3$).

(3) Addition

A compound I having an exomethylene group at position 3 reacts easily with an addition reagent XZ (e.g. molecular halogen, peracid, peroxide, hypohalite salt, hypohalite ester, heavy metal peroxide such as osmium tetroxide, sulfenyl halide) in an inert solvent (e.g. hydrocarbon, halohydrocarbon, ether, ester, or like solvents) to give newer Compounds I where Y is a divalent group of the formula:

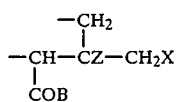

(in which COB, X, and Z are as defined above).

The addition may be accomplished smoothly even at low temperature of $-70°$ C. to $0°$ C. for 5 minutes to 10 hours in an inert solvent (especially halohydrocarbon and ether solvents) giving up to 90% yield of the addition product owing to high reactivity of exomethylene-double bond at position 3. When the reagent is a molecular halogen, the halogenation can be accelerated under the irradiation of light or the addition of a catalyst (e.g. Cu, Cu$_2$S, Cu$_2$Cl$_2$, Ph$_3$PO) to give a higher addition yield.

(4) Elimination to give 1-dethia-1-oxacephlosporins

This step is carried out by removing Z from the starting compound I along with a neighbouring hydrogen to give Δ$^2$- or Δ$^3$-cephem compounds. The double bond formation depends on the location of the eliminated hydrogen, but the isomerism may be also a result of migration of formerly formed double bond under the reaction condition or during work-up.

When the reactivity of Z is high enough, HZ is easily eliminated without any other reagent e.g. by keeping the Compund I at an elevated temperature.

When Z is halo (e.g. chloro, bromo, iodo) or acyloxy (e.g. mineral acid acyloxy, optionally substituted alkanoyloxy, carbamoyloxy, sulfonyloxy, phosphoryloxy), the elimination is accelerated by addition of an acid-acceptor (e.g. aliphatic amine, aromatic base; salt of weak organic acid and strong base; alkali metal hydroxide, bicarbonate, carbonate, mercaptide, or alcoholate; alkaline earth metal oxide, hydroxide, hydrogencarbonate, or carbonate; alumina, silica gel).

When Z is hydroxy, the elimination is accelerated by addition of a dehydrating reagent (e.g. phosphorus pentoxide, mineral acid, Lewis acid, striong carboxylic acid, aliphatic or aromatic sulfonic acid or phosphonic acid, inorganic or organic base, alumina, silica gel, amide), halogenating reagent (e.g. phosphorus pentahalide, phosphorus trihalide, phosphorus oxyhalide, thionyl halide, sulfuryl hlide), acylating reagent (e.g. acid anhydride, acid halide, acid isocyanide) or like reagent, if required in the presence of an acid-acceptor (e.g. said acid acceptor given above).

The reaction can be carried out at −50° C. to 100° C. with stirring under inert gas (e.g. nitrogen, argon, or carbon dioxide) in a solvent (e.g. said hydrocarbon, halohydrocarbon, ether, ester, ketone, alcohol, sulfoxide, or nitile solvent; base such as pyridine or quinoline; acid; acid anhydride such as acetic or trifluoroacetic anhydride; or like solvents or mixtures thereof).

(5) Other modifications

Compounds I are found to be the subject of other structural modifications conventional in the β-lactam chemistry (e.g. double bond migration with a base, protection and deprotection at the carboxy group for COB, protection and deprotection at the amino group for group A, introduction or replacement of group X with a nucleophilic reagent, or transformation of group X or Z within the given definition including acylation, hydrolysis, oxidation, or reduction, and like modifications) to give another Compound I, as are evidenced by working Examples described later.

The said reactions can be carried out in a hydrocarbon solvent (e.g. hexane, toluene), halohydrocarbon (e.g. dichloromethane, chlorobenzene), ether (e.g. diethyl ether, dioxane), ketone (e.g. acetone, cyclohexanone, benzophenone), ester (e.g. ethyl acetate, methyl benzoate), alcohol (e.g. ethanol, t-butanol, benzyl alcohol), amide, carboxylic acid, or other conventional solvents for organic reactions.

(Utilizing side reactions)

When the original molecule contains reactive groups, it may be occasionally attacked by the reagent or solvent during the said reaction or work-up. For example, addition of halogen to 3-exomethylene group accompanies N-halogenation in 7-amide chain; imino formation with a base for 7-methoxy introduction causes HZ elimination when Z is halo or acyloxy; and replacement of X being halo with basic nucleophilic reagent results in HZ elimination when Z is halo. These can be deemed usually as side-reactions, but when such side-reactions are used in the right direction more efficient synthesis can be done than conventional step-by-step reaction procedures.

Typical plans of such wise solutions are given in the working examples below. These multi-phase improvements should be included in the scope of this invention, allotting to each of the unit changes found in the molecule.

(Isolation and purification of the products)

Compounds I thus prepared by cyclization, methoxylation, addition, elimination, or other modifications can be isolated from the reaction mixture by removing the used solvent, unreacted materials, by-products, and like contaminants by concentration, extraction, washing, drying or like usual methods, and purified by reprecipitation, chromatography, crystallization, absorption, or like conventional purification. The stereoisomers at position 3 or 7 can be separated by careful chromatography, fractional recrystallization, or like conventional method. If desirable, stereoisomeric mixture may be subjected to reaction of next step of synthesis without separation.

IV. ADVANTAGES OF THE PROCESSES OVER PRIOR ART

The known method for preparing 1-dethia-1-oxacephalosporins starts from a penicillins (Japanese Patent Publication (Unexamined) No. 51-149295) by cleaving the thiazolidine ring, making azetidinone thiol naked, and rebinding new alcohol units to form azetidinooxazine bicycle. Another total synthesis (Japanese Patent Publication (Unexamined) No. 49-133594) requires more difficult intermolecular cyclization to form the dihydrooxazine ring. This invention aims at no carbon loss from starting penicillins, resulting in smoother intramolecular cyclization and less by-products, to give higher yield of expected Compound I and 1-dethia-1-oxacephalosporins.

Because of intermediacy of carbonium ion at position 4 in the starting azetidinone, prior art-methods result in the formation of an isomeric mixture of 4α and 4β ethers in around 1:1 ratio, followed by undesired loss of about a half of the ether product. This invention relates to stereoselective synthesis and is accompanied by practically none of such stereoisomers being lost.

As a result of the stereospecific reactions in high yield, products are readily crystallizable after simpler purification.

The following examples illustrate details of this invention, but they are not intended to limit the scope thereof.

The common nuclei and their numbering of compounds in the examples are shown as follows:

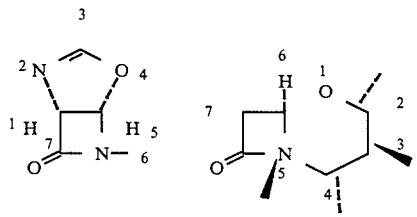

1βH,5βH-or (1R,5S)-7-oxo-4-oxa-1-dethia-1-oxacepham2,6-diazabicyclo[3.2.0]hept-2-ene.

The stereochemical relationship carbons 1 and 5 in the bicyclohept-2-ene is directly transfered to the configurations of carbons 6 and 5 in 6-epipenicillins or carbons 7 and 6 in oxacephams, respectively.

The stereochemistry around carbon 6 of 1-dethia-1-oxacepham ring system is identical with carbon 6 of cephalosporins at position 6.

Stereochemistry of COB in the formulae is preferably the same with that in penicillins (i.e. R configuration) but not necessarily restricted to it.

In the following Examples, experimental errors in IR-spectra are within ±10 cm$^{-1}$ and those in NMR spectra are within ±0.2 ppm. Melting points are uncorrected. Anhydrous sodium sulfate was used for drying every solution.

Physical constants of the products are summarized in Table VI.

I. CYCLIZATION

EXAMPLES I-1 TO 32

An Oxazolinoazetidine (II) is dissolved in a solvent and mixed with an acid to give an 1-dethia-1-oxacepham compound (I) under a condition shown in Table I.

Details of reaction No. 13 are given below to show typical experimental procedure of the cyclization.

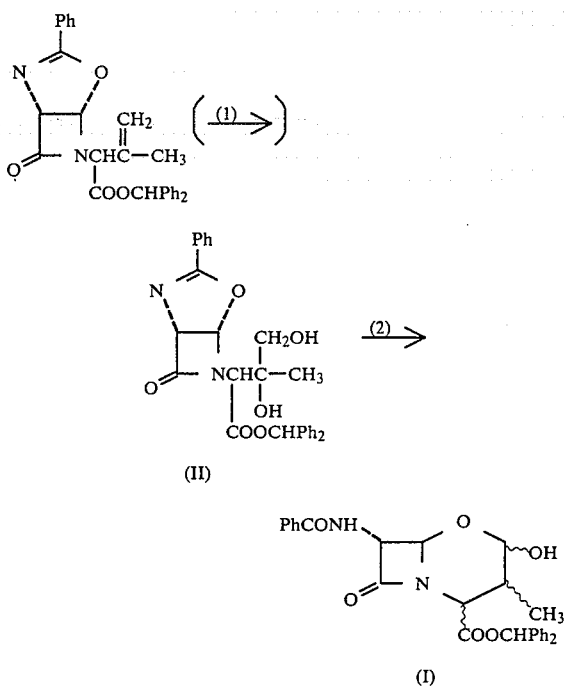

(1) A solution of diphenylmethyl 2-[(1R,5S)-3-phenyl-7-oxo-4-oxa-2,6-diazabicyclo[3.2.0]hept-2-en-6-yl]-2-isopropenylacetate (12.0 g), osmium tetroxide (1.0 g) and potassium chlorate (12.0 g) in a mixture of tetrahydrofuran (400 ml) and water (200 ml is stirred at 58° C. for 3.5 hours. After cooling, the reaction mixture is poured into ice-water and extracted with ethyl acetate. The extract is washed with brine, aqueous 10% sodium thiosulfate and then aqueous sodium hydrogencarbonate, dried and evaporated to yield diphenylmethyl 2-[(1R,5S)-3-phenyl-7-oxo-4-oxa-2,6-diazabicyclo[3.2.0-]hept-2-en-6-yl]-3,4-dihydroxy-3-methylbutyrate (12.88 g).

IR: $\nu_{max}^{CHCl_3}$ 3500br, 1770br, 1742, 1636 cm$^{-1}$.

(2) To a solution of the product (10.88 g) prepared above (1) in diethyl ether (300 ml) is added boron trifluoride etherate (75 μl), and the mixture is stirred for 3.5 hours at room temperature under nitrogen atmosphere, poured into cold aqueous sodium hydrogencarbonate, and extracted with ethyl acetate. The extract is washed with brine and evaporated. The residue is washed with a mixture of dichloromethane and ether to yield a mixture (15 g) of isomers at position 3 of diphenylmethyl 7α-benzamido-3ξ-methyl-3ξ-hydroxy-1-dethia-1-oxacepham-4α-carboxylate.

IR: $\nu_{max}^{CHCl_3}$ 3560, 3445, 1774, 1739, 1670 cm$^{-1}$.

The isomeric mixture is chromatographed on a column of silica gel deactivated with 10% water. Eluate with a mixture (4:1) of benzene and ethyl acetate is recrystallized from a mixture of acetone and ether and then a mixture of acetone and dichloromethane to give those respective two stereoisomers.

EXAMPLE I-33

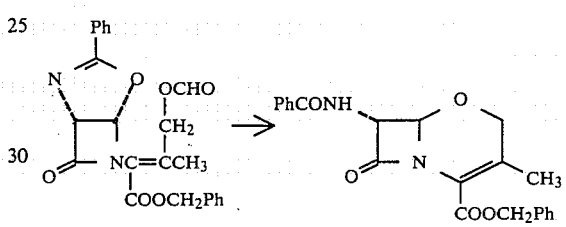

(a) To a solution of benzyl 2-[(1R,5S)-3-phenyl-7-oxo-4-oxa-2,6-diazabicyclo[3.2.0]hept-2-en-6-yl)]-3-formyloxymethyl-2-butenoate (54 mg) in methanol (2 ml) is added boron trifluoride etherate (19 μl) under cooling at −20° C., and the mixture stirred at −20° C. to 0° C. for 40 minutes, at 0° C. for 2 hours, and then at room temperature for 1 hour, mixed with aqueous 5% sodium hydrogencarbonate and extracted with dichloromethane. The extract is washed with water, dried, and evaporated. The residue is crystallized from methanol to afford benzyl 7α-benzamido-3-methyl-1-dethia-1-oxa-3-cephem-4-carboxylate (10 mg=20% yield).

mp. 208°–212° C.

(b) In a manner similar to the above but using trifluoromethanesulfonic acid (5 μl) for 130 minutes under ice-cooling or 0.38N hydrogen chloride in methanol (0.5 ml) for 3 hours, instead of boron trifluoride, the same product (14 mg or 5 mg) is also prepared (27.5% or 7% yield).

mp. 208°–212° C.

II. METHOXYLATION

EXAMPLES II-1 TO 24

A 7β-unsubstituted-7α-amido-1-dethia-1-oxacepham compound (I) is dissolved in a solvent, and mixed with an N-halogenating reagent and a base in methanol under a condition given in Table II to give the corresponding 7α-methoxy-7β-amido compound.

Details of reactions No. 5 and No. 9 are given below to show experimental procedure of the methoxylation.

(No. 5)

To a solution of diphenylmethyl 7α-benzamido-3α-hydroxy-3β-methyl-1-dethia-1-oxacepham-4α-carboxylate (486 mg) in anhydrous dichloromethane (20 ml) are added t-butyl hypochlorite (0.15 ml) and 2N solution of lithium methoxide in methanol (1.1 ml) at −50° C., and the mixture is stirred for 15 minutes, mixed with acetic acid (1.2 ml), stirred for 5 minutes, diluted with ice-cooled aqueous sodium hydrogencarbonate, and extracted with dichloromethane. The extract is washed with aqueous sodium hydrogen-carbonate and water, dried, and evaporated. The colorless foamy residue is purified by chromatography on silica gel to give diphenylmethyl 7β-benzamido-7α-methoxy-3α-hydroxy-3β-methyl-1-dethia-1-oxacepham-4α-carboxylate (250 mg=48% yield).

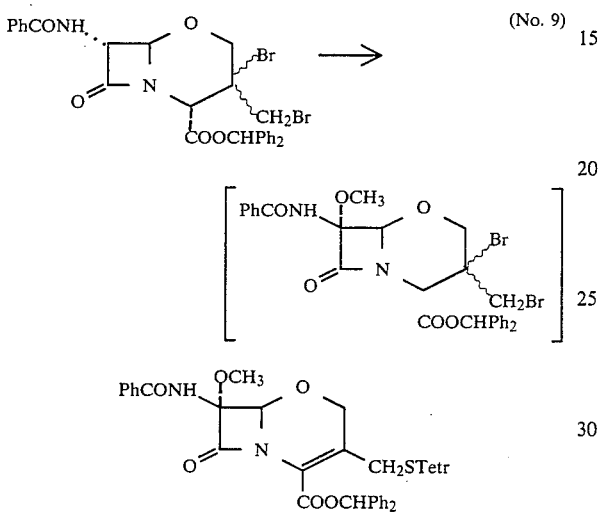

To a solution of diphenylmethyl 7α-benzamido-3ξ-bromo-3ξ-bromoethyl-1-dethia-1-oxacephem-4α-carboxylate (187 mg) in anhydrous dichloromethane (1 ml) are added t-butyl hypochlorite (46 μl) and 2M solution of lithium methylate in methanol (0.17 ml) at −30° C., and the mixture is stirred at the same temperature for 1 hour, mixed with a solution of sodium 1-methyltetrazol-5-ylmercaptide (100 mg) in acetone (1 ml) and stirred at room temperature for 1.5 hours. The reaction mixture is diluted with dichloromethane, washed with aqueous sodium hydrogencarbonate and brine, dried, and evaporated. The residue (180 mg) is chromatographed on a column of silica gel. Eluates with a mixture (1:1) of benzene and ethyl acetate give diphenylmethyl 7β-benzamido-7α-methoxy-3-(1-methyltetrazol-5-yl)thiomethyl-1-dethia-1-oxa-3-cephem-4-carboxylate (108 mg).

III. ADDITION

EXAMPLES III-1 TO 16

A 3,3-methylene-1-dethia-1-oxacepham compound (I) is dissolved in a solvent, mixed with an addition reagent XZ under conditions shown in Table III to give an addition product.

Details of those reactions No. 3, No. 4, and No. 15 are given below to show experimental procedure of the addition.

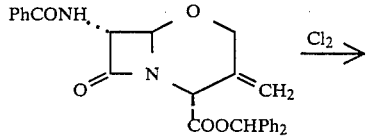

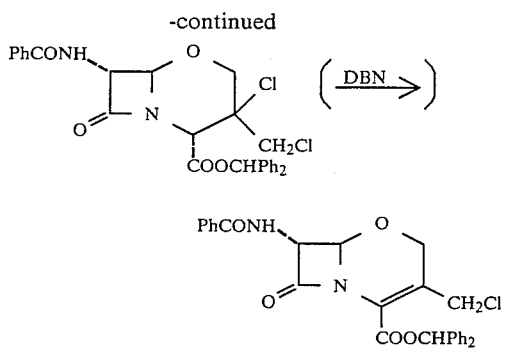

(No. 3)

To a solution of diphenylmethyl 7α-benzamido-3-exomethylene-1-dethia-1-oxacepham-4α-carboxylate (519 mg) in dichloromethane (5 ml) is added 0.76N solution of chlorine in carbon tetrachloride (1.6 ml), and the mixture is stirred under irradiation with a tungsten lamp at −20° to −30° C. for 40 minutes, mixed with 0.14 ml of cyclopentene, and stirred for 5 minutes.

The reaction mixture is stirred with 0.14 ml of 1,5-diazabicyclo[3.4.0]non-5-ene at −20° C. for 10 minutes, washed with dilute hydrochloric acid and water, dried, and evaporated. The crystalline residue is recrystallized from methanol to give diphenylmethyl 7α-benzamido-3-chloromethyl-1-dethia-1-oxa-3-cephem-4-carboxylate (484 mg=86% yield).

mp. 120°–128° C.

(No. 4)

To a solution of diphenylmethyl 7α-benzamido-3-methylene-1-dethia-1-oxacepham-4α-carboxylate (103 mg) in methylene chloride (1 ml) is added 0.75N solution of chlorine in carbon tetrachloride (0.3 ml), and the mixture is irradiated with tungsten lamp at −20° to −30° C. for 30 minutes, and evaporated under reduced pressure to give diphenylmethyl 7α-benzamido-3ξ-chloro-3ξ-chloromethyl-1-dethia-1-oxacepham-4α-carboxylate (120 mg).

(No. 15)

In a manner similar to the above, diphenylmethyl 7α-phenylacetamido-3-methylene-1-dethia-1-oxacepham-4α-carboxylate (705 mg) is reacted with 1.77 equivalents of chlorine in dichloromethane (7 ml) at a temperature below −25° C. to give diphenylmethyl 7α-phenylacetamido-3ξ-chloro-3ξ-chloromethyl-1-dethia-1-oxacepham-4α-carboxylate.

The latter is treated with piperidine (0.16 ml) at 15° C. for 40 minutes to yield diphenylmethyl 7α-phenylacetamido-3-chloromethyl-1-dethia-1-oxa-3-cephem-4-carboxylate (586 mg=78.4% yield). mp. 179°–182° C. (decomposition).

EXAMPLE III-17

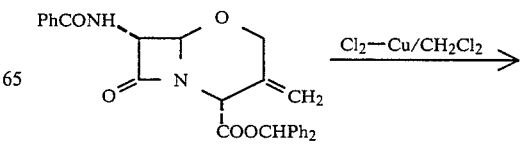

-continued

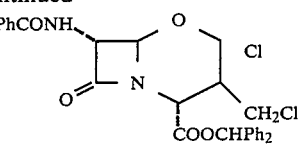

To a solution of diphenylmethyl 7α-benzamido-3-methylene-1-dethia-1-oxacepham-4α-carboxylate (1.405 g=3.0 mmoles) in dry dichloromethane (28 ml) cooled at −26° C. is added powdered copper (141 mg) with stirring under nitrogen atmosphere and the mixture is dropwise mixed with 1.2M solution of chlorine in chloroform (6.3 ml=2.5 equivalents) during 10 minutes, and stirred at −22° to −30° C. for 3 hours. The reaction mixture is mixed with an aqueous solution of sodium thiosulfate pentahydrate (2.98 g=4 equivalents), extracted twice with dichloromethane, washed with aqueous sodium hydrogencarbonate, washed twice with aqueous sodium chloride, dried over magnesium sulfate and evaporated. The residue is chromatographed over 190 g of silica gel and eluted with a mixture of benzene and ethyl acetate (3:1) to give colorless foamy diphenylmethyl 7α-benzamido-3α-chloro-3β-chloromethyl-1-dethia-1-oxacepham-4α-carboxylate (1.541 g=95.2% yield).

IV. ELIMINATION
EXAMPLE IV-1 TO 20

A 1-dethia-1-oxacepham compound is dissolved in a solvent and mixed with an eliminating reagent under conditions shown in Table IV to give a 1-dethia-1-oxacephem compound (I).

Details of reaction No. 12 are given below to show experimental procedure of the elimination.

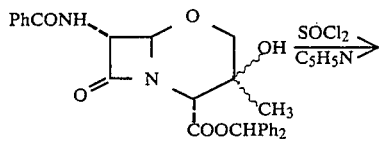

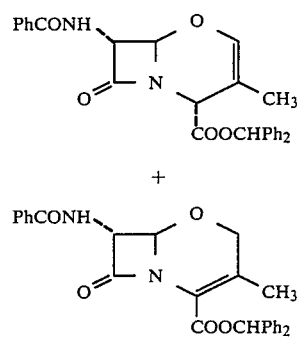

To a suspension of diphenylmethyl 7α-benzamido-3ξ-hydroxy-3ξ-methyl-1-oxadethiacepham-4α-carboxylate (15.0 g) in dichloromethane (100 ml) are added pyridine (6.8 ml) and thionyl chloride (3 ml) with stirring under ice-cooling, and the mixture is stirred for 7.25 hours at the same temperature and for 2.25 hours at room temperature, and poured into ice-water.

The organic layer is separated, washed with water, dried, and evaporated. The residue is chromatographed on silica gel (350 g) deactivated with 10% water. Eluate with a mixture (9:1) of benzene and ethyl acetate gives diphenylmethyl 7α-benzamido-3-methyl-1-dethia-1-oxa-3-cephem-4-carboxylate (2.65 g=25.2% yield)(mp. 144°–146° C.) and diphenylmethyl 7α-benzamido-3-methyl-1-dethia-1-oxa-2-cephem-4α-carboxylate (1.05 g=10.8% yield).

(IR: $\nu_{max}^{CHCl_3}$ 3440, 1782, 1745, 1676, 1663sh cm$^{-1}$).

V. CONTINUOUS PROCESS
EXAMPLE V-1 TO 8

A 7α-amino-7β-unsubstituted-3-exomethylene-1-dethia-1-oxacepham-4-carboxylate is dissolved in dichloromethane, mixed with a halogenating reagent and a base in methanol to give a 3-halo-3-halomethyl-7α-methoxy-7β-amino-1-dethia-1-oxa-3-cephem-4-carboxylate under conditions given in Table V. Occasionally, 3-halogenomethyl is replaced by another nucleophile.

Details of Example V-6 are given below to show experimental procedure of the continuous process of addition, methoxylation, and elimination.

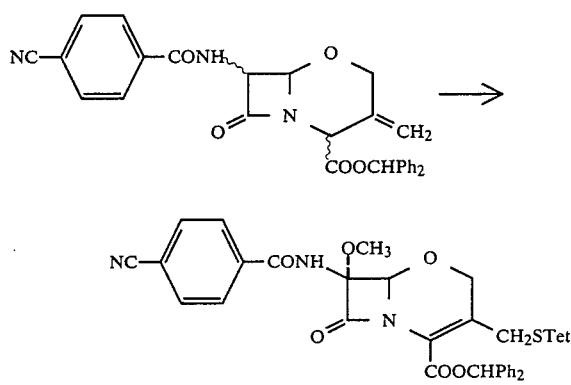

To a solution of diphenylmethyl 7α-p-cyanobenzamido-3-exomethylene-1-dethia-1-oxacepham-4α-carboxylate (246 mg) in dichloromethane (8 ml) cooled at −50° C. is added 1.2M solution of chlorine in carbon tetrachloride (1.47 ml) and the mixture is stirred under irradiation with 300 W tungsten lamp for 7 minutes. To the reaction mixture containing thus formed diphenylmethyl 7α-(N-chloro-p-cyanobenzamido)-3-exomethylene-1-dethia-1-oxacepham-4α-carboxylate 2M solution of lithium methoxide in methanol (1.57 ml) is added, and the whole mixture is cooled at −50° C. to −60° C. with stirring for 10 minutes, added acetic acid (0.2 ml), poured into ice-water, and extracted with dichloromethane. The extract is washed with dilute aqueous sodium hydrogen carbonate and water, dried, and evaporated to dryness. The residue contains diphenylmethyl 7α-cyanobenzamido-7α-methoxy-3-chloromethyl-1-dethia-1-oxa-3-cephem-4-carboxylate. It is dissolved in dichloromethane (6 ml) with stirring with sodium 1-methyltetrazol-5-mercaptide (100 mg) and tetrabutylammonium bromide (20 mg) in water (3 ml) at room temperature for 1 hour. The reaction mixture is poured into ice-water, extracted with dichloromethane, washed with water, dried, and evaporated to leave 335 mg of residue which gives purer 7β-p-cyanobenzamido-7α-methoxy-3-(1-methyltetrazol-5-ylthio)methyl-1-dethia-1-oxa-3-cephem-4-carboxylate (251 mg) after silica gel-column chromatography.

A. DOUBLE BOND MIGRATION

EXAMPLE A-1

To a solution of 7β-benazmido-7α-methoxy-3-methyl-1-dethia-1-oxa-2-cephem-4-carboxylic acid (100 mg) in acetone (10 ml) is added triethylamine (0.1 ml), and the mixture allowed to stand for 6 days. Spots of the reaction mixture on thin layer chromatogram correspond to those of 7β-benzamido-7α-methoxy-3-methyl-1-dethia-1-oxa-3-cephem-4-carboxylic acid and of the starting material.

EXAMPLE A-2

To a solution of diphenylmethyl 7α-benzamido-3,3-methylene-1-dethia-1-oxacepham-4α-carboxylate (5.0 g) in dichloromethane (25 ml) is added triethylamine (0.5 ml), and the mixture is stirred at room temperature for 80 minutes, concentrated after addition of small amount of benzene, and diluted with ether to give crystals of diphenylmethyl 7α-benzamido-3-methyl-1-dethia-1-oxa-3-cephem-4-carboxylate (4.5 g=90% yield).

The mixture is kept in equilibrium at room temperature for 15 hours to give 50.8% of $\Delta^2$-isomer, 4.1% of a mixture of $\Delta^2$ and $\Delta^3$-isomers, and 38.3% of $\Delta^3$-isomer after chromatographic separation.

EXAMPLE A-3

To a solution of 7α-benzamido-3,3-methylene-1-dethia-1-oxacepham-4α-carboxylic acid (100 mg) in acetone (10 ml) is added triethylamine (0.1 ml), and the mixture is allowed to stand for 5 days. Spots of the reaction mixture correspond to those of 7α-benzamido-3-methyl-1-dethia-1-oxa-2-cephem-4-carboxylic acid, 7α-benzamido-3-methyl-1-dethia-1-oxa-3-cephem-4-carboxylic acid, and the starting material.

B. REMOVAL OF CARBOXY-PROTECTING GROUP

EXAMPLE B-1

To a solution of diphenylmethyl 7β-benzamido-7α-methoxy-3α-methyl-3β-acetoxy-1-dethia-1-oxacepham-4α-carboxylate (960 mg) in anisole (4 ml) is added trifluoroacetic acid (10 ml) at 0° C., and the mixture is stirred for 15 minutes and evaporated under reduced pressure. The residue is solidified from a mixture of ether and n-hexane to yield 7β-benzamido-7α-methoxy-3α-methyl-3β-acetoxy-1-dethia-1-oxacepham-4α-carboxylic acid (470 mg) as colorless powder (70% yield).
mp. 203°–208° C. (decomposition).

In a similar manner, the following free carboxylic acids at position 4 are prepared from the corresponding diphenylmethyl esters.

7β-Benzamido-7α-methoxy-3α-hydroxy-3β-methyl-1-dethia-1-oxacepham-4α-carboxylic acid, mp. 100°–105° C. (decomposition).

7α-Benzamido-7α-methoxy-3α-trifluoroacetoxy-3β-methyl-1-dethia-1-oxacepham-4α-carboxylic acid, mp. 108°–113° C.

7β-Benzamido-7α-methoxy-3-methyl-1-dethia-1oxa-2-cephem-4-carboxylic acid, mp. 195°–198° C.
IR: $\nu_{max}^{KBr}$ 3250, 1766, 1742, 1642 cm$^{-1}$.

7α-Benzamido-3ξ-chloro-3ξ-chloromethyl-1-dethia-1-oxacepham-4α-carboxylic acid, mp. 118°–122° C. (decomposition).

EXAMPLE B-2

To a solution of diphenylmethyl 7α-benzamido-3-exomethylene-1-dethia-1-oxacepham-4α-carboxylate (1.125 g) in a mixture of dichloromethane (15 ml) and anisole (3.5 ml) is added dropwise a solution of aluminum trichloride (625 mg) in nitromethane (20 ml) at −20° C. with stirring, and the mixture is stirred at −10° to −20° C. for 30 minutes under nitrogen atmosphere. The reaction mixture is poured into ice-water containing hydrochloric acid and extracted with ethyl acetate. The extract solution is washed with saturated aqueous sodium hydrogen carbonate, and the washings are acidified with concentrated hydrochloric acid and reextracted with ethyl acetate. The organic layer is washed with water, dried and evaporated to leave 7α-benzamido-3-exomethylene-1-dethia-1-oxacepham-4α-carboxylic acid (623 mg).

Similarly, diphenylmethyl 7α-benzamido-3-methyl-1-dethia-1-oxa-2-cephem-4α-carboxylate (1.8 g) in dichloromethane (25 ml) is subjected to solvolysis with anisole (5.8 ml), aluminum trichloride (1.026 g), and nitromethane (36 ml) at −10° C. for 30 minutes to give 7α-benzamido-3-methyl-1-dethia-1-oxa-2-cephem-4α-carboxylic acid (935 mg=72.6% yield).

C. PROTECTION AND DEPROTECTION OF AMINO GROUP

EXAMPLE C-1

To a solution of diphenylmethyl 7α-amino-3-methylene-1-dethia-1-oxacepham-4α-carboxylate (25 mg) in dichloromethane (0.5 ml) are added pyridine (7 μl) and benzoyl chloride (10 μl) at −20° C. under nitrogen atmosphere, and the mixture is stirred for 1 hour, poured into ice-water, stirred for 5 minutes, and extracted with dichloromethane. The organic layer is separated, washed with water, aqueous sodium hydrogencarbonate and water, dried, and evaporated to give diphenylmethyl 7α-benzamido-3-methylene-1-dethia-1-oxacepham-4α-carboxylate (28 mg=86% yield). This product is identified with TLC and NMR techniques.

EXAMPLE C-2

To a solution of diphenylmethyl 7α-benzamido-3-methylene-1-dethia-1-oxacepham-4α-carboxylate (94 mg) in dichloromethane (4 ml) are added pyridine (32 μl) and a 0.37M solution of phosphorus pentachloride in dichloromethane (1.08 ml) at −40° C. under nitrogen atmosphere, and the mixture is warmed up to room temperature, stirred for 1 hour, cooled again to −40° C., mixed with methanol (8 ml), warmed up to 0° C., mixed with water (0.8 ml) and evaporated under reduced pressure. The residue is dissolved in ethyl acetate (20 ml) and washed with water. The solution is extracted with aqueous sodium hydrogencarbonate and water. The combined aqueous extract and washing are covered with ethyl acetate, adjusted to pH 7.0 and extracted with ethyl acetate. The organic layer is separated, washed with water, dried and evaporated to yield diphenylmethyl 7α-amino-3-methylene-1-dethia-1-oxacepham-4α-carboxylate (29 mg=40% yield).
IR: $\nu_{max}^{CHCl_3}$ 3000, 1770 sh, 1760, 1740 cm$^{-1}$.

D. REPLACEMENT AND TRANSFORMATION OF X AND Z

EXAMPLE D-1

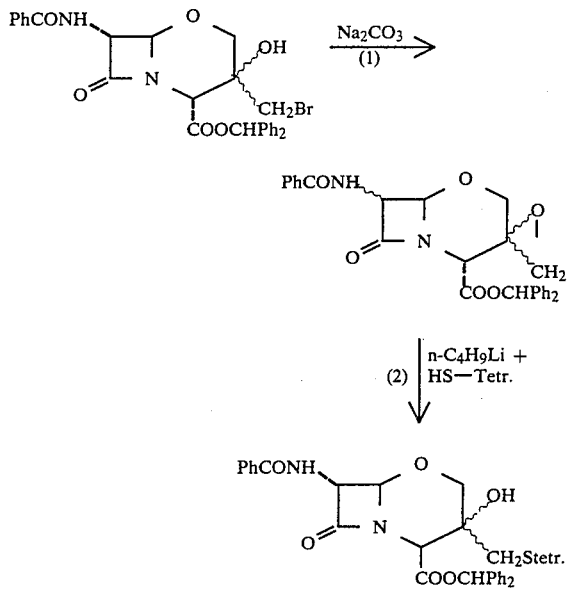

(1) To a solution of diphenylmethyl 7α-benzamido-3ξ-hydroxy-3ξ-bromomethyl-1dethia-1-oxacepham-4α-carboxylate (108 mg) in acetone (5 ml) containing 10% water is added potassium carbonate (50 mg), and the mixture is stirred at room temperature for 1.5 hours, diluted with brine, and extracted with dichloromethane. The extract is dried over magnesium sulfate and evaporated. The residue (90 mg) is purified by thin-layer chromatography on silica gel plate (solvent system: benzene+ethyl acetate (2:1)) to afford diphenylmethyl 7α-benzamido-3,3-epoxymethano-1-dethia-1-oxacepham-4α-carboxylate (40 mg) (isomer A). Another stereoisomer B at position 3 (56 mg) is obtained from the stereosiomeric starting material (140 mg).

(2) To a solution of 1-methyltetrazol-5-ylthiol (20 mg) in tetrahydrofuran (2 ml) is added a 1.5M-solution of n-butyl lithium in hexane (0.05 ml), and the mixture is stirred for 30 minutes, mixed with a solution of diphenylmethyl 7α-benzamido-3,3-epoxymethano-1-dethia-1-oxacepham-4α-carboxylate (56 mg) (epimer B) in tetrahydrofuran (1 ml), stirred for 1 hour, mixed with aqueous sodium hydrogencarbonate, and extracted with ethyl acetate. The extract is washed with brine, dried over magnesium sulfate, and evaporated. The residue is chromatographed on a column of silica gel (1 g) deactivated with 10% water. Eluate with a mixture (9:1) of benzene and ethyl acetate gives diphenylmethyl 7α-benzamido-3-(1-methyltetrazol-5-yl)thiomethyl-3-hydroxy-1-dethia-1-oxacepham-4α-carboxylate (43 mg) (epimer B).

EXAMPLE D-2

(1) To a solution of diphenylmethyl 7α-benzamido-3α-hydroxy-3β-methyl-1-dethia-1-oxacepham-4-carboxylate (100 mg) in isopropenyl acetate (5 ml) is added p-toluenesulfonic acid-monohydrate, (6 mg), and the mixture is heated to 60° C. for 75 minutes. After cooling, the reaction mixture is poured into icy dilute aqueous sodium hydrogencarbonate and extracted with dichloromethane. The organic layer is separated, washed with water, dried and evaporated to give diphenylmethyl 7α-benzamido-3α-acetoxy-3β-methyl-1-dethia-1-oxacepham-4α-carboxylate (30.5% yield).

(2) The same starting material as in (1) can be treated with a mixture of 1.1 equivalents of lithium diisopropylamide, 1.2 equivalents of acetyl chloride, and 20 parts by volume of tetrahydrofuran at −40° C. for 45 minutes, at −20° C. for 15 minutes, and then at 0° C. for 20 minutes or with 1 equivalent of pyridine and 1.2 equivalents of acetyl chloride in dichloromethane to give the same product.

(3) To a solution of diphenylmethyl 7β-benzamido-7α-methoxy-3α-hydroxy-3β-methyl-1-dethia-1-oxacepham-4α-carboxylate (52 mg) in dioxane (1 ml) is added trifluoroacetic acid anhydride (0.1 ml) under nitrogen atmosphere under ice-cooling, and the mixture is kept at room temperature for 2 hours, mixed with water (0.3 ml), stirred for 30 minutes, diluted with ice-water, and extracted with ethyl acetate. The extract is washed with water, dried, and evaporated to yield oily diphenylmethyl 7β-benzamido-7α-methoxy-3α-trifluoroacetoxy-3β-methyl-1-dethia-1-oxacepham-4α-carboxylate (64 mg).

(4) A solution of diphenylmethyl 7α-benzamido-3ξ-hydroxy-3ξ-hydroxymethyl-1-dethia-1-oxacepham-4α-carboxylate (112 mg) in a mixture of pyridine (0.5 ml) and acetic anhydride (0.3 ml) is kept at 0° C. overnight. The mixture is concentrated in vacuo, poured into ice water, and extracted with ethyl acetate. The extract is washed with water, dilute hydrochloric acid, aqueous sodium hydrogen carbonate, and water, dried, and concentrated to give diphenylmethyl 7α-benzamido-3ξ-hydroxy-3ξ-acetoxymethyl-1-dethia-1-oxacepham-4α-carboxylate (54 mg) as crystals melting at 118° to 120° C.

(5) To a solution of diphenylmethyl 7α-benzamido-3ξ-hydroxy-3ξ-hydroxymethyl-1-dethia-1-oxacepham-4α-carboxylate (350 mg) in dichloromethane (3 ml) are added pyridine (78 μl) and methanesulfonyl chloride (75 μl), and the mixture is stirred at 0° C. for 1 hour and at room temperature for 3 hours. The reaction mixture is poured into ice-water, and extracted with ethyl acetate. The extract is washed with water, aqueous sodium hydrogencarbonate, and water, dried, and evaporated to residue (370 mg) giving diphenylmethyl 7α-benzamido-3ξ-hydroxy-3ξ-methanesulfonyloxymethyl-1-dethia-1-oxacepham-4α-carboxylate (145 mg) after silica gel chromatography.

REFERENCE EXAMPLES

Preparation of the starting material (1)

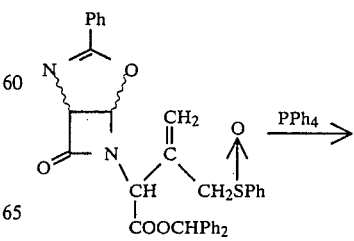

(a)

-continued

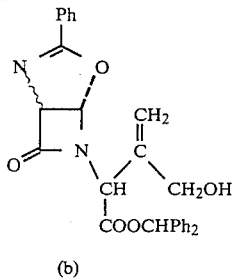

(b)

To a solution of Compound (a) (512 mg) in a mixture of benzene (10 ml) and methanol (1 ml) is added triphenylphosphine (0.4 g), and the mixture stirred at 65° C. for 1.5 hours. The residue is chromatographed on a column of silica gel (30 g) deactivated with 10% water. Eluate with benzene containing 20–30% acetic acid yields 202 mg of Compound (b).

IR: $\nu_{max}^{CHCl_3}$ 3370, 1782, 1755, 1635 cm$^{-1}$.

NMR: $\delta^{CDCl_3}$ 2.50–3.35m1H, 4.18s2H, 5.08s1H, 5.22s1H, 5.28d(3 Hz)1H, 5.50s1H, 6.08d(3 Hz)1H, 6.93s1H, 7.20–8.00m15H.

Preparation of the starting material (2)

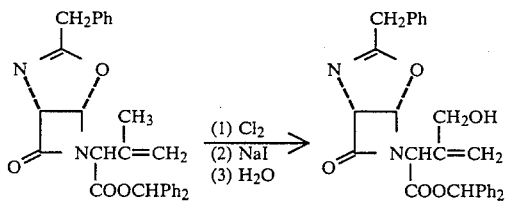

(Step 1) To a solution of diphenylmethyl 2-(3-benzyl-7-oxo-2,6-diaza-4-oxabicyclo[3.2.0]hept-2-en-6-yl)-3-methyl-3-butenoate (4.6 g) in ethyl acetate (70 ml) are added 2.74M-solution of hydrochloric acid in ethyl acetate (3.8 ml) and 1.47M-solution of chlorine in carbon tetrachloride (12 ml), and the mixture is stirred at room temperature for 15 minutes. Then, aqueous 5% sodium thiosulfate (80 ml), sodium hydrogencarbonate (3.4 g) and acetone (240 g) are added in the reaction mixture, and the combined solution is kept at room temperature for 2.5 hours. The product is isolated by extracting with ethyl acetate, drying over sodium sulfate, and evaporating to yield diphenylmethyl 2-(3-benzyl-7-oxo-2,6-diaza-4-oxabicyclo[3.2.0]hept-2-en-6-yl)-3-chloromethyl-3-butenoate (3.33 g), mp. 82°–83° C.

(Step 2) The butenoate above is dissolved in acetone (25 ml), mixed with sodium iodide (3.3 g) and kept at room temperature for 2 hours. The reaction mixture is concentrated to remove acetone and extracted with ethyl acetate. The extract is washed with aqueous 5% sodium thiosulfate and water, dried over sodium sulfate, and evaporated to leave the corresponding iodide (3.0 g).

(Step 3) To a solution of the iodide above (1.59 g) in a mixture of dimethyl sulfoxide (13 ml) and water (3 ml) is added cupric oxide (0.77 g), and the mixture is stirred at 39° C. for 1 hour. The reaction mixture is filtered to remove solid part and extracted with ethyl acetate. The extract solution is washed with water, dried over sodium sulfate, and evaporated to give diphenylmethyl 2-(3-benzyl-7-oxo-2,6-diaza-4-oxabicyclo[3.2.0]hept-2-en-6-yl)-3-hydroxymethyl-3-butenoate (0.35 g), mp. 40°–55° C.

| Explanation of abbreviations in Tables |
|---|
| —Ph = phenyl |
| —STetr = 1-methyl-1,2,3,4-tetrazol-5-yl |
| —C$_6$H$_4$NO$_2$—p = p-nitrophenyl |
| —C$_6$H$_4$CH$_3$—p = p-tolyl |
| —C$_6$H$_4$CN-p = p-cyanophenyl |
| —C$_6$H$_4$Cl—p = p-chlorophenyl |
| —Bu—t = tertiary butyl |
| —OAc = acetoxy |
| ===== between X and Z = CH$_2$X and Z taken together represent methylene |
| —O— between X and Z = X and Z represent epoxy. |
| A = amino or substituted amino in place of R$^1$CONH |
| Wt = weight of the starting material |
| =CH$_2$ = weight of the starting 3-exomethylene compound |
| EtOAc = ethyl acetate |
| THF = tetrahydrofuran |
| DMF = N,N—dimethylformamide |
| c-H$_2$SO$_4$ = concentrated H$_2$SO$_4$ |
| Et$_2$O = diethyl ether |
| t-BuOCl = tertiary butyl hypochlorite |
| eq = equivalent |
| DBN = 1,5-diazabicyclo[3.4.0]nonene-5 |
| (CH$_2$)$_5$NH = piperidine |
| Temp = reaction temperature |
| rt = room temperature |
| reflux = reflux temperature |
| hr = hour |
| hν = light irradiation |
| Δ$^2$ or Δ$^3$ for Z = a double bond at 2(3) or 3(4) present instead of leaving group at position 3. |

TABLE I

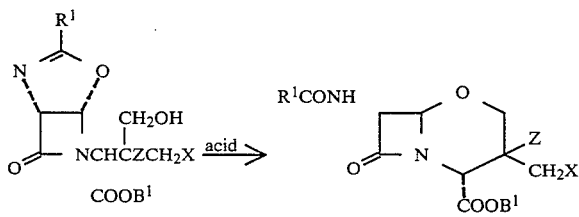

| No. | R$^1$ | B$^1$ | X | Z | Wt (mg) | Solvent (ml) | Acid (μl) | Temp (°C.) | Time (hr) | Yield mg | Yield % | Note |
|---|---|---|---|---|---|---|---|---|---|---|---|---|
| | | | | Cyclization (1) | | | | | | | | |
| 1. | —Ph | —CHPh$_2$ | — | | 50 | EtOAc(2.3) | CF$_3$SO$_3$H(0.35) | rt | 7/4 | — | >80 | |
| 2. | " | " | " | | 50 | EtOAc(2.4) | CH$_3$SO$_3$H(0.35) | " | 2 | — | ~10 | |
| 3. | " | " | " | | 50 | THF(4) | c-H$_2$SO$_4$(0.5) | " | 1 | — | ≦70 | |
| 4. | " | " | " | | 50 | C$_6$H$_6$(4) | c-H$_2$SO$_4$(0.05) | " | 1 | — | 30 | |
| 5. | " | " | " | | 50 | CH$_2$Cl$_2$(2) | SiO$_2$(100 mg) HClO$_4$(2) | " | 3 | — | 70 | |
| 6. | " | " | " | | 50 | CH$_2$Cl$_2$(2) | Amberlyst 15 | " | 1 | — | 60 | |

TABLE I-continued $$\underset{\substack{\text{COOB}^1}}{\overset{\substack{R^1\\|\\N\\\|}}{\underset{O}{\bigsqcup}}}\overset{\text{CH}_2\text{OH}}{\underset{\text{NCHCZCH}_2\text{X}}{|}} \xrightarrow{\text{acid}} \underset{\substack{\overset{|}{\text{COOB}^1}}}{\overset{R^1\text{CONH}}{\underset{O}{\bigsqcup}}\underset{N}{\overset{O}{\bigsqcup}}}\underset{\text{CH}_2\text{X}}{\overset{Z}{|}}$$

| No. | R¹ | B¹ | X | Z | Wt (mg) | Solvent (ml) | Acid (μl) | Temp (°C.) | Time (hr) | Yield mg | Yield % | Note |
|---|---|---|---|---|---|---|---|---|---|---|---|---|
| 7. | " | " | " | " | 50 | THF(2) | SiO₂(100 mg) H₃PO₄(2) | " | 15 | — | 70 | |
| 8. | " | " | " | " | 37 | CH₂Cl₂(1) | BF₃Et₂O(4) | " | 2 | 13 | 35 | |
| 9. | " | " | " | O | 97 | CH₂Cl₂(1) | BF₃Et₂O(10) | " | 0.5 | 48 | 50 | |
| 10. | " | " | —Cl | —OH | 293 | CH₂Cl₂(4) | BF₃Et₂O(1) | 5 | ¼ | 266 | 89 | stereo- isomers mixture |
| 11. | " | " | —STetr. | " | 186 | CH₂Cl₂(3.5) Et₂O(6.4) | BF₃Et₂O(4) | rt | 2.75 | 175 | 94 | stereo- isomers mixture |
| 12. | " | " | —H | —Br | 100 | CH₂Cl₂(5) | BF₃Et₂O(1) | " | 3 | 84 | 84 | |
| 13. | " | " | —OH | —OH | 10880 | Et₂O(300) | BF₃Et₂O(75) | " | 3.5 | 15 (g) | — | crude |
| 14. | " | " | —H | " | 15900 | CH₂Cl₂(100) Et₂O(210) | BF₃Et₂O(100) | " | 3 | 11.15 (g) | 70 | two stereo- isomers isolated |
| 15. | " | " | " | " | 200 | CH₂Cl₂(8) | CH₃C₆H₄SO₃H (5 mg) | " | 2 | 110 | 55 | two stereo- isomers isolated |
| 16. | " | " | —Br | " | 50 | CHCl₃(4) | BF₃Et₂O(1) | " | 3 | 11 | 32 | stereo- isomer |
| 17. | " | " | " | " | 88 | CHCl₃(4) | BF₃Et₂O(1) | " | 3 | 24 | 27 | |
| Cyclization (2) | | | | | | | | | | | | |
| 18. | —C₆H₄NO₂—p | —CHPh₂ | — | | 452 | EtOAc(2.5) CH₂Cl₂(2.5) | BF₃Et₂O(5) | rt | 1 | 423 | 102 | |
| 19. | —C₆H₄CH₃—p | " | | " | 491 | EtOAc(10) | BF₃Et₂O(6.3) | " | 1.5 | 299 | 62 | |
| 20. | —C₆H₄CN—p | " | | " | 101 | EtOAc(2) | BF₃Et₂O(1) | " | ¾ | 47 | 47 | |
| 21. | —C₆H₄Cl—p | " | | " | 116 | EtOAc(2) | BF₃Et₂O(1) | " | 1 | 104 | 90 | |
| 22. | —CH₂Ph | —Bu—t | | " | 1371 | EtOAc(16) CH₂Cl₂(15) | BF₃Et₂O(23) | " | 4/3 | 1019 | 74 | |
| 23. | " | " | | " | 732 | EtOAc(7) | BF₃Et₂O(13) | reflux | ¾ | 411 | 56 | |
| 24. | " | —CHPh₂ | | " | 1180 | CH₂Cl₂(12) | CuSO₄(1.2 g) | " | 1 | 1030 | 90 | |
| 25. | " | —CH₂Ph | | " | 155 | EtOAc(1.8) | 0.1M BF₃Et₂O/ EtOAc(300) | rt | 7/6 | 88 | 72 | |
| 26. | " | " | | " | 81 | EtOAc(1.2) | SnCl₄(400) | " | 3 | 25 | 31 | |
| 27. | " | " | | " | 4030 | EtOAc(50) | BF₃Et₂O(62) | " | 1 | 1880 | 47 | |
| 28. | " | " | | " | 390 | EtOAc(10) | BF₃Et₂O(3) | " | 3 | 255 | 65 | |
| 29. | " | " | | " | 657 | CH₂Cl₂(6) EtOAc(6) | BF₃Et₂O(11) | " | 7/6 | 518 | 79 | |
| 30. | " | —CHPh₂ | | " | 4750 | CH₂Cl₂(100) | CuSO₄(6.48 g) | reflux | 5/4 | 2640 | 56 | |
| 31. | —CH₂OPh | " | | " | 130 | CHCl₃(2) | BF₃Et₂O(2) | rt | ¼ | 20 | 15 | |
| 32. | " | —CH₂Ph | | " | 169 | CH₂Cl₂(1.7) | CuSO₄(169 mg) | 40 | 3.5 | 78 | 46 | |

TABLE II $$\underset{\substack{\overset{|}{\text{COOB}^1}}}{\overset{R^1\text{CONH}\ \ H}{\underset{O}{\bigsqcup}}\underset{N}{\overset{O}{\bigsqcup}}}\underset{\text{CH}_2\text{X}}{\overset{Z}{|}} \xrightarrow[\text{(ii) methanol}]{\text{(i) imino formation}} \underset{\substack{\overset{|}{\text{COOB}^1}}}{\overset{R^1\text{CONH}\ \ \text{OCH}_3}{\underset{O}{\bigsqcup}}\underset{N}{\overset{O}{\bigsqcup}}}\underset{\text{CH}_2\text{X}}{\overset{Z}{|}}$$

| No. | R¹ | B¹ | X | Z | Wt (mg) | Solvent (ml) | Reagent(ml) | Temp. (°C.) | Time (hr) | Yield mg | Yield % | Identified after modifying to |
|---|---|---|---|---|---|---|---|---|---|---|---|---|
| Methoxylation (1) | | | | | | | | | | | | |
| 1. | —Ph | —CH₂Ph | —Cl | —Cl | 504 | CH₂Cl₂(5) | 0.92M—Cl₂/CCl₄(2.49) 2N—LiOCH₃(2.69) | −50 | ¼ | 276 | 48 | Z = Δ³ |
| 2. | " | " | " | " | 47 | CH₂Cl₂(1.5) | t-BuOCl(0.040) LiOCH₃(2 eq) | " | ¼ | 46 | — | |
| 3. | " | " | " | Δ³ | 93 | CH₂Cl₂(10) | 3M—Br₂(3 μl) t-BuOCl(30 μl) 2N—LiOCH₃(0.14) | −25 | ¼ | 41 | 42 | |
| 4. | " | —CHPh₂ | " | —Cl | 141 | CH₂Cl₂(2.1) | 1.1M—Cl₂/CCl₄(0.27) | " | 1/6 | — | — | |

TABLE II-continued $$R^1CONH\overset{H}{\underset{}{\diagdown}}\underset{O}{\overset{}{\diagup}}\underset{CH_2X}{\overset{Z}{|}} \xrightarrow[\text{(ii) methanol}]{\text{(i) imino formation}} R^1CONH\overset{OCH_3}{\underset{}{\diagdown}}\underset{O}{\overset{}{\diagup}}\underset{CH_2X}{\overset{Z}{|}}$$

| No. | R[1] | B[1] | X | Z | Wt (mg) | Solvent (ml) | Reagent(ml) | Temp. (°C.) | Time (hr) | Yield mg | Yield % | Identified after modifying to |
|---|---|---|---|---|---|---|---|---|---|---|---|---|
| 5. | " | " | —H | -αOH | 486 | CH₂Cl₂(20) | 1.3N—Mg(OCH₃)₂(0.8) t-BuOCl(0.15) 2N—LiOCH₃(1.1) | −50 | ¼ | 250 | 48 | |
| 6. | " | " | " | -αOAc | 1310 | CH₂Cl₂(54) | t-BuOCl(0.4) 2N—LiOCH₃(3) | " | ¼ | 980 | 71 | |
| 7. | " | " | —Cl | —Cl | 47 | CH₂Cl₂(1.5) | t-BuOCl(1.5 eq) 2N—LiOCH₃(2 eq) | " | ⅓ | — | — | Z = Δ³ |
| 8. | " | " | " | " | 300 | CH₂Cl₂(5) | 1.1M—Cl₂/CCl₄(0.76) 1.3N—Mg(OCH₃)₂(1.69) | −30 | ¼ | 124 | — | |
| 9. | " | " | —Br | —Br | 187 | CH₂Cl₂(1) | t-BuOCl(0.046) 2N—LiOCH₃(0.17) | " | 1 | — | — | Z = Δ³, X = STetr. |
| 10. | " | " | " | " | 157 | CH₂Cl₂(2.4) | 1.1M—Cl₂/CCl₄(0.4) 1.3N—Mg(OCH₃)₂(1.1) | −15 | 1/6 | — | — | |
| 11. | " | " | —H | Δ³ | 1360 | CH₂Cl₂(30) | t-BuOCl(0.51) 2N—LiOCH₃(2.1) | −30 | ¾ | 1140 | — | |
| 12. | " | " | —Cl | " | 127 | THF(7.6) DMF(0.6) | t-BuOCl(0.05) 2N—LiOCH₃(0.23) | −50 | 1/5 | 34 | 30 | |
| 13. | " | " | " | " | 272 | CH₂Cl₂(5.5) | t-BuOCl(0.093) 2N—LiOCH₃(0.35) | −40 | ¼ | 300 | — | |
| 14. | " | " | —Br | " | 135 | " | t-BuOCl(0.05) 2N—LiOCH₂(0.2) | −30 | 1 | — | — | Z = Δ³, X = STetr. |
| | | | | | | Methoxylation (2) | | | | | | |
| 15. | —C₆H₄Cl—p | —CHPh₂ | —Cl | —Cl | 106 | CH₂Cl₂(6) | 1.2M—Cl₂/CCl₄(0.35) 2N—LiOCH₃(0.55) | −60 | 1/6 | — | — | Z = Δ³, X = STetr. |
| 16. | —C₆H₄CN—p | " | " | " | 246 | CH₂Cl₂(8) | 1.2M—Cl₂/CCl₄(0.98) 2N—LiOCH₃(1.57) | " | 1/6 | — | — | Z = Δ³, X = STetr. |
| 17. | —C₆H₄NO₂—p | " | " | " | 100 | CH₂Cl₂(2) | 1.2M—Cl₂/CCl₄(0.34) 2N—LiOCH₃(0.48) | −50 | 1/6 | 47 | 42 | Z = Δ³, X = STetr. |
| 18. | —C₆H₄CH₃—p | " | " | " | 439 | CH₂Cl₂(10) | 1.2M—Cl₂/CCl₄(1.4) 2NLiOCH₃(2.3) | −55 | 1/6 | 391 | 79 | Z = Δ³, X = STetr. |
| 19. | —CH₂Ph | —Bu-t | " | " | 76 | CH₂Cl₂(2) | 1.2M—Cl₂/CCl₄(0.15) 2N—LiOCH₃(0.34) | −50 | 1/6 | 74 | — | Z = Δ³, X = STetr. |
| 20. | " | —CH₂Ph | " | " | 222 | CH₂Cl₂(4.4) | 1.22M—Cl₂/CCl₄(0.95) 2N—LiOCH₃(1.36) | −75 | ¼ | 193 | 75 | Z = Δ³, X = STetr. |
| 21. | " | —CHPh₂ | " | " | 101 | CH₂Cl₂(1) | 0.8M—Cl₂/CCl₄(0.56) 2N—LiOCH₃(0.52) | −50 | 1/6 | 95 | 83 | Z = Δ³, X = STetr. |
| 22. | " | " | — | | 78 | THF(3) CH₂Cl₂(2) | t-BuOCl(0.020) 2N—LiOCH₃(0.1) | −35 | ¼ | 81 | 95 | |
| 23. | " | " | " | | 90 | CH₂Cl₂(2) | t-BuOCl(0.02) 2N—LiOCH₃(0.09) | −20 | 1/12 | 54 | 58 | |
| 24. | A=NH₂— | " | " | | 100 | CH₂Cl₂(4) | t-BuOCl(0.02) 2N—LiOCH₃(0.08) | −50 | 1/12 | 82 | — | |

In the reagent, methoxides are used as methanolic solutions.

TABLE III

Addition $$R^1CONH\diagdown\underset{N}{\overset{O}{|}}\underset{\overset{|}{COOB^1}}{\overset{}{}}\overset{}{=}CH_2 \xrightarrow{XZ} R^1CONH\diagdown\underset{N}{\overset{O}{|}}\underset{\overset{|}{COOB^1}}{\overset{Z}{|}}CH_2X$$

| No. | R[1] | B[1] | X | Z | Wt (mg) | Solvent (ml) | Reagent (ml) | Temp (°C.) | Time (hr) | Yield mg | Yield % | Identified after modifying to |
|---|---|---|---|---|---|---|---|---|---|---|---|---|
| 1. | —Ph | —CHPh₂ | —OH | —OH | 100 | THF (4) H₂O (1) | KClO₃ (0.2 g) OsO₄ (0.02 g) | 70 | 2.5 | 112 | — | |
| 2. | " | " | —SCH₃ | —Cl | 100 | AcOEt (3) | 0.5M—CH₃SCl/ CCl₄ (0.6) | rt | 1 | 132 | — | |
| 3. | " | " | —Cl | " | 519 | CH₂Cl₂ (10) | 0.76N—Cl₂/CCl₄ (1.6) | −20 | ⅔ hν | 484 | 86 | |
| 4. | " | " | " | " | 103 | CH₂Cl₂ (1) | 0.75M—Cl₂/CCl₄ (0.3) | " | ½ hν | 120 | | |
| 5. | " | —CH₂Ph | " | " | 141 | CH₂Cl₂ (3) | 0.75M—Cl₂/ | −50 | ½ hν | 170 | >100 | |

TABLE III-continued

Addition $$\text{R}^1\text{CONH} \text{—} \underset{\text{COOB}^1}{\overset{O}{\underset{N}{\bigcirc}}} \text{—} \text{CH}_2 \xrightarrow{XZ} \text{R}^1\text{CONH} \text{—} \underset{\text{COOB}^1}{\overset{O}{\underset{N}{\bigcirc}}} \text{—} \underset{\text{CH}_2X}{\overset{Z}{\bigcirc}}$$

| No. | R[1] | B[1] | X | Z | Wt (mg) | Solvent (ml) | Reagent (ml) | Temp (°C.) | Time (hr) | Yield mg | Yield % | Identified after modifying to |
|---|---|---|---|---|---|---|---|---|---|---|---|---|
| 6. | " | —H | —Br | —Br | 60 | CH$_2$Cl$_2$ (3) | CH$_2$Cl$_2$ (1.4 eq) 0.84M—Br$_2$/CCl$_4$ (0.75) | −20 to +10 | 5 | 66 | — | |
| 7. | " | —CHPh$_2$ | " | " | 162 | CH$_2$Cl$_2$ (0.5) | Br$_2$ (0.02) | −30 | 1.5 | 187 | — | |
| 8. | —C$_6$H$_4$CH$_3$—p | " | —Cl | —Cl | 439 | CH$_2$Cl$_2$ (10) | 1.2M—Cl$_2$/CCl$_4$ (2.4) | −50 | 1/6 hν | — | >80 | Z = Δ$^3$ |
| 9. | —C$_6$H$_4$Cl—p | " | " | " | 106 | CH$_2$Cl$_2$ (6) | 1.2M—Cl$_2$/CCl$_4$ (0.5) | " | ¼ hν | — | >80 | " |
| 10. | —C$_6$H$_4$CN—p | " | " | " | 246 | CH$_2$Cl$_2$ (8) | 1.2M—Cl$_2$/CCl$_4$ (1.5) | " | 7/60 hν | — | >80 | " |
| 11. | —C$_6$H$_4$NO$_2$—p | " | " | " | 100 | CH$_2$Cl$_2$ (2) | 1.2M—Cl$_2$/CCl$_4$ (0.52) | " | ⅓ hν | — | 42 | " |
| 12. | —CH$_2$Ph | —Bu—t | " | " | 100 | CH$_2$Cl$_2$ (2) | 1.2M—Cl$_2$/CCl$_4$ (0.7) | −55 | 2/15 hν | 76 | 64 | |
| 13. | " | —CH$_2$Ph | " | " | 222 | CH$_2$Cl$_2$ (4.4) | 1.2M—Cl$_2$/CCl$_4$ (1.5) | −54 | 1/6 hν | — | >65 | Z = Δ$^3$ |
| 14. | " | —CHPh$_2$ | " | " | 2960 | CH$_2$Cl$_2$ (30) | 1.36 M—Cl$_2$/CCl$_4$ (8.1) | −30 | ¼ hν | 2420 | 76 | " |
| 15. | " | " | " | " | 705 | CH$_2$Cl$_2$ (7) | Cl$_2$ (1.77 eq) | −25 | — | — | >80 | " |
| 16. | —CH$_2$OPh | " | " | " | 68 | CH$_2$Cl$_2$ (1.4) | 1.5M—Cl$_2$/CCl$_4$ (1.3 eq) | −50 | ½ hν | 39 | 54 | " |

TABLE IV

| No. | R¹ | B¹ | X | Z | E | Wt (mg) | Solvent (ml) | Reagent (μl) | Temp (°C.) | Time (hr) | Yield mg | % | Note |
|---|---|---|---|---|---|---|---|---|---|---|---|---|---|
| | | | | | | | Elimination (1) | | | | | | |
| 1. | —Ph | —H | —H | —OH | -αOCH₃ | 206 | CH₂Cl₂ (5) | CH₃SO₂Cl / C₅H₅N | 0 | 1 | — | — | |
| 2. | " | —CH₂Ph | —Cl | -αOH | -βH | 1000 | THF (20) | SOCl₂ (905) / C₅H₅N (825) | rt | 63 | 688 | 71 | |
| 3. | " | " | " | -βOH | " | 200 | CH₂Cl₂ (4) | SOCl₂ (163) / C₅H₅N (182) | " | 2.5 | 100 | — | |
| 4. | " | " | —Br | —Cl | " | 50 | CH₂Cl₂ (2) | 2N—LiOCH₃/CH₃OH (0.2 ml) | −50 | ⅓ | 45 | 97 | |
| 5. | " | " | —STetr | —Br | " | 300 (=CH₂) | CH₂Cl₂ (5) | DBN (97) | rt | ⅓ | 272 | 76 | |
| 6. | " | " | " | —OH | " | 144 | CH₂Cl₂ (2.2) | SOCl₂ (60) / C₅H₅N (133) | 0 | ⅓ / 1 | 98 | — | |
| 7. | " | —CHPh₂ | " | —Br | " | 452 | CH₂Cl₂ (10) | (CH₂)₅NH (1060) | rt | 3 | 234 | 48 | |
| 8. | " | " | —H | -βOH | " | 200 | CH₂Cl₂ (10) | t-BuCONCO (131) | 0 | 5 (days) | 88 | 46 | |
| 9. | " | " | " | -αOH | " | 1929 | CH₂Cl₂ (10) | SOCl₂ (433) / C₅H₅N (1050) | " | ¾ | 627 | 34 | |
| 10. | " | " | " | -βOH | " | 97 | CH₂Cl₂ (2) / DMF (0.001) | SOCl₂ (29) / C₅H₅N (65) | " | 4.5 | 91 | — | |
| 11. | " | " | " | " | " | 973 | CH₂Cl₂ (20) | POCl₃ (367) / C₅H₅N (971) | " | 40 | 296 | — | |
| 12. | " | " | " | —OH | " | 15000 | CH₂Cl₂ (100) | SOCl₂ (3000) / (CF₃CO)₂O (300) | 0 / rt / rt | 5/4 / 9/4 / ⅓ | 2650 / 1050 / 121 | 25 / 11 / — | Z = Δ³ / Z = Δ² |
| 13. | " | " | " | —OCOCF₃ | -αOCH₃ | 103 (X = OH) | C₅H₅N (1) | SOCl₂ (300) / α-CH₃C₅H₄N (800) | " | 2.5 | 252 | 52 | |
| 14. | " | " | —Cl | —OH | -βH | 483 | CH₂Cl₂ (5) | DBN (140) | −20 | 10 | 484 | 86 | |
| 15. | " | " | " | —Cl | -αOCH₃ | 519 (=CH₂) | CH₂Cl₂ (5) | 2N—LiOCH₃/CH₃OH (1.2 ml) | −50 | 1/6 | 193 | 69 | |
| 16. | " | " | " | " | " | 300 | CH₂Cl₂ (6) | | | | | | |
| 17. | " | " | " | " | " | 141 | CH₂Cl₂ (2) | 2N—LiOCH₃/CH₃OH (0.2 ml) | −25 | 1/6 | 119 | 78 | |
| | | | | | | | Elimination (2) | | | | | | |
| 18. | —Ph | —CHPh₂ | " | —Br | -βH | 157 (=CH₂) | CH₂Cl₂ (0.5) | DBN (20) | −20 | ⅓ | 135 | 76 | |
| 19. | " | " | " | " | " | 142 | (CH₃)₂CO (1.5) | NaSTetr (90) | rt | 15 | 115 | — | X = STetr in the product |
| 20. | " | " | —STetr | —OH | " | 182 (=CH₂) | CH₂Cl₂ (5) | SOCl₂ (300) / C₅H₅N (600) | " | 2.5 | 175 | — | |
| 21. | —C₆H₄CH₃—p | " | " | —Cl | -αOCH₃ | 150 | CH₂Cl₂ (2) | (CH₂)₅NH (40) | 0 | ⅓ | 102 | 72 | |

TABLE IV-continued $$R^1CONH \overset{E}{\underset{O}{\diagdown}} \underset{COOB^1}{\overset{CH_2X}{\underset{N}{\bigvee}}} \xrightarrow{-HZ} R^1CONH \overset{E}{\underset{O}{\diagdown}} \underset{COOB^1}{\overset{CH_2X}{\underset{N}{\bigvee}}}$$

| No. | R¹ | B¹ | X | Z | E | Wt (mg) | Solvent (ml) | Reagent (µl) | Temp (°C.) | Time (hr) | Yield mg | Yield % | Note |
|---|---|---|---|---|---|---|---|---|---|---|---|---|---|
| 22. | —C₆H₄NO₂—p | " | " | " | " | 72 | CH₂Cl₂ (2) | (CH₂)₅NH (20) | " | ½ | 55 | 81 | |
| 23. | —C₆H₄CN—p | " | " | " | " | 83 | CH₂Cl₂ (2) | (CH₂)₅NH (15) | " | ½ | 64 | 82 | |
| 24. | —C₆H₄Cl—p | " | " | " | " | 96 | CH₂Cl₂ (6) | 2N—LiOCH₃/CH₃OH (0.5 ml) | −50 | ½ | 78 | 87 | |
| 25. | —CH₂Ph | —CH₂Ph | —Cl | " | -βH | 205 (=CH₂) | CH₂Cl₂ (4) | (CH₂)₅NH (80) | 0 | 2.5 | 145 | 65 | |
| 26. | " | " | —STetr | " | -αOCH₃ | 215 | CH₂Cl₂ (4) | 2N—LiOCH₃/CH₃OH (0.9 ml) | −50 | 4 | 160 | 70 | |
| 27. | " | —CHPh₂ | —Cl | " | " | 210 | CH₂Cl₂ (5) | (CH₂)₅NH | 10 | ½ | 104 | 53 | |
| 28. | " | " | " | " | -βH | 2960 | CH₂Cl₂ (30) | (CH₂)₅NH (660) | −10 | 1 | 2420 | 76 | |
| 29. | " | " | " | " | " | 705 (=CH₂) | CH₂Cl₂ (7) | (CH₂)₅NH (160) | −15 | ⅔ | 586 | 78 | |
| 30. | " | " | —STetr | " | -αOCH₃ | 123 | CH₂Cl₂ (6) | 2N—LiOCH₃/CH₃OH (0.6 ml) | −50 | 1/6 | 87 | 67 | |
| 31. | —CH₂OPh | —CH₂Ph | —Cl | " | -βH | 68 (=CH₂) | CH₂Cl₂ (1.4) | (CH₂)₅NH (16) | 0 | 0.5 | 39 | 54 | |
| 32. | —CHPh COOCHPh₂ | —CHPh₂ | " | " | -αOCH₃ | 60 | CH₂Cl₂ (2) | 2N—NaOCH₃/CH₃OH (0.2) | −50 | ½ | 51 | 81 | |
| 33. | —Ph | —Si(CH₃)₃ | " | " | -βH | 44 | THF (1) | DHN (18 mg)NaSTetr (28 mg)/THF (500) | rt | 3.5 | 18 | 44 | N = STetr in the product |

TABLE V

Continuous process

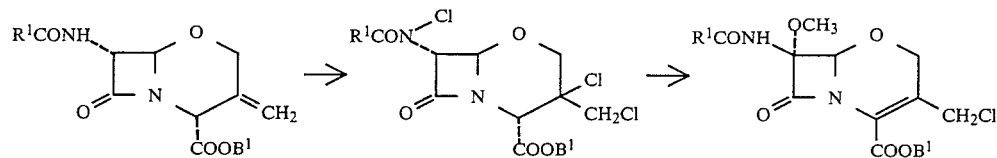

| No. | $R^1$ | $B^1$ | wt (mg) | $CH_2Cl_2$ (ml) | $Cl_2/CCl_4$ (M:ml) | Temp (°C.) | Time (min) | 2N—$LiOCH_3$/$CH_3OH$ (μl) | Temp (°C.) | Time (min) | Yield mg | % | Note |
|---|---|---|---|---|---|---|---|---|---|---|---|---|---|
| 1. | —$CH_2Ph$ | —$CH_2Ph$ | 222 | 4.4 | 1.22; 1.43 | −54 | 10(hν) | 1360 | −75 | 10 | 193 | 75 | partial $CH_3$—ester exchange |
| 2. | —Ph | —$CHPh_2$ | 504 | 5 | 0.92; 3.74 | 0 | 90 | 2690 | −50 | " | 276 | 48 | |
| 3. | —$CH_2Ph$ | " | 101 | 1 | 0.8; 0.837 | −25 | 120 | 520 | " | " | 95 | 83 | |
| 4. | —$C_6H_4NO_2$—p | " | 100 | 2 | 1.2; 0.515 | −50 | 20(hν) | 483 | " | " | 47 | 42 | |
| 5. | —$C_6H_4CH_3$—p | " | 439 | 10 | 1.2; 2.4 | " | 10(hν) | 2300 | " | 5 | 391 | 79 | |
| 6. | —$C_6H_4CN$—p | " | 246 | 8 | 1.2 1.47 | " | 7(hν) | 1570 | " | 10 | 251 | — | identified as 3-$CH_2STetr$ |
| 7. | —$C_6H_4Cl$—p | " | 106 | 6 | 1.2 0.53 | " | 15(hν) | 550 | " | " | 65 | — | identified as 3-$CH_2STetr$ |

TABLE VI

Physical contants of

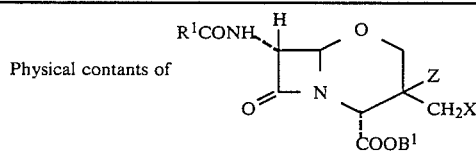

| No. | $R^1$ | $B^1$ | X | Z | mp. (°C.) | IR: $\nu_{max}^{CHCl_3}$ cm$^{-1}$ | NMR: $\delta_{ppm}^{CDCl_3}$ (Hz values show coupling constants) |
|---|---|---|---|---|---|---|---|
| 1 | —Ph | —H | = | = | — | 3350,1670,1660, 1600,1580. | 4.36s2H,5.1s2H,5.33brs3H,7.4–8.0₇5H ($CDCl_3$ + $CD_3OH$) |
| 2 | " | " | —Cl | —Cl | 118–122 | 3330,1778,1768, 1647,1605,1578, 1530. | 4.08s2H,4.65s1H,5.00d(8Hz)1H,5.37s1H, 7.3–8.2m5H,9.37d(8Hz)1H. |
| 3 | " | " | —Br | —Br | — | — | (3.83d + 4.33d)ABq(13Hz)2H,(3.9d + 4.2d) ABq(10Hz)2H,4.8s1H,5.15s1H,5.35s1H, 7.2–8.1m5H($CD_3COCD_3$). |
| 4 | " | " | —H | $\Delta^2$ | — | 3000,1775,1725, 1660. | 1.62d(1Hz)3H,4.51brs1H,4.97d(8Hz)1H, 5.33s1H,6.24brs1H,7.14–8.07m5H. |
| 5 | " | " | —H | $\Delta^3$ | — | — | — |
| 6 | " | —$CH_2Ph$ | —Cl | —Cl | — | 3430,1781,1736, 1670. | 3.52d + 3.80d(12Hz)ABq2H,(3.93d + 4.28d (12Hz)ABq2H,4.85s1H,5.01d(7Hz)1H,5.20s2H, 5.41s1H,7–8m10H. |
| 7 | " | " | —Br | —Br | — | — | not separated |
| 8 | " | " | —H | $\Delta^3$ | 208–212 | 3440,1785,1720, 1665. | 2.00s3H,4.37s2H,5.03s1H,5.10d(8Hz)1H, 5.35s2H,7.2–8.0m10H. |
| 9 | " | " | —Cl | " | 186–188 | 3250,1771,1729, 1643(Nujol). | 4.56s2H,4.60s2H,4.93dd(8;1Hz)1H,5.33d (1Hz),1H,5.36s2H.8.1–7.2m10H.9.42dd(8;1Hz) 1H($CD_3SOCD_3$). |
| 10 | " | " | —Br | " | 165–169 | 3275,1780,1472, 1647. | 4.48s2H,4.63s2H,4.97d(8;1Hz)1H,5.32d (1Hz)1H,5.38s2H,7.3–8.0m10H,9.40d (8Hz)1H ($CD_3SOCD_3$). |
| 11 | " | " | —STetr | " | 186–189 | 3430,1791,1724, 1675,1634,1584. | 3.81s3H,4.20ABq(13Hz)2H,4.55s2H, 4.93d1H,5.05s1H,5.27s2H,7.22–7.6m9H, 7.7–7.85m2H. |
| 12 | " | —$CHPh_2$ | —H | —OH | — | 3385br,1775br, 1740br,1648br (Nujol). | 1.40s3H,3.42d(11.5Hz)1H,3.85d(11.5Hz) 1H,4.35s1H,4.75d(8Hz)1H,5.27s1H, 5.67s1H,6.77d(8Hz)1H,9.08d(8Hz)1H,7.1–7.5m, 7.7–7.9m15H. |
| 13 | " | " | " | " | 207–209 | 3530,3320,1783, 1753,1745,1723, 1638(Nujol). | 0.83s3H,3.47s1H,3.73s1H,4.30s1H,4.88d (8Hz)1H,5.25s1H,5.62s1H,6.80s1H,7.1–7.6, 7.7–7.9m15H,9.07d(8Hz)1H. |
| 14 | " | " | " | —αOCOCH$_3$ | — | 3430,1780,1745, 1660. | 1.43s3H,1.77s3H,(3.45d + 4.20d)ABq(11Hz) 2H,5.03d(8Hz)1H,5.20s1H,5.43s1H,6.93d(8Hz) 1H,7.00s1H,7.2–7.9m15H. |

TABLE VI-continued

| | | | | | | |
|---|---|---|---|---|---|---|
| 15 | " | " | " | —Br | — | 3450,1793,1749, 1673. | 1.95s3H,(3.82d + 4.52d)ABq(11Hz)2H, 4.77s1H,5.05d(8Hz)1H,5.47s1H,6.93s1H, 7.1–7.9m15H. |
| 16 | " | " | ═══ | | — | 1777,1745,1666. | 4.27s2H,5.05d(8Hz)1H,5.23s1H,5.37s2H, 5.42s1H,6.95s1H,7.12d(8Hz)1H, 7.2–7.9m15H. |
| 17 | " | " | —O— | | — | 1780,1740,1675. | 2.72.3.06ABq(4Hz)2H,(3.40.4.10)ABq (12Hz)2H,4.30s1H,5.05d(7Hz)1H,5.40s1H, 6.95s1H,7.1–7.5m13H,7.7–7.9m2H. |
| 18 | " | " | " | " | — | 1780,1745,1680. | (2.88.3.98)ABq(6Hz)2H,(3.40.4.15)ABq (12Hz)2H,4.55s1H,5.18d(8Hz)1H,5.45s1H, 6.98s1H,7.3–7.6m13H,7.7–7.9m2H. |
| 19 | —Ph | —CHPh$_2$ | —OH | —OH | — | — | (3.11d + 3.45d)ABq(12Hz)2H,3.83s2H, 4.66s1H,5.1d(7Hz)1H,5.4s1H,5.9s1H, 7.1–8.0m15H(CDCl$_3$—CD$_3$OD). |
| 20 | " | " | —OAc | —OH | 118–120 | 3200,1760,1740, 1635(Nujol). | 1.8s3H,3.86brs4H,4.53s1H,5.01d(8Hz)1H, 5.36s1H,6.06s1H,6.9s1H,7.2–8.1m15H. |
| 21 | " | " | —O$_3$SCH$_3$ | " | — | — | 2.75s3H,3.83br4H,4.75s1H,5.06d(7Hz)1H, 5.36s1H,6.88s1H,7–8.m15H. |
| 22 | " | " | —H | $\Delta^3$ | 144–146 | 3440,1782,1722, 1663. | 1.92s3H,4.23s2H,4.90s1H,5.07d(8Hz)1H, 6.88s1H,7.1–8.0m16H. |
| 23 | " | " | —Cl | —OH | — | 3550br,3450–3200, 1782,1745,1670. | 3.87s2H,3.98s2H,4.93s1H,4.97d(8Hz)1H, 5.40s1H,6.97s1H,7.23–7.6m13H,7.7–7.9m2H. |
| 24 | " | " | " | " | — | 3550,3450–3200, 1780,1740,1665. | (3.08 + 3.38)ABq(12Hz)2H,3.83brs2H, 4.78s1H,5.10d(7Hz)1H,5.45s1H,6.93s1H, 7.25–7.58m13H,7.7–7.9m2H. |
| 25 | " | " | —Cl | —Cl | — | — | (3.37 + 3.69d)(12Hz)ABq2H,(3.88d + 4.23d(12Hz)2H,5.00s1H;5.08d(7Hz)1H,5.38s1H, 6.93s1H,7.02d(7Hz)1H,7–8m15H. |
| 26 | " | " | —SCH$_3$ | " | — | — | 2.0s3H,(3.01d + 3.36d)ABq(12Hz)2H, (3.65 + 3.95d)ABq2H,4.37s1H,4.8d1H,5.18s1H, 6.57s1H,6.8–7.6m15H. |
| 27 | " | " | —STetr | —OH | — | 3350br,1777, 1745,1669. | TLC: Rf = 0.57 & 0.63 (for each isomer at 3) (SiO$_2$/PhH + EtOAc(1:1)). |
| 28 | " | " | —Cl | $\Delta^3$ | 120–128 | 3375,1790,1728, 1670. | 4.35s2H,4.48s2H,4.98s1H,5.02d(6Hz)1H, 6.90s1H,7.1–8.0m16H. |
| 29 | " | " | —STetr | " | 203–205 | 3450,1792,1725, 1680. | 3.77s3H,4.20s2H,4.57s2H,4.90d(7Hz)1H, 5.07s1H,6.93s1H7.2–7.9m16H. |
| 30 | " | " | —Br | —OH | — | 3600–3150,1780, 1740,1670. | (2.93 + 3.28)ABq(11Hz)2H,4.57brs2H, 4.82s1H,5.12d(7Hz)1H,5.43s1H,6.97s1H, 7.2–7.6m13H,7.7–8.2m2H. |
| 31 | " | " | " | " | — | 3550,3440–3150, 1780,1745,1675. | 3.78s2H,3.97s2H,5.02s1H,5.02d(7Hz)1H, 5.40s1H,7.03s1H,7.3–7.5m13H,7.8–7.9m2H. |
| 32 | " | " | " | —Br | — | 3450,1788,1740, 1673. | (3.30d + 3.60d)(12Hz)ABq2H,(3.87 + 4.13d)(12Hz)2H,5.0d(8Hz)1H,5.07s1H, 5.37s1H,6.87s1H,7.1–7.9m16H. |
| 33 | " | " | " | $\Delta^3$ | — | 3400,1790,1727, 1668. | (4.10 + 4.27d)ABq(7Hz)2H,4.63brs2H, 5.00s1H,5.00d(7Hz)1H,6.90s1H,7.2–7.9m16H. |
| 34 | —C$_6$H$_4$CH$_3$p | " | ═══ | | 187–188 | 1775,1743,1668. | 2.36s3H,4.20s2H,4.90–5.43m5H,6.83s1H, 7.0–7.9m14H. |
| 35 | —C$_6$H$_4$Cl—p | " | " | " | 192–193 | 3430,1777,1745, 1672,1599. | 4.23s2H,4.97d(8Hz)1H,5.17s1H,5.3–5.4m3H, 6.85s1H,7.2–7.5m12H,7.73d(8Hz)1H. |
| 36 | —C$_6$H$_4$CN—p | " | " | " | 148–149 | 3435,2235,1775, 1745,1675,1615. | 4.23s2H,4.97d(8Hz)1H,5.17s1H,5.3–5.4m3H, 6.87s1H,7.3–7.5m10H,(7.67d + 7.90d) ABq(8Hz)4H. |
| 37 | —C$_6$H$_4$NO$_2$p | " | " | " | | 1772,1741,1679. | 4.23s2H,4.90–5.50m5H,6.85s1H, 7.16–8.36m14H. |
| 38 | —CH$_2$OPh | " | " | " | | 3415,1780,1745, 1695. | 4.33brs2H,4.60s2H,5.03d(8Hz)1H, 5.30s1H,5.38s2H,5.47s1H,7.00s1H,7.22d (8Hz)1H,6.9–7.8m15H. |
| 39 | —CH$_2$OPh | —CH$_2$Ph | —Cl | $\Delta^3$ | 162–164 | 3420,1796,1725, 1695. | 4.48s2H,4.56s4H,4.90d(8Hz)1H,5.10s1H, 7.03s1H,6.6–7.7m16H. |
| 40 | " | —CHPh$_2$ | ═══ | | — | 3410,1777,1742, 1691. | 4.22s2H,4.50s2H,4:93d(8Hz)1H,5.18s1H, 5.26s2H,5.33s1H,6.05s1H,7.5–6.6m16H. |
| 41 | " | " | —Cl | $\Delta^3$ | 162–164 | 3420,1794,1725, 1695. | 4.48s2H,4.56s4H,4.90d(8Hz)1H,5.10s1H, 7.03s1H,7.7–6.7m16H. |
| 42 | —CH$_2$Ph | —t-Bu | ═══ | | 138–139 | 2982,1773,1732, 1680. | 1.41s9H,3.56s2H,4.26s2H,4.73d(8Hz)1H, 4.88s1H,5.06–5.3m3H,6.58d(8Hz)1H, 7.26s5H. |
| 43 | " | " | —Cl | —Cl | | 1788,1731,1683. | L.50s9H,3.60s2H,3.73d(4Hz)2H, (3.90d + 4.30d)ABq(12Hz)2H,4.66s1H,4.76d (4Hz)1H,7.30s5H |
| 44 | " | —CH$_2$Ph | ═══ | | 127–131 | 3425,1776,1742, 1681. | 3.60s2H,4.27s2H,4.77d(8Hz)1H,5.08s1H, 5.18–5.28m5H,6.37d(8Hz)1H, 7.12–7.5m10H. |
| 45 | " | " | —Cl | $\Delta^3$ | 137–140 | 3265,1780,1736, 1660(Nujol). | 3.45s2H,4.45s2H,4.51s2H,4.83d(8Hz)1H, 4.95s1H,5.31s2H.7.2–7.7m10H (CD$_3$SOCD$_3$ + CDCl$_3$). |
| 46 | " | —CHPh$_2$ | ═══ | | 110–112 | 3425,1777,1745, 1684,1604. | 3.51s1H,4.15s2H,4.73d(7.5Hz)1H, 5.12s2H,5.25d(4Hz)2H,6.40d(7.5Hz)1H, 6.82s1H,7.07–7.5m15H. |
| 47 | " | " | —Cl | —Cl | — | — | TLC: Rf = 0.53(SiO$_2$/C$_6$H$_6$ + |

TABLE VI-continued

| No. | | | | | mp (°C.) | IR: $\nu_{max}^{CHCl_3}$ | NMR: $\delta^{CDCl_3}$ (Hz values show coupling constants) |
|---|---|---|---|---|---|---|---|
| 48 | " | " | " | Δ³ | 180-183 | 3295,1788,1733, 1658,1536(Nujol) | CH₃COOC₂H₅). 3.57s2H,4.4-4.6m4H,4.73d(8Hz)1H, 5.07s1H,6.90s1H,7.0-8.0m15H,8.75d(8Hz)1H (CD₃SOCD₃ + CD₃OD). |
| 49 | 7-amino deriv. | " | ══════ | — | 3000,1770,1760 1740. | 1.72brs2H,4.23s2H,5.03s1H,5.15s1H, 5.2-5.4m2H,6.87s1H,7.2-7.5m10H. |

Physical constants of

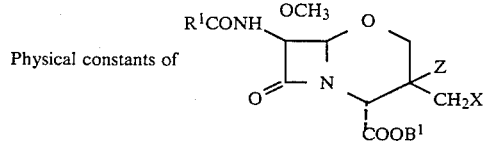

| No. | R¹ | B¹ | X | Z | mp (°C.) | IR: $\nu_{max}^{CHCl_3}$ | NMR: $\delta^{CDCl_3}$ (Hz values show coupling constants) |
|---|---|---|---|---|---|---|---|
| 1 | —Ph | —H | —H | —αOH | 100-105 | 3330,1765,1662 (KBr). | 1.50s3H,3.52s3H,(3.53d + 3.93d)ABq2H, 4.33s1H,5.33s1H,7.4-8.2m5H, (CD₃COCD₃) |
| 2 | " | " | " | —βOAc | 203-213 | 3280,1785,1739, 1722,1659(KBr) | 1.50s3H,1.98s3H,3.55s3H,5.00s1H,5.60s1H, 7.4-8.1m5H (CDCl₃ + CD₃OD = 4:1) |
| 3 | " | " | " | —βOCOCF₃ | 108-113 | 1780,1740,1660 (KBr) | — |
| 4 | " | —CH₂Ph | —Cl | —Cl | — | — | — |
| 5 | " | " | —Br | —Br | — | — | — |
| 6 | " | " | —STetr. | Δ³ | — | 3420,2840,1790, 1725,1680. | 3.59s3H,3.83s3H,4.27s2H,4.60s2H,5.15s1H, 5.32s2H,7.00-7.92m11H |
| 7 | " | —CHPh₂ | ══════ | | 196-198 | 3425,1780,1746, 1683 | 3.53s3H,4.23s2H,5.17 + 5.27-3H,5.47s1H, 6.87s1H,7.2-8.0m17H. |
| 8 | " | " | —H | —αOH | — | 3430,3350,1780, 1747,1690. | 1.43s3H,3.52s3H,(3.53d + 3.83d)(12Hz) ABq2H,4.57s1H,5.40s1H,3.03brs1H, 6.9-8.0m17H. |
| 9 | " | " | " | —βOAc | — | 3430,1782,1740, 1690. | 1.27s3H,1.97s3H,3.60s3H,(3.88 + 4.32d) (12Hz)2H,5.22brs1H,5.60s1H, 7.0-8.1m16H. |
| 10 | " | " | " | —βOCOCF₃ | — | — | 1.50s3H,2.67brs1H,3.58s3H,3.82s2H,4.55s1H, 5.42s1H,6.9-8.2m16H. |
| 11 | " | " | " | Δ³ | — | 3430,1788,1728, 1688. | 1.95s3H,3.63s3H,4.25s2H,5.12s1H,6.96s1H, 7.2-8.1m15H. |
| 12 | " | " | —Cl | —Cl | — | 3430,1785,1748, 1684. | (3.40d + 3.70d)ABq(12Hz)2H,3.57s3H, (3.88d + 4.30d)ABq(12Hz)2H,5.02s1H, 5.43s1H,6.93s1H,7.2-8.2m. |
| 13 | " | " | " | Δ³ | — | 3430,1787,1728, 1682. | 3.63s3H,4.50s2H,4.55s2H,5.25s1H,7.00s1H, 7.1-7.95m16H. |
| 14 | " | " | —Br | —Br | — | 3430,1789,1740, 1688,1605,1585. | 3.50ABq(19;12Hz)2H,3.53s3H,4.08ABq (19;12Hz)2H,5.07s1H,5.37s1H,6.90s1H, 7.2-8.0m16H. |
| 15 | p-CH₃C₆H₄— | " | —Cl | Δ³ | — | 1788,1727,1680. | 2.38s3H,3.60s3H,4.45s2H,4.50s2H,5.20s1H, 6.93s1H,7.06-7.96m14H. |
| 16 | " | " | —STetr. | " | — | 1788,1720,1683. | 2.38s3H,3.60s3H,3.76s3H,4.26s2H,4.61s2H, 5.16s1H,6.91s1H,6.96s1H,7.10-7.90m14H. |
| 17 | NO₂C₆H₄— | —CHPh₂ | —Cl | Δ³ | — | 1788,1728,1690. | 3.61s3H,4.45s2H,4.55s2H,5.21s1H,6.93s1H, 7.06-8.36m14H. |
| 18 | " | " | —STetr. | " | — | 1790,1725,1695. | 3.65s3H,3.80s3H,4.25s2H,4.66s2H,5.16s1H, 6.88s1H,7.13-8.36m14H. |
| 19 | ClC₆H₄— | " | " | " | — | — | 3.60s3H,3.77s3H,4.25s2H,4.63s2H,5.15s1H, 6.92s1H,7-8m14H. |
| 20 | NCC₆H₄— | " | " | " | — | 3425,2230,1790, 1721,1693,1632. | 3.63s3H,3.73s3H,4.25s2H,5.17brs2H, 5.17s1H,6.92s1H,7.2-8.3m14H. |
| 21 | PhCH₂— | —CH₃ | —Cl | " | — | 3410,1285,1795, 1727,1696. | 3.43s3H,3.65s2H,3.87s3H,4.50s4H,5.07s1H, 6.47brs1H,7.33brs5H. |
| 22 | " | —Bu-t | " | " | — | — | 1.50s9H,3.43s3H,3.66s2H,4.46s4H,5.05s1H, 6.66s1H,7.30s5H. |
| 23 | " | " | —STetr. | " | — | 3400,1783,1700. | 1.55s9H,3.43s3H,3.66s2H,3.93s3H,4.30s2H, 4.56s2H,5.01s1H,6.41s1H,7.30s5H. |
| 24 | " | —CH₂Ph | —Cl | " | — | 3410,1788,1725, 1698. | 3.38s3H,3.60s2H,4.42s4H,5.02s1H,5.27s2H, 6.70brs1H,7.27-7.33m10H. |
| 25 | " | " | —STetr. | " | — | — | 3.40s3H,3.60s2H,3.80s3H,4.22s2H,4.55s2H, 5.00s1H,5.27s2H,6.55brs1H,7.25-7.33m10H. |
| 26 | " | —CHPh₂ | —Cl | " | — | — | 3.43s3H,3.63s2H,4.48s4H,5.07s1H, 6.40brs1H,6.92s1H,7.23-7.60m15H. |
| 27 | " | " | —STetr. | " | 176-178 | 3410,1792,1700. | 3.42s3H,3.60s2H,3.67s3H,4.17s2H, 4.53brs2H,5.02s1H,6.77brs1H,6.87s1H, 7.17-7.50m15H. |
| 28 | 7-amino deriv. | —CH₂Ph | " | " | — | — | 3.43s3H,3.80s3H,4.23s2H,4.62s2H,4.82s1H, 5.30s2H,7.32m5H,2.25brs2H. |
| 29 | 7-amino deriv. | —CHPh₂ | ══════ | | — | 3360,3300,1770, 1740,1600. | 3.33br2H,3.45s3H,4.31brs2H,5.1-5.5m4H, 6.88s1H,7.1-7.7m10H. |
| 30 | 7-amino deriv. | " | —STetr. | Δ³ | 149-151 | — | |
| 31 | pClC₆H₄— | " | " | " | — | — | 3.60s3H,3.77s3H,4.25s2H,4.63s2H, |

TABLE VI-continued

| 32 | pNCC6H4— | " | " | " | — | 3425,2230,1790, 1721,1693,1632. | 5.15s1H,6.92s1H,7–8m14H. 3.63s3H,3.73s3H,4.25brs2H,5.17brs2H, 5.17s1H,6.92s1H,7.2–8.3m14H, |
| --- | --- | --- | --- | --- | --- | --- | --- |
| 33 | pO2NC6H4— | " | " | " | — | 1790,1725,1695. | 3.65s3H,3.80s3H,4.25s2H,4.66s2H,5.16s1H, 6.88s1H,7.1–8.4m14H. |
| 34 | pCH3C6H4— | " | " | " | — | 1788,1720,1683. | 2.38s3H,3.60s3H,3.76s3H,4.26s2H,4.61s2H, 5.16s1H,6.91s1H,6.96s1H,7.1–7.9m14H. |
| 35 | Ph— | —CH2C6H4CH3p | " | " | — | 3420,1780,1718, 1680. | 2.33s3H,3.56s3H,3.83s3H,4.25s2H,4.58s2H, 5.13s1H,5.28s2H,6.9–8.0m10H. |
| 36 | Ph— | —CH2C6H4Cl—p | " | " | — | 3425,1791,1729, 1690. | 3.56s3H,3.83s3H,4.26s2H,4.60s2H,5.11s1H, 5.25s2H,6.95s1H,7.1–8.0m9H. |
| 37 | Ph— | —CH2(naphthyl) | " | " | — | 3430,1790,1728, 1688. | 3.58s3H,3.80s3H,4.25s2H,4.60s2H,5.15s1H, 5.85s2H,6.98s1H,7.2–8.3m12H. |

EXAMPLE AA (ADDITION)

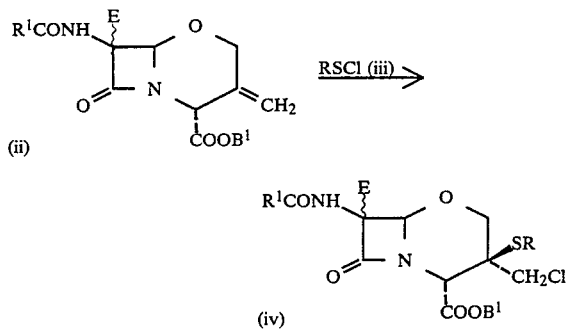

(Method)

According to the data on Table AA, an exomethylene compound (ii) in a mixture of dichloromethane and ethyl acetate is mixed with a sulfenyl chloride reagent (which may be prepared from e.g. (RSA)$_2$ and chlorine), and permitted to react for given time at given temperature to give a sulfide compound (iv).

EXAMPLE AA-1 (ADDITION—SUPPLEMENTS)

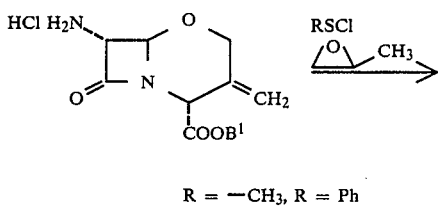

R = —CH3, R = Ph (1) R = CH3

To a solution of 7α-amino-3-methylene-1-dethia-1-oxacepham-4-carboxylic acid diphenylmethyl ester hydrochloride (1.0 g) in dichloromethane (10 ml) is added a solution of methanesulfenyl chloride (6 molar equivalents) in dichloromethane (10 ml) under nitrogen atmosphere at −10° C., and the mixture is stirred for 40 minutes to afford a solution containing 7α-amino-3β-methylthio-3α-chloromethyl-1-dethia-1-oxacepham-4α-carboxylic acid diphenylmethyl ester hydrochloride. NMR: $\delta_{ppm}^{CDCl_3}$ 1.67s2H, 2.13s2H.

To this solution are added propylene oxide (10 ml) and powdered Molecular Sieves (5 g). The mixture is stirred at room temperature for 1 hour. Solid material is filtered off, and the filtrate is concentrated. Residue is purified by silica gel chromatography to give 7-methylthioimino-3β-methylthio-3α-chloromethyl-1-dethia-1-oxacepham-4α-carboxylic acid diphenylmethyl ester (569 mg). Yield: 47% from the hydrochloride. IR: $\nu_{max}^{CHCl_3}$ 1780, 1740 cm$^{-1}$.

(2) R=Ph

Under a condition similar to above (1), but substituting methanesulfenyl chloride with phenylsulfenyl chloride, one obtains 7-phenylthioimino-3β-phenylthio-3α-chloromethyl-1-dethia-1-oxacepham-4α-carboxylic acid diphenylmethyl ester (IR: $\nu_{max}^{CHCl_3}$ 1780, 1740 cm$^{-1}$) in 48% yield through 7α-amino-3β-phenylthio-3α-chloromethyl-1-dethia-1-oxacepham-4α-carboxylic acid diphenylmethyl ester(NMR: $\delta_{ppm}^{CDCl_3}$ 1.80brs2H, 4.60s1H.).

TABLE AA

Addition (Part 1)

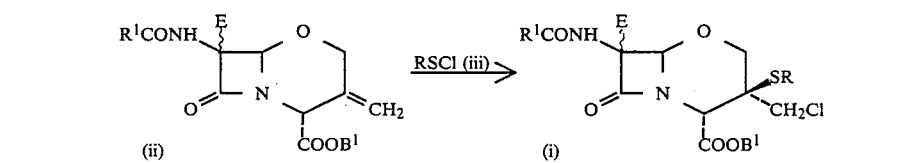

| | exomethylene compound (ii) | | | | CH2Cl2 | CH3CO C2H5O | RSCl (iii) | | | time |
| --- | --- | --- | --- | --- | --- | --- | --- | --- | --- | --- |
| No. | R | R1 | E | B1 | (g) | (ml) | (ml) | (RS)2 (ml) | CCl4 (ml) | 1M-Cl2/ CCl4(ml) | (min) |
| 1 | CH3 | Ph | β-H | CHPh2 | 4.68 | 15 | 60 | 0.9 | 30 | 10 | 20 |
| 2 | CH3 | tolyl | β-H | CHPh2 | 4.83 | 15 | 75 | 0.9 | 8.0 | 10 | 20 |

TABLE AA-continued

Addition (Part 1)

R¹CONH-[β-lactam]-CH₂=... (ii) + RSCl (iii) → R¹CONH-[β-lactam]-SR, CH₂Cl (i)

| No. | R¹ | R | E | B¹ | (g) | (ml) | (mg) | temp (°C.) | time (min) | (eq.) | |
|---|---|---|---|---|---|---|---|---|---|---|---|
| 3 | CH₃ | tolyl | α-CH₃O | CHPh₂ | 3.90 | 35 | 50 | 0.7 | 24 | 7.6 | 25 |
| 4 | CH₃ | thenyl | α-CH₃O | CHPh₂ | 1.04 | 10 | — | 0.2 | 5 | 2 | 20 |
| 5 | CH₃ | malonyl PMB | α-CH₃O | CHPh₂ | 0.50 | — | 4 | (0.61 mM CH₃SCl) | | | |
| 6 | Ph | Ph | β-H | CHPh₂ | 7.0 | 30 | 100 | 3.27 | 25 | 15 | 20 |
| 7 | Ph | Ph | β-H | CH₃ | 0.24 | 3 | — | 0.16 | 1.5 | 0.75 | 15 |
| 8 | Ph | tolyl | β-H | CHPh₂ | 0.48 | 2 | 6 | 0.22 | 2.0 | (SO₂Cl₂) 0.08 | 30 |
| 9 | Ph | tolyl | α-CH₃O | 0.33 | 10 | 20 | 0.33 | | 4.0 | 1.5 | 20 |
| 10 | Ph | thenyl | α-CH₃O | CHPh₂ | 3.0 | — | 30 | (16.9 mM PhSCl/CH₂Cl₂) | | | |
| 11 | Ph | malonyl PMB | α-CH₃O | CHPh₂ | 0.3 | — | 10 | (1 eq. PhSCl/CH₂Cl₂) | | | |

| No. | temp (°C.) | time (min) | crop (g) | yield (%) | IR: $\nu_{max}^{CHCl_3}$ cm⁻¹ |
|---|---|---|---|---|---|
| 1 | rt | 150 | 5.46 | quant | 3400, 1785, 1745, 1680 |
| 2 | rt | 120 | 6.05 | 92 | mp. 182–183° C. |
| 3 | rt | 150 | 3.90 | 85 | NMR: 2.02s3H, 2.37s3H* |
| 4 | rt | 90 | 1.03 | 76 | 3390, 1790, 1747, 1697 |
| 5 | 0° | 60 | 0.53 | 89 | NMR: (1.96s + 1.98s)3H* |
| 6 | rt | 120 | 8.08 | 88 | 3430, 1785, 1745, 1675 |
| 7 | rt | 60 | 0.16 | 46 | 3430, 1785, 1750, 1680 |
| 8 | rt | 300 | 0.47 | 75 | mp. 218–219° C. |
| 9 | rt | 180 | 1.21 | 93 | mp. 211–212° C. |
| 10 | 0 | 180 | 3.39 | 88 | 3380, 1780, 1740, 1695 |
| 11 | rt | 260 | 0.3 | 78 | NMR: (3.40s + 3.41s)3H* |

*NMR: $\delta_{ppm}^{CDCl_3}$

EXAMPLE BB (ADDITION OF SELENYL)

exomethylene compound (ii) + RSeCl (iii) → selenide (iv) R¹CONH-[β-lactam]-SeR, CH₂Cl, COOB¹

(Method)
According to the data of Table BB, an exomethylene compound (ii) in dichloromethane is mixed with a selenyl chloride reagent (iii) and permitted to react for given time at given temperature to give a selenide (iv).

TABLE BB

Addition (Part 2)

compound (i) + RSeCl (iii) → compound (ii)

| | exomethylene compound (ii) | | | | CH₂Cl₂ | RSeCl (iii) | temp. | time | selenide (iv) | | |
|---|---|---|---|---|---|---|---|---|---|---|---|
| No. | R | R¹ | E | B¹ | (g) | (ml) | (mg) | (°C.) | (min) | crop (g) | yield (%) | m.p. |
| 1 | Ph | Ph | β-H | CHPh₂ | 1.17 | 10 | 955 | rt | 90 | 1.44 | 87 | 160–161° C. |
| 2 | Ph | Ph | β-H | H | 0.15 | 4 | 120 | 0 | 240 | 0.60 | — | TLC: Rf 0.28(EtOAc:HOAc:H₂O (16:1:1))/SiO₂ |

TABLE BB-continued

Addition (Part 2)

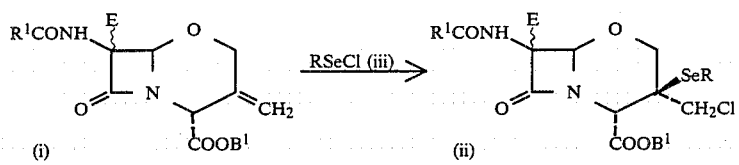

| | exomethylene compound (ii) | | | | CH₂Cl₂ | RSeCl (iii) | temp. | time | selenide (iv) | | |
|---|---|---|---|---|---|---|---|---|---|---|---|
| No. | R | R¹ | E | B¹ | (g) | (mg) | (°C.) | (min) | crop (g) | yield (%) | m.p. |
| 3 | Ph | tolyl | α-CH₃O | CHPh₂ | 0.26 | 4 | 191 | rt | 360 | 0.27 | 77 | 173–174° C. |

EXAMPLE CC (SUBSTITUTION)

given temperature for given time to obtain a 1-methyl-5-tetrazolylthio substituted product (vi).

TABLE CC

Substitution (Part 1)

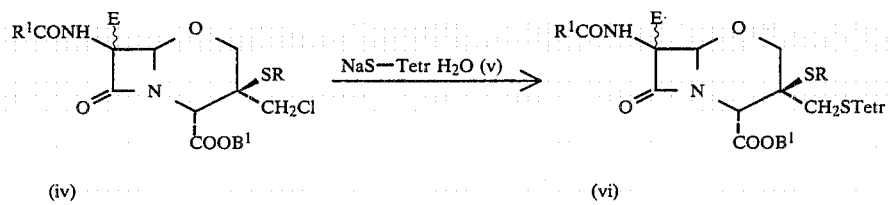

| | halomethyl compound (iv) | | | | CH₃OH | CH₃COCH₃ | NaSTetr H₂O | temp | time | R²-Substituted compound (vi) | | |
|---|---|---|---|---|---|---|---|---|---|---|---|---|
| No. | R | R¹ | E | B¹ | (g) | (ml) | (ml) | (g) | (°C.) | (min) | crop (g) | yield (%) | IR:$\nu_{max}^{CHCl_3}$ cm⁻¹ |
| 1 | CH₃ | Ph | β-H | CHPh₂ | 2.20 | 40 | 20 | 1.40 | refl | 120 | 2.56 | 98 | mp. 204–205° C. |
| 2 | CH₃ | tolyl | β-H | CHPh₂ | 1.00 | 20 | 10 | 0.66 | refl | 120 | 1.06 | 93 | mp. 208–209° C. |
| 3 | CH₃ | tolyl | α-CH₃O | CHPh₂ | 3.90 | 30 | 12 | 1.55 | refl | 20 | 5.03 | 98 | NMR: 1.97 s 3H, 2.40 s 3H, 3.57 s 3H* |
| 4 | CH₃ | thenyl | α-CH₃O | CHPh₂ | 0.80 | 16 | 8 | 0.50 | refl | 40 | 0.89 | 98 | 3400, 1790, 1745, 1705 |
| 5 | CH₃ | malonyl PMB | α-CH₃O | CHPh₂ | 0.60 | 2.5 | 2.5 | 0.09 | refl | 30 | 0.53 | 92 | NMR: (1.88 s + 1.92 s)3H* |
| 6 | Ph | Ph | β-H | CHPh₂ | 1.23 | 20 | 10 | 0.70 | refl | 16 hr | 0.97 | 70 | mp. 175–176° C. |
| 7 | Ph | thenyl | α-CH₃O | CHPh₂ | 1.00 | 10 | 10 | 0.42 | refl | 30 hr | 0.66 | 59 | 3390, 1780, 1740, 1695 |
| 8 | Ph | malonyl PMB | α-CH₃O | CHPh₂ | 0.14 | 0.7 | 0.7 | 0.03 | refl | 24 hr | — | 60 | 3400, 1780, 1735, 1720 |

* NMR:$\delta_{ppm}^{CDCl_3}$

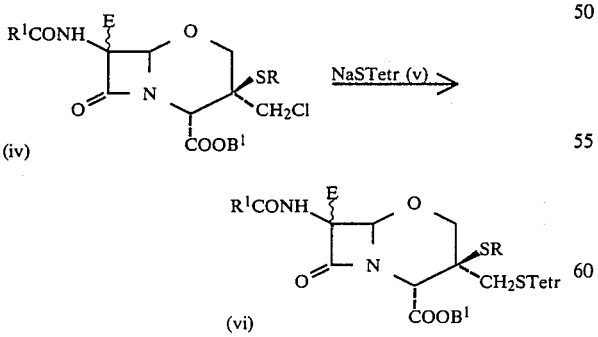

(Method)
According to the data of Table CC, a chloromethyl compound (iv) is dissolved in a mixture of methanol and acetone, mixed with 1-methyl-5-tetrazolylthiol sodium salt dihydrate, and the mixture is permitted to react at

EXAMPLE DD (SUBSTITUTION)

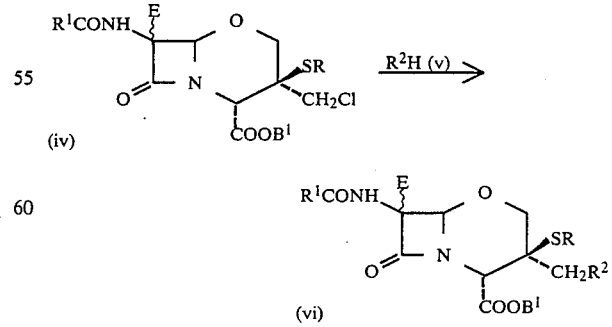

(Method)
According to the data of Table DD, a solution of a chloromethyl compound (iv) in a solvent is mixed with a nucleophilic reagent (v) (which can be the same with the solvent), an acid scavenger (calcium carbonate, etc.) and a dehalogenating reagent (e.g. silver salt). The mixture is kept at the given temperature for given time. The reaction mixture is worked up in a conventional manner to give a $R^2$-substituted 1-dethia-1-oxacepham compound (vi).

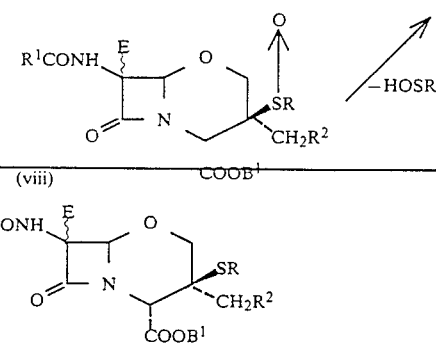

TABLE DD

Substitution (Part 2)

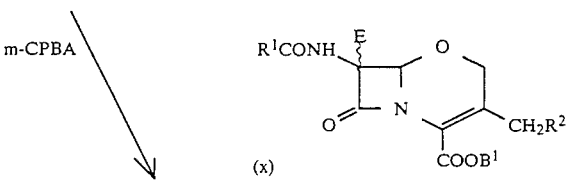

(iv)          (vi)

| No. | halomethyl compound (iv) | | | | | nucleophilic reagent (ml) solvent (ml) | CaCO₃ (mg) | silver salt (mg) | temp (°C.) | time (min) | compound (vi) | | | |
|---|---|---|---|---|---|---|---|---|---|---|---|---|---|---|
| | R | $R^1$ | E | $B^1$ | (mg) | | | | | | $R^2$ | (mg) | (%) | IR: $\nu_{max}^{CHCl_3}$cm$^{-1}$ |
| 1 | CH₃ | Ph | β-H | CHPh₂ | 275 | CH₃CO(CH₃)₂ (3) | 150 | AgBF₄ (196) | rt | 180 | CH₃COO | 218 | 76 | 3435, 1785, 1750, 1683 |
| 2 | CH₃ | thenyl | α-CH₃O | CHPh₂ | 1200 | CH₃CON(CH₃)₂ (20) | 800 | AgClO₄ (920) | rt | 210 | CH₃COO | 885 | 71 | 3400, 1790, 1750, 1695 |
| 3 | Ph | thenyl | α-CH₃O | CHPh₂ | 800 | CH₃CON(CH₃)₂ (12) | 500 | AgClO₄ (556) | rt | 24 hr | CH₃COO | 659 | 67 | 3400, 1780, 1745, 1695 |
| 4 | CH₃ | Ph | β-H | CHPh₂ | 275 | CH₃COCH₃(2) CH₃OH (4) | 150 | AgBF₄ (196) | rt | 60 | CH₃O | 203 | 75 | 3425, 1778, 1743, 1672 |
| 5 | CH₃ | tolyl | α-CH₃O | CHPh₂ | 595 | CH₃OH (6) | 300 | AgBF₄ (390) | rt | 90 | CH₃O | 585 | 99 | NMR: 2.02 s 3H, 2.38 s 3H ppm* |
| 6 | CH₃ | thenyl | α-CH₃O | CHPh₂ | 1900 | CH₃OH (15) | 300 | AgClO₄ (415) | rt | 90 | CH₃O | 1810 | 96 | 3400, 1783, 1743, 1695 |
| 7 | CH₃ | tolyl | β-H | CHPh₂ | 282 | CH₃SOCH₃ H₂O | 150 | AgBF₄ (196) | rt | 60 | HO | 180 | — | NMR:2.00 s 3H, 2.32 s 3H ppm* |

*NMR: $\delta_{ppm}^{CDCl_3}$

EXAMPLE EE (OXIDATION AND ELIMINATION)

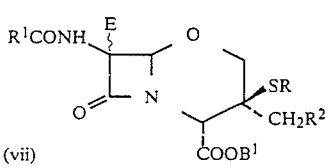

(Method)

According to the data on Table EE, a solution of a sulfide (vii) in dichloromethane is mixed with m-chloroperbenzoic acid and the mixture is kept at given temperature for given time yielding the corresponding sulfoxide (viii) accompanied by a cephem type compound (x). The mixture is refluxed for 30 minutes in acetone to give the cephem type compound (x) as a result of the elimination of a sulfenic acid from unreacted sulfoxide (viii). The reaction mixture is purified in a conventional manner to obtain a cephem type compound (x) in given yield.

TABLE EE

Oxidation and Elimination (Part 1)

| No. | sulfide (vii) | | | | | | CH₂Cl₂ (ml) | m-CPBA (mg) | temp (°C.) | time (min.) | cephem compound (x) | | | |
|---|---|---|---|---|---|---|---|---|---|---|---|---|---|---|
| | R | $R^1$ | $R^2$ | E | $B^1$ | (mg) | | | | | (mg) | (%) | mp. (°C.) | IR: $\nu_{max}^{CHCl_3}$ cm$^{-1}$ |
| 1 | CH₃ | Ph | Cl | β-H | CHPh₂ | 200 | 6 | 64 | 0 | 30 | 124 | 68 | amorph. powder | 3440, 1793, 1732, 1675. |

TABLE EE-continued

Oxidation and Elimination (Part 1)

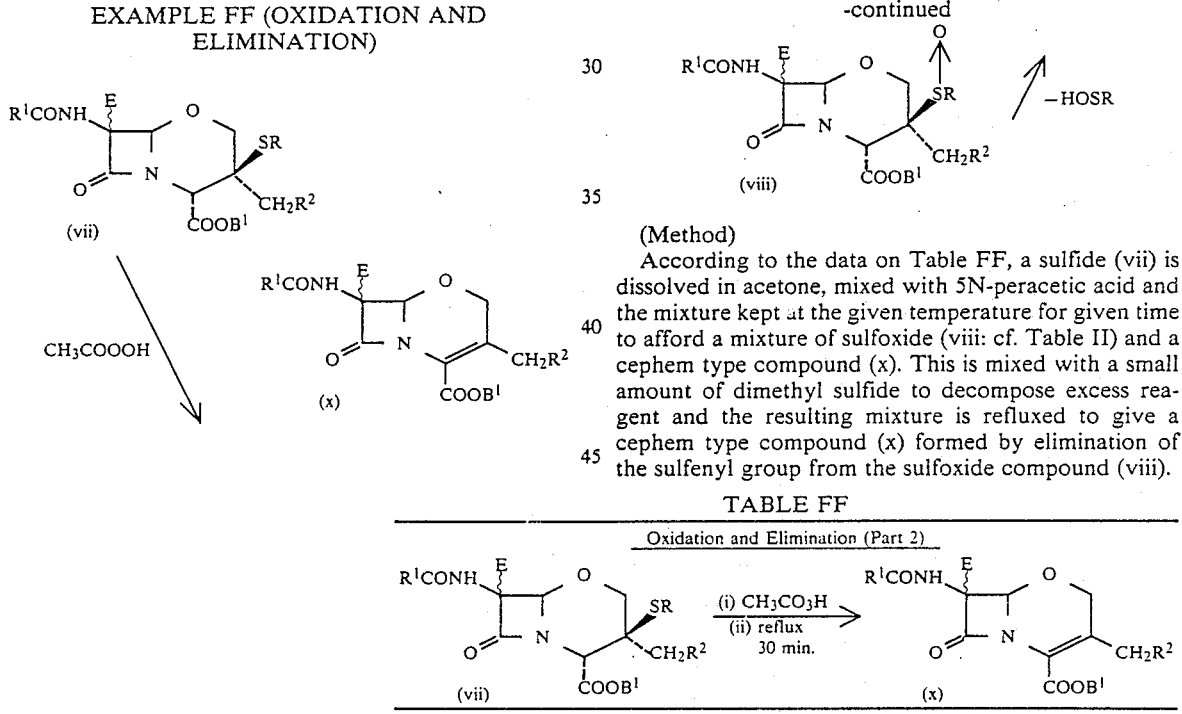

| No. | R | R[1] | R[2] | E | B[1] | sulfide (vii) (mg) | $CH_2Cl_2$ (ml) | m-CPBA (mg) | temp (°C.) | time (min.) | cephem compound (x) (mg) | (%) | mp. (°C.) | IR: $\nu_{max}^{CHCl_3}$ cm$^{-1}$ |
|---|---|---|---|---|---|---|---|---|---|---|---|---|---|---|
| 2 | $CH_3$ | Ph | STetr | β-H | $CH_2$ | 180 | 3 | 57 | 0 | 15 | 151 | 90 | 203–205 | 3450, 1792, 1680. |
| 3 | $CH_3$ | Ph | $CH_3COO$ | β-H | $CHPh_2$ | 150 | 4 | 64 | 0 | 10 | 110 | 80 | amorph. powder | 3380br, 1785, 1735br, 1665. |
| 4 | Ph | tolyl | Cl | β-H | $CHPh_2$ | 150 | 6 | 58 | 0 | 20 | 132 | quant | 187–188 | 1775, 1743, 1668. |
| 5 | $CH_3$ | thenyl | $CH_3COO$ | α-$CH_3O$ | $CHPh_2$ | 500 | 6 | 180 | 0 | 15 | 417 | 90 | 175–176 | 3400, 1790, 1705. |
| 6 | $CH_3$ | thenyl | $CH_3COO$ | α-$CH_3O$ | $CHPh_2$ | 312 | 6 | 110 | 0 | 30 | 235 | 82 | amorph. powder | 3400, 1793, 1736, 1701. |
| 7 | Ph | thenyl | STetr | α-$CH_3O$ | $CHPh_2$ | 86 | 0.9 | 40 | 0 | 40 | — | 79 | 175–176 | 3400, 1790, 1705. |

EXAMPLE FF (OXIDATION AND ELIMINATION)

(Method)

According to the data on Table FF, a sulfide (vii) is dissolved in acetone, mixed with 5N-peracetic acid and the mixture kept at the given temperature for given time to afford a mixture of sulfoxide (viii: cf. Table II) and a cephem type compound (x). This is mixed with a small amount of dimethyl sulfide to decompose excess reagent and the resulting mixture is refluxed to give a cephem type compound (x) formed by elimination of the sulfenyl group from the sulfoxide compound (viii).

TABLE FF

Oxidation and Elimination (Part 2)

| No. | R | R[1] | R[2] | E | B[1] | sulfide (vii) (mg) | $(CH_3)_2CO$ (ml) | 5M—$CH_3$ \| HOOCO (ml) |
|---|---|---|---|---|---|---|---|---|
| 1 | $CH_3$ | Ph | STetr | β-H | H | 232 | vide infra** | |
| 2 | $CH_3$ | tolyl | STetr | β-H | H | 478 | 12 | 0.3 |
| 3 | Ph | Ph | STetr | β-H | H | 360 | 2 | 0.4 |
| 4 | $CH_3$ | tolyl | STetr | α-$CH_3O$ | H | 254 | 6 | 0.15 |
| | | | | | | | $HCON(CH_3)_2$ | |
| 5 | $CH_3$ | thenyl | STetr | α-$CH_3O$ | H | 200 | 25 | 0.24 |
| 6 | $CH_3$ | thenyl | $CH_3COO$ | α-$CH_3O$ | H | 230 | 2 | 0.25 |
| 7 | $CH_3$ | malonyl | STetr | α-$CH_3O$ | H | 212 | 4 | 0.3 |
| | | | | | | | $CH_3COOC_2H_5$ | |
| 8 | Ph | thenyl | Cl | α-$CH_3O$ | $CHPh_2$ | 200 | 2 | |
| 9 | Ph | thenyl | STetr | α-$CH_3O$ | H | 84 | 2.5 | 0.16 |
| 10 | Ph | malonyl | STetr | α-$CH_3O$ | H | 212 | 4 | 1 eq. |

TABLE FF-continued

Oxidation and Elimination (Part 2)

$$\text{(vii)} \xrightarrow[\text{(ii) reflux 30 min.}]{\text{(i) CH}_3\text{CO}_3\text{H}} \text{(x)}$$

| 11 | Ph | thenyl | CH$_3$COO | α-CH$_3$O | H | 105 | 1 | 0.16 |

| No. | temp (°C.) | time (min) | crop (mg) | (%) | mp (°C.) | IR: $\nu_{max}^{CHCl_3}$ cm$^{-1}$* |
|---|---|---|---|---|---|---|
| 1 | 0 | 60 | 168 | 81 | amorph. powder | 3300, 1780, 1710, 1640(Nujol) |
| 2 | rt | 50 | 236 | 55 | 151–152 | — |
| 3 | 0 | 50 | 97 | 34 | amorph. powder | 3300, 1780, 1710, 1640(Nujol) |
| 4 | 0 | 50 | 243 | 88 | amorph. powder | TLC: Rf 0,45 & 0.36 HOAc/EtOAc/ water (8:1:1) |
| 5 | 0 | 20 | 105 | 55 | 95–98 | 3200, 1785, 1695(Nujol). |
| 6 | 0 | 30 | 123 | 60 | amorph. powder | 3400, 1790, 1740, 1705. |
| 7 | 0 | 60 | 147 | 76 | 129–135 | 1780, 1719, 1632 (KBr). |
| 8 | 0 | 30 | 131 | 79 | 162–164 | 3400, 1785, 1725, 1695. |
| 9 | 0 | 30 | 48 | 70 | 95–98 | 3200, 1785, 1695(Nujol). |
| 10 | 0 | 60 | — | 76 | 129–135 | 1780, 1719, 1632(KBr) |
| 11 | 0 | 60 | 56 | 68 | amorph. powder | 3400, 1790, 1740, 1705. |

*unless otherwise specified.
**80% acetone 6 ml/Na$_2$WO$_4$ 2H$_2$O 20 mg/30% H$_2$O$_2$aq 300 mg/NaHCO$_3$ 84 mg.

EXAMPLE FF-1 (Oxidation and Elimination: Selenyl)

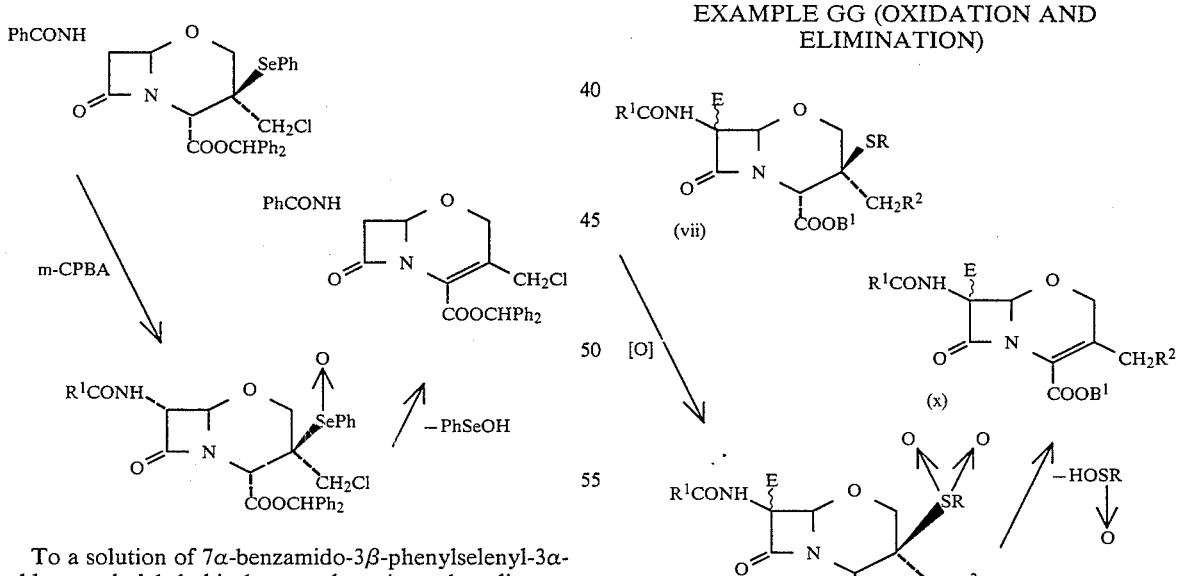

To a solution of 7α-benzamido-3β-phenylselenyl-3α-chloromethyl-1-dethia-1-oxacepham-4α-carboxylic acid diphenylmethyl ester (132 mg) in dichloromethane (3 ml) is added m-chloroperbenzoic acid (49 mg) under ice cooling, and the mixture is permitted to react for 10 minutes. The reaction mixture is poured into aqueous sodium thiosulfate and extracted with ethyl acetate. The extract solution is washed with aqueous sodium hydrogen carbonate and water, dried over sodium sulfate and concentrated under reduced pressure. The residue is purified by silica gel chromatography to give 7α-benzamido-3-chloromethyl-1-dethia-1-oxa-3-cephem-4-carboxylic acid diphenylmethyl ester (63 mg).
IR: $\nu_{max}^{CHCl_3}$ 3340, 1793, 1732, 1675 cm$^{-1}$.

EXAMPLE GG (OXIDATION AND ELIMINATION)

(Method)
According to the data on Table GG, a sulfide (vii) is permitted to react with m-chloroperbenzoic acid in dichloromethane at given temperature for given time to give a sulfone (ix), and then the sulfone is treated with a strong base in dichloromethane to afford a cephem type compound (x).

TABLE GG

Oxidation and Elimination (Part 3)

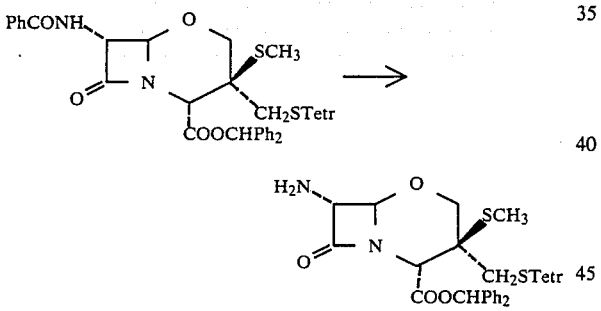

| No. | R¹ | sulfide (vii) E | (mg) | CH₂Cl₂ (ml) | m-CPBA (mg) | temp. (°C.) | time (min) | crop(mg) | sulfone (xi) IR: $\nu_{max}^{CHCl_3}$ cm⁻¹ |
|---|---|---|---|---|---|---|---|---|---|
| 1 | Ph | β-H | 200 | 4 | 126 | 0 | 30 | 190 | 3425, 1785, 1742, 1672. |
| 2 | thenyl | α-CH₃O | 300 | 2 | 200 | 0 | 40 | 234 | 3400, 1790, 1745, 1700. |
| 3 | tolyl | α-CH₃O | 200 | 1.5 | 140 | 0 | 15 | 196 | NMR: $\delta_{ppm}^{CDCl_3}$ 2.33s3H, 2.88s3H. |

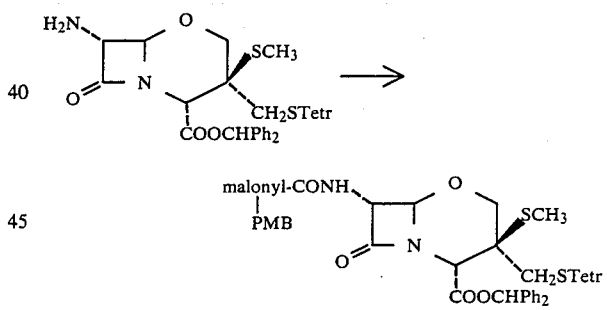

| No. | R¹ | sulfone (ix) E | (mg) | CH₂Cl₂ (ml) | DBU* (μl) | temp. (°C.) | time (min) | crop(mg) | cephem type compound (x) IR: $\nu_{max}^{CHCl_3}$ cm⁻¹ |
|---|---|---|---|---|---|---|---|---|---|
| 1 | Ph | β-H | 150 | 1 | 75 | −20 | 40 | 116 | 3430, 1790, 1725, 1673. |
| 2 | thenyl | α-CH₃O | 230 | 2.5 | 82 | −30 | 25 | 144 | 3420, 1790, 1725, 1700. |

*DBU = 1,5-diazabicyclo[4,5,0]undecene-5.

EXAMPLE HH (EXCHANGE OF A AND B)

(I) Deacylation in A:

To a solution of 7α-benzamido-3β-methylthio-3α-(1-methyl-5-tetrazolyl)thiomethyl-1-dethia-1-oxacepham-4α-carboxylic acid diphenylmethyl ester (160 mg) in chloroform (1.5 ml) is added a solution of pyridine (40 μl) and phosphorus pentachloride (51 mg) in dichloromethane (1.0 ml) in nitrogen under ice cooling. After stirring for 2 hours under ice cooling, the mixture is diluted with methanol 5 ml) and stirred for 2 hours under ice cooling. The reaction mixture is poured onto ice water containing sodium hydrogen carbonate and extracted with dichloromethane. The extract solution is washed with water, dried on sodium sulfate and concentrated in vacuum to give 7α-amino-3β-methylthio-3α-(1-methyl-5-tetrazolyl)thiomethyl-1-dethia-1-oxacepham-4α-carboxylic acid diphenylmethyl ester.

TLC: Rf:=0.30 (C₆H₆-CH₃COOC₂H₅ (1:1)/SiO₂).

Similarly prepared are 7α-amino-3β-methylthio-3α-chloromethyl-1-dethia-1-oxacepham-4α-carboxylic acid diphenylmethyl ester (NMR: $\delta_{ppm}^{CDCl_3}$ 1.67s2H, 2.13s3H, 4.18s1H) and 7α-amino-3β-phenylthio-3α-chloromethyl-1-dethia-1-oxacepham-4α-carboxylic acid diphenylmethyl ester (NMR: $\delta_{ppm}^{CDCl_3}$ 1.80brs2H, 4.25brs1H, 4.60s1H).

(II) Acylation at A:

To a solution of 7α-amino-3β-methylthio-3α-(1-methyl-5-tetrazolyl)thiomethyl-1-dethia-1-oxacepham-4-carboxylic acid diphenylmethyl ester (180 mg) in dichloromethane (6 ml) are added 2-p-methoxybenzyloxyphenyl-2-p-methoxybenzyloxycarbonylacetyl chloride (3.0 mg) and pyridine (0.06 ml), under nitrogen with stirring with ice cooling. After stirring for 30 minutes, the reaction mixture is poured onto ice water and extracted with ethyl acetate. The extract solution is washed with aqueous sodium hydrogen carbonate and water, dried over sodium sulfate and concentrated under reduced pressure. The residue is purified by silica gel chromatography to give 7α-(2-p-methoxybenzyloxyphenyl-2-p-methoxybenzyloxycarbonylacetyl)amino-3β-methylthio-3α-(1-methyl-5-tetrazolyl)thiomethyl-1-dethia-1-oxacepham-4α-carboxylic acid diphenylmethyl ester (252 mg). Yield: 53%.

NMR: $\delta_{ppm}^{CDCl_3}$ 1.93s3H, 3.48s2H, 3.53s2H.

(III) Salt formation at COB:

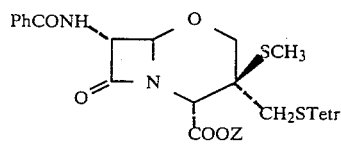

(1) (Z=Na) To a solution of 7α-benzamido-3β-methylthio-3α-(1-methyl-5-tetrazolyl)thiomethyl-1-dethia-1-oxacepham-4α-carboxylic acid in 0.1N-aqueous sodium carbonate is made pH.7.0. The mixed solution is lyophilized to give the corresponding sodium salt.

NMR: $\delta_{ppm}^{D2O}$ 2.02s3H, 4.05s3H, 5.03s1H.

(2) (Z=C$_5$H$_5$N.H) A solution of 7α-benzamido-3β-methylthio-3α-(1-methyl-5-tetrazolyl)thiomethyl-1-dethia-1-oxacephem-4α-carboxylic acid in pyridine is concentrated to give the corresponding pyridinium salt.

NMR: $\delta_{ppm}^{CDCl_3}$ 2.17s3H, 3.97s3H, 4.13s2H, 4.99s1H.

(IV) Esterification at COB:

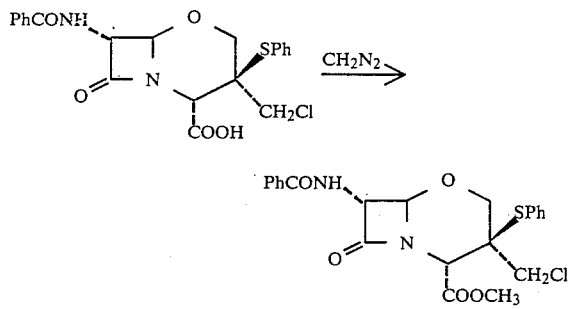

To a solution of 7α-benzamido-1-dethia-1-oxa-3β-phenylthio-3α-chloromethylcepham-4α-carboxylic acid (150 mg) in acetone (5 ml) is added a solution of diazomethane in ether. After 5 minutes reaction, the mixture is concentrated under reduced pressure to dryness. The residue is crystallized from ether to give the corresponding methyl ester (123 mg). mp. 181°–182° C.

(V) Deesterification at COB

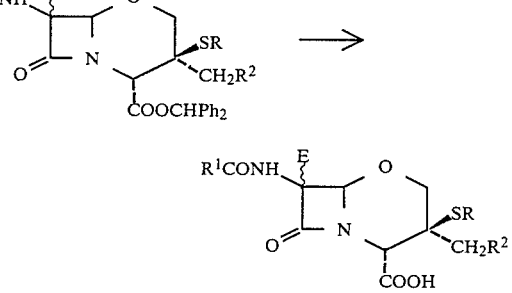

According to the data of Table HH, diphenylmethyl ester (xii) is dissolved in dichloromethane, mixed with trifluoroacetic acid and anisole and then let react for given time at given temperature. By removing solvent, reagent and by-products by a conventional manner, one obtains the corresponding free acid (xiii) as solid material after trituration in ether.

TABLE HH

Free acid

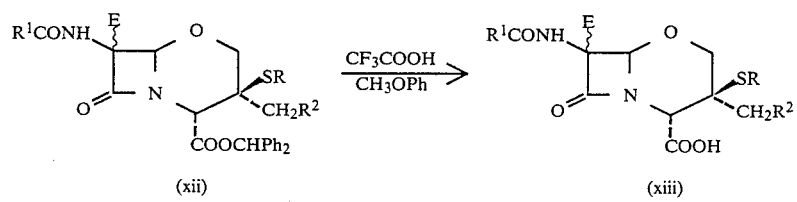

(xii)  (xiii)

| No. | R | R$^1$ | ester (xii) R$^2$ | E | (mg) | Ph\|CH$_2$Cl$_2$ (ml) | CF$_3$\|CH$_3$O (ml) | COOH (ml) | temp (°C.) | time (min) | free acid (xiii) crop(mg) | (%) | IR: $\nu_{max}^{Nujol}$ cm$^{-1}$ |
|---|---|---|---|---|---|---|---|---|---|---|---|---|---|
| 1 | CH$_3$ | Ph | STetr | β-H | 1400 | 10 | 2 | 2 | rt | 90 | 1090 | quant | mp. 194–195° C. |
| 2 | CH$_3$ | Ph | CH$_3$COO | β-H | 300 | 2 | 0.5 | 0.5 | 0 | 90 | 228 | quant | 3350, 1780, 1748, 1633 |
| 3 | CH$_3$ | thenyl | CH$_3$COO | α-CH$_3$O | 850 | 4 | 0.8 | 0.8 | 0 | 120 | 593 | 95 | 3400, 1785, 1750, 1700 |
| 4 | CH$_3$ | thenyl | CH$_3$O | α-CH$_3$O | 550 | 4 | 0.8 | 0.8 | rt | 120 | 279 | 70 | 3400, 1785, 1740–1690 |
| 5 | CH$_3$ | thenyl | STetr | α-CH$_3$O | 300 | 2 | 0.4 | 0.4 | rt | 90 | 224 | quant | mp. 222–223° C. |
| 6 | CH$_3$ | malonyl/PMB | STetr | α-CH$_3$O | 532 | 5.3 | 1.06 | 1.06 | 0 | 1080 | 228 | 93* } | mp. 110° C. |
| 7 | CH$_3$ | tolyl | STetr | β-H | 639 | 6 | 1 | 1 | rt | 90 | 447 | 94 | mp. 204–206° C. |
| 8 | CH$_3$ | tolyl | STetr | α-CH$_3$O | 1500 | 10 | 1.5 | 1.5 | rt | 90 | 714 | 65 | NMR: 2.07s3H, 2.38s3H** |
| 9 | Ph | Ph | Cl | β-H | 1000 | 8 | 1.5 | 1.5 | rt | 40 | 686 | 94 | mp. 125–127° C. |
| 10 | Ph | Ph | STetr | β-H | 450 | 4 | 1 | 1 | rt | 90 | 341 | quant | 3400–3100, 1700, 1740 |
| 11 | Ph | thenyl | Cl | α-CH$_3$O | 1023 | 10 | 2 | 2 | rt | 240 | 752 | 98 | 3400, 1780, 1735, 1695 |
| 12 | Ph | thenyl | STetr | α-CH$_3$O | 228 | 2.9 | 0.58 | 0.58 | 0 | 240 | 145 | 65 | mp. 190–205° C. |
| 13 | Ph | thenyl | CH$_3$COO | α-CH$_3$O | 444 | 4 | 0.8 | 0.8 | rt | 60 | 311 | 92 | 3400, 1780, 1745, 1700 |
| 14 | Ph | malonyl/PMB | STetr | α-CH$_3$O | 135 | 2 | 2 | 2 | rt | 90 | 51 | 55* } | 3200, 1770, 1730, 1680 |

*p-methoxybenzyl group is removed during the reaction.
**NMR: $\delta_{ppm}^{CD_3COCD_3}$

TABLE II

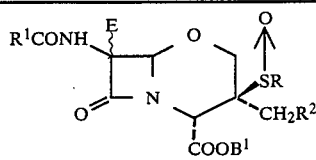

| No. | R | $R^1$ | $R^2$ | E | $B^1$ | TLC Rf | Developing solvent |
|---|---|---|---|---|---|---|---|
| 1 | $CH_3$ | tolyl | STetr | β-H | H | 0.10 / 0.08 * | $CH_3COOC_2H_5$—$CH_3COOH$—$H_2O$ (16:1:1) |
| 2 | $CH_3$ | tolyl | STetr | α-$CH_3O$ | H | 0.45 / 0.36 * | $CH_3COOC_2H_5$—$CH_3COOH$—$H_2O$ (8:1:1) |
| 3 | $CH_3$ | thenyl | $CH_3COO$ | α-$CH_3O$ | H | 0.20 | $CH_3COOC_2H_5$—$CH_3COOH$—$H_2O$ (16:1:1) |
| 4 | $CH_3$ | malonyl | STetr | α-$CH_3O$ | H | 0.63 | $CH_3COCH_3$—$CH_3COOH$—$H_2O$ (95:5:10) |
| 5 | Ph | Ph | STetr | β-H | H | 0.64 | $CH_3COOC_2H_5$—COOH—$H_2O$ (8:1:1) |
| 6 | $CH_3$ | Ph | STetr | β-H | $CHPh_2$ | 0.085 | $C_6H_6$—$CH_3COOC_2H_5$ (9:1) |
| 7 | Ph | thenyl | STetr | α-$CH_3O$ | H | 0.50 | $CH_3COOC_2H_5$—$CH_3COOH$—$H_2O$ (8:1:1) |
| 8 | Ph | thenyl | $CH_3COO$ | α-$CH_3O$ | H | 0.23 | $CH_3COOC_2H_5$—$CH_3COOH$—$H_2O$ (16:1:1) |
| 9 | Ph | thenyl | STetr | α-$CH_3O$ | $CHPh_2$ | 0.28 | $C_6H_6$—$CH_3COOC_2H_5$ (2:1) |
| 10 | Ph | thenyl | Cl | α-$CH_3O$ | $CHPh_2$ | 0.36 | $C_6H_6$—$CH_3COOC_2H_5$ (2:1) |
| 11 | Ph | malonyl | STetr | α-$CH_3O$ | H | 0.57 | $CH_3COCH_3$—$CH_3COOH$—$H_2O$ (95:5:10) |

* The two spots correspond to the stereoisomers in relation to sulfoxide bond.

What we claim is:
1. A compound of the formula

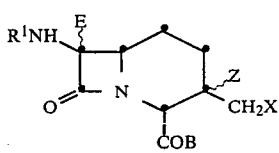

wherein
$R^1$ is
(1) $C_1$ to $C_{10}$ alkanoyl,
(2) $C_1$ to $C_7$ haloalkanoyl,
(3) azidoacetyl, cyanoacetyl, trifluoromethylthioacetyl, cyanomethylthioacetyl, or (4-pyridon-1-yl)acetyl;
(4) acyl group of the following formula Ar—CO— wherein Ar is an aryl selected from furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, dihydrophenyl, tetrahydrophenyl, tetrahydropyrimidyl, naphthyl, benzothiazolyl, indolyl, quinolyl, isoquinolyl, benzopyrimidyl, cinnolinyl, pyridopyrimidyl, or indanyl ring group;
(5) group of the following formula:

Ar—CQQ'—CO— wherein Ar is as defined above and Q and Q' each is hydrogen or methyl;
(6) acyl group of the following formula:

Ar—G—CQQ'—CO— wherein Ar, Q and Q' each is as defined above and G is oxygen, sulfur, or imino;

(7) acyl group of the following formula

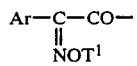

wherein Ar is as defined above and $T^1$ is hydrogen or $C_1$ to $C_6$ alkyl;
(8) acyl group of the following formula:

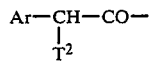

wherein Ar is as defined above and $T^2$ is one of (i) hydroxy or $C_1$ to $C_{10}$ acyloxy, (ii) carboxy or protected carboxy, (iii) sulfo or $C_1$ to $C_5$ alkoxysulfonyl, or a group of the formula:

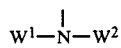

in which $W^1$ and $W^2$ each is hydrogen or a $C_1$ to $C_{15}$ aminosubstituent;
(9) 5-aminoadipoyl, 5-aminoadipoyl protected at the amino or 5-aminoadipoyl protected at the carboxy;
(10) acyl group of the following formula:

L—O—CO— wherein L is an easily removable and unsubstituted or substitured $C_1$ to $C_{10}$ hydrocarbyl group; or
(11) $C_1$ to $C_{20}$ optionally substituted hydrocarbyl, $C_3$ to $C_{10}$ organic silyl, or $C_1$ to $C_{10}$ sulfenyl,
COB is carboxy or protected carboxy, the carboxy protecting group B in said COB being $C_1$ to $C_{10}$ alkoxy, $C_1$ to $C_6$ haloalkoxy, $C_3$ to $C_{10}$ acylalkoxy, $C_3$ to $C_{10}$ alkoxyalkoxy, $C_2$ to $C_{10}$ aminoalkoxy, aryloxy, aralkoxy, $C_1$ to $C_{10}$ alkylsilyloxy, $C_1$ to $C_{10}$ alkylstannyloxy, $C_1$ to $C_{10}$ acyloxy, inorganic acyloxy, metal oxy of a group I, II or III metal in the periodical table, $C_1$ to $C_{15}$ hydrocarbylammoniooxy, $C_1$ to $C_{10}$ hydrocarbylthio or mercapto, $C_1$ to $C_5$ alkylamino, di-$C_1$ to $C_5$ alkylamino, hydrazinyl or azido;

E is β-hydrogen or α-methoxy;

X is hydrogen, halogen, hydroxy, $C_1$ to $C_4$ alkanoyloxy, substituted $C_1$ to $C_4$ alkanoyloxy, aroyloxy, carbonic acyloxy, $C_1$ to $C_6$ alkoxy, aralkoxy of the formula Ar—$CH_2$O— or aryloxy of the formula Ar—O— in which Ar is as defined above, mercapto, $C_1$ to $C_5$ alkanoylthio, aroylthio, $C_1$ to $C_6$-alkylthio, aralkylthio, arylthio of the formula Ar—S— in which Ar is as defined above, amino, azido, hydrazinyl, acetylamino, methylamino, pyridinium, picolinium, 4-carboxypyridinium, carbamoylpyridinium, hydroxymethylpyridinium, carboxymethylpyridinium, or chloropyridinium, and Z is a group of the formula $RS(O)_n$— or $RSe(O)_n$— in which R is $C_1$ to $C_3$ alkyl or monocyclic aryl and n is 0, 1 or 2.

2. A sulfide compound as claimed in claim 1 that is a compound of the following formula

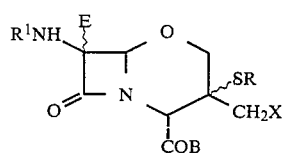

wherein $R^1$, E, R, X and COB are as defined in claim 1.

3. A sulfoxide compound as claimed in claim 1 that is a compound of the following formula

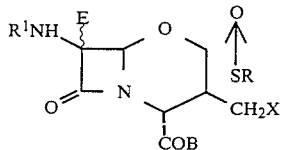

wherein $R^1$, E, R, X and COB are as defined in claim 1.

4. A sulfone compound as claimed in claim 1 that is a compound of the following formula

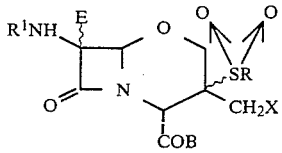

wherein $R^1$, E, R, X and COB are as defined in claim 1.

5. A selenyl compound as claimed in claim 1 that is a compound of the following formula

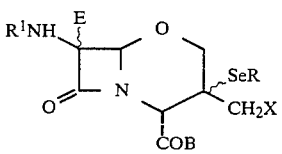

wherein $R^1$, E, R, X and COB are as defined in claim 1.

6. A selenoxide compound as claimed in claim 1 that is a compound of the following formula

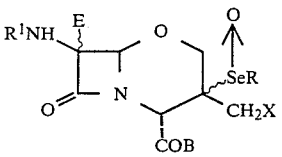

wherein $R^1$, E, R, X and COB are as defined in claim 1.

* * * * *

UNITED STATES PATENT AND TRADEMARK OFFICE
CERTIFICATE OF CORRECTION

PATENT NO. : 4,533,730
DATED : August 6, 1985
INVENTOR(S) : MITSURU YOSHIOKA, SHOICHIRO UYEO, YOSHIO HAMASHIMA, IKUO KIKKAWA, TERUJI TSUJI and WATARU NAGATA It is certified that error appears in the above-identified patent and that said Letters Patent is hereby corrected as shown below:

Column 67, correct the formula appearing at lines 30 to 34 to read as follows:

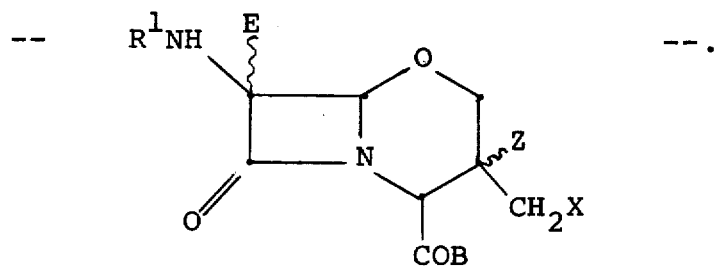

Signed and Sealed this

Fourteenth Day of January 1986

[SEAL]

Attest:

DONALD J. QUIGG

Attesting Officer    Commissioner of Patents and Trademarks